United States Patent
Leighton et al.

(10) Patent No.: US 10,683,288 B2
(45) Date of Patent: Jun. 16, 2020

(54) EPOTHILONE B AND DICTYOSTATIN ANALOGS, THEIR PREPARATION AND USE

(71) Applicant: The Trustees of Columbia University in the City of New York, New York, NY (US)

(72) Inventors: James Leighton, New York, NY (US); Stephen Ho, New York, NY (US); Corinne Foley, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 15/747,313

(22) PCT Filed: Jul. 22, 2016

(86) PCT No.: PCT/US2016/043734
§ 371 (c)(1),
(2) Date: Jan. 24, 2018

(87) PCT Pub. No.: WO2017/019561
PCT Pub. Date: Feb. 2, 2017

(65) Prior Publication Data
US 2018/0215748 A1 Aug. 2, 2018

Related U.S. Application Data

(60) Provisional application No. 62/196,819, filed on Jul. 24, 2015, provisional application No. 62/196,825, filed on Jul. 24, 2015.

(51) Int. Cl.
| | |
|---|---|
| C07D 417/06 | (2006.01) |
| C07D 313/00 | (2006.01) |
| C07D 417/04 | (2006.01) |
| C07D 413/06 | (2006.01) |
| C07D 405/06 | (2006.01) |
| C07D 493/04 | (2006.01) |

(52) U.S. Cl.
CPC ......... *C07D 417/06* (2013.01); *C07D 313/00* (2013.01); *C07D 405/06* (2013.01); *C07D 413/06* (2013.01); *C07D 417/04* (2013.01); *C07D 493/04* (2013.01)

(58) Field of Classification Search
CPC .. C07D 313/00; C07D 417/06; C07D 493/04; C07D 405/06; C07D 413/06; C07D 417/04
See application file for complete search history.

(56) References Cited

U.S. PATENT DOCUMENTS

| 7,214,527 B2 | 5/2007 | Basch et al. |
| 8,859,629 B2 | 10/2014 | van Delft et al. |
| 2005/0208620 A1* | 9/2005 | Basch .................... C07K 14/79 435/69.1 |
| 2012/0095066 A1* | 4/2012 | Reer .................... A61K 31/724 514/367 |
| 2014/0072633 A1 | 3/2014 | Eliasof et al. |

OTHER PUBLICATIONS

PubChem CID 44158585 (available Aug. 24, 2009).*
Foley, Corinne N., et al. "Synthesis and Evaluation of a Linkable Functional Group-Equipped Analogue of the Epothilones." ACS medicinal chemistry letters 8.7 (2017): 701-704.
"Pubchem CID 44158585" Create Date: Aug. 24, 2009, Date Accessed by ISA: Nov. 7, 2016.
Zhan et al. "C6-C8 Bridged Epothilones: Consequences of Installing a Conformational Lock at the Edge of the Macrocycle" Chemistry A European Journal, Nov. 30, 2011, vol. 17, p. 14792-14804.
Stephen Ho, "Studies in Polyketide Total Synthesis", Columbia University, Thesis defended 2014.
Corinne N. Foley, "The Development and Application of a New Approach to the Rapid Synthesis of Polypropionate Stereotriads", Columbia University, Thesis defended 2015.

(Continued)

*Primary Examiner* — Valerie Rodriguez-Garcia
(74) *Attorney, Agent, or Firm* — John P. White; Gary J. Gershik; Cooper & Dunham LLP

(57) ABSTRACT

A compound having the structure:

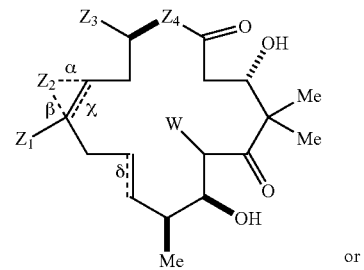

or

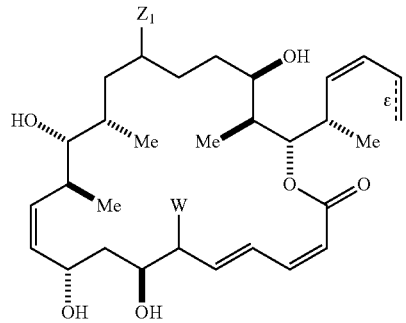

9 Claims, 5 Drawing Sheets

(56) References Cited

OTHER PUBLICATIONS

Stephen Ho, et al. "A 'Methyl Extension' Strategy for Polyketide Natural Product Linker Site Validation and its Application to Dictyostatin", J Am Chem Soc., Nov. 11, 2015, 137(44), pp. 14047-14050.
International Search Report dated Dec. 1, 2016 in connection with PCT International Application No. PCT/US2016/043734.
Written Opinion of the International Searching Authority dated Dec. 1, 2016 in connection with PCT International Application No. PCT/US2016/043734.

* cited by examiner

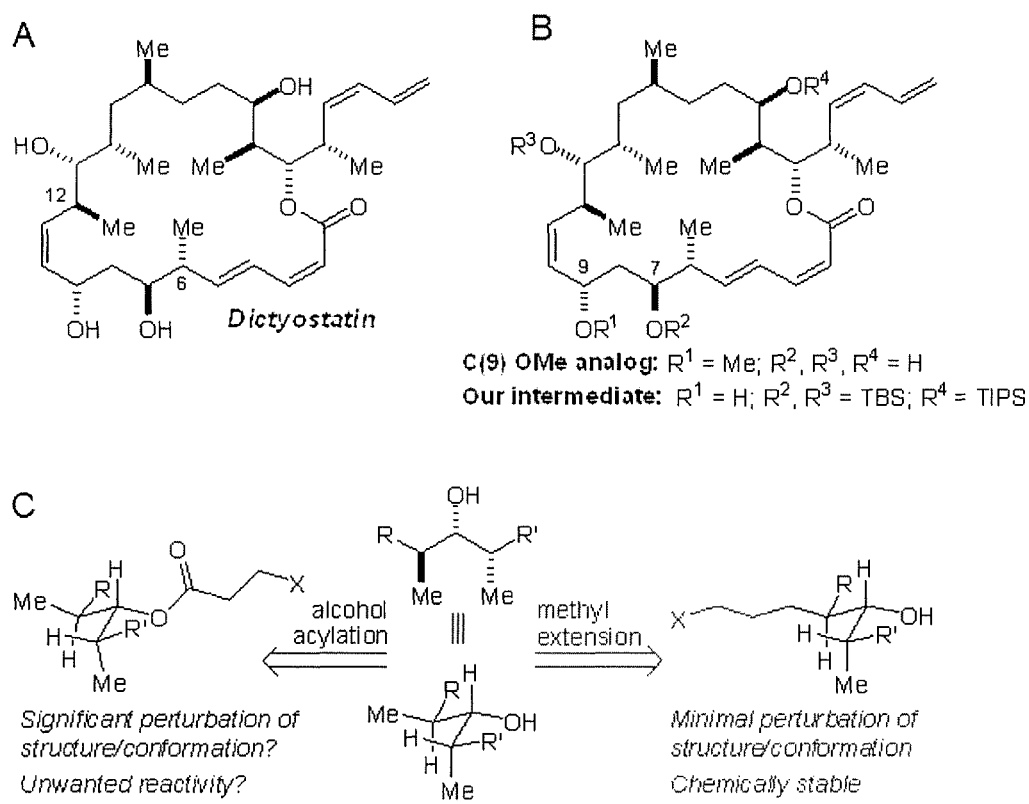
Fig. 2A-C

EPOTHILONE B AND DICTYOSTATIN ANALOGS, THEIR PREPARATION AND USE

CROSS-REFERENCE TO RELATED APPLICATIONS

This application is a § 371 national stage of PCT International Application No. PCT/US2016/043734, filed Jul. 22, 2016, claiming priority of U.S. Provisional Application Nos. 62/196,819, filed Jul. 24, 2015 and 62/196,825, filed Jul. 24, 2015, the contents of each of which are hereby incorporated by reference.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

The invention was made with government support under Grant number GM058133 awarded by the National Institutes of Health. The government has certain rights in the invention.

BACKGROUND OF THE INVENTION

Strategies for the selective delivery of small molecule cancer chemotherapeutic agents to tumor cells (e.g. antibody-drug conjugates) hold promise as a way to, in effect, increase their therapeutic index (Chari, R. V. J. et al. 2014). A requirement for the drug in many of these approaches is a validated linker strategy (Ducry, L. et al. 2010), the most critical component of which is the identification of a site on the drug that may be modified without interfering with its ability to access and bind to its target receptor and express its activity. More broadly, the identification of such modifiable sites on bioactive natural products can facilitate chemical biology and mechanism of action studies and enable exploration of more novel linked constructs.

Non-aromatic polyketide natural products are a pharmaceutically important class of compounds due to their often high levels of biological activity. A number of these compounds have been identified as potent antitumor agents and have thus been highly pursued for use as therapeutic agents. By binding to tubulin, the molecules disrupt microtubule dynamics, inhibiting mitosis and leading to cell death. Due to limited access to some of these important natural products or a need for innate structural modifications to improve their pharmacological properties, the use of synthetic chemistry has become paramount for the further development of a number of polyketides as therapeutic agents.

The epothilones are a family of cytotoxic natural products that were first isolated from the myxobacterium *Sorangium cellulosum* in 1987 (Hofle, G. et al. 1996; Gerth, K. et al. 1996). While initially of some interest for their antifungal properties, these compounds attracted much more attention from the scientific community in 1993 when they were found to exhibit potent taxane-like antitumor activity (Bollag, D. et al. 1995).

Dictyostatin (Petit, G. R. et al. 1994; Isbrucker, R. A. et al. 2003; Paterson, I. et al. 2004), for which we recently reported a synthesis that proceeds in just 14 steps in the longest linear sequence (Ho, S. et al. 2013), is a worthy candidate for linker strategy validation in that it is among the most potent of the microtubule-stabilizing agents (MSAs) known to bind to the taxane binding site on the β-tubulin subunits of microtubules, retains significant potency against several taxane-resistant cell lines, and has recently been shown to be a rare example of a brain-penetrant MSA (Brunden, K. R. et al. 2013).

Epothilones A (Epo A) and B (Epo B), have been found to act via the same microtubule-stabilizing mechanism of action as taxol, the first therapeutic agent with this mechanism to obtain FDA approval (FIG. 1). While Epo A exhibits similar activity to taxol in a number of cancer cell lines, Epo B is about tenfold more potent in the same cell lines (Altmann, K.-H. et al. 2007). Though they act at the same microtubule binding site, the epothilones are significantly more active than taxol for inhibiting the growth of multi-drug-resistant (MDR) cancer cell lines. In taxol-resistant cancer cell lines that overexpress phosphoglycoprotein 170 (P-gp), epothilones A and B are able to maintain almost full anti-proliferative activity because they are poor substrates for the P-gp efflux pump (Altmann, K.-H. et al. 2000). Epothilones have also been shown to retain activity in cancer cell lines that have developed taxol-resistance due to particular tubulin mutations, which is the another main mechanism of taxol-resistance (Giannakakou, P. et al. 1997).

Besides activity, the epothilones have the practical advantage of exhibiting increased solubility relative to taxol, meaning they would not require clinical formulation vehicles such as Cremophor which has been implicated for some of taxol's clinical side effects (Rowinsky, E. K. 1997). Due to these advantages over taxol, the epothilones have become highly attractive targets for drug discovery efforts and total synthesis efforts. Over 30 total syntheses of Epo A and B have been reported, as well as extensive studies of the structure-activity relationship (SAR) of the epothilones. As a result of these efforts, a number of epothilone-derived compounds have been advanced to clinical trials as potential anticancer drugs (Nicolaou, K. C. et al. 1998; Harris, C. et al. 1999; Nicolaou, K. C. et al. 2001).

Dictyostatin (Petit, G. R. et al. 1994; Isbrucker, R. A. et al. 2003; Paterson, I. et al. 2004)), for which we recently reported a synthesis that proceeds in just 14 steps in the longest linear sequence (Ho, S. et al. 2013), is a worthy candidate for linker strategy validation in that it is among the most potent of the microtubule-stabilizing agents (MSAs) known to bind to the taxane binding site on the β-tubulin subunits of microtubules, retains significant potency against several taxane-resistant cell lines, and has recently been shown to be a rare example of a brain-penetrant MSA (Brunden, K. R. et al. 2013).

SUMMARY OF THE INVENTION

The present invention provides a compound having the structure:

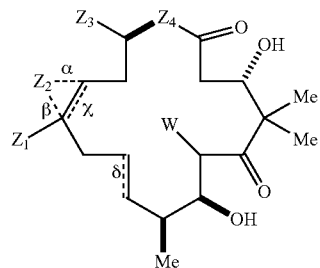

wherein $Z_1$ is —$CH_3$ or —$CF_3$;

$Z_2$ is absent or present and when present is —O—;

$Z_3$ is

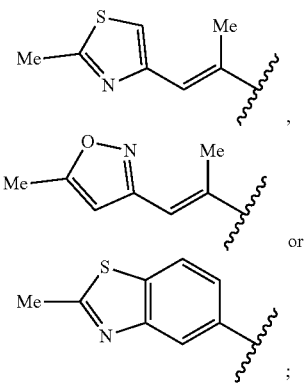

or

;

$Z_4$ is —O— of —NH—;

W is an organic moiety other than H, $C_1$-$C_3$ alkyl or $C_1$-$C_3$ alkenyl;

α is a bond and is absent or present,

β is a bond and is absent or present,

χ is a bond and is absent or present,

δ is a bond and is absent or present, wherein when α, β, and $Z_1$ are present, then χ is absent, and when χ is present, then α, β, and $Z_1$ are absent or a stereoisomer or a pharmaceutically acceptable salt or ester thereof.

The present invention further provides a compound having the structure:

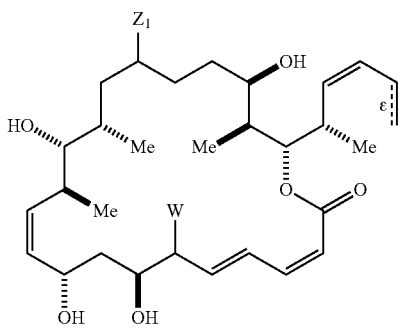

wherein W is an organic moiety other than —H. —$CH_3$,

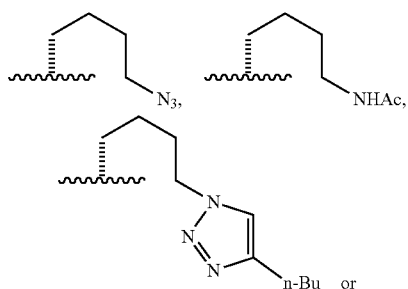

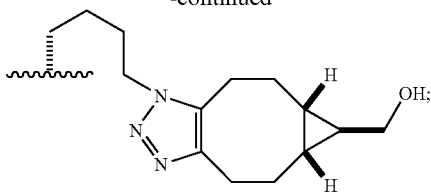

$Z_1$ is —H or —$CH_3$; and

ε is a bond and is absent or present, or a stereoisomer or a pharmaceutically acceptable salt or ester thereof.

BRIEF DESCRIPTION OF THE FIGURES

FIG. 2A: The potent MSA dictyostatin has only four hydroxyl groups for synthetically straightforward modification.

FIG. 2B: Paterson and Wright's C(9)-OMe analog 1 retains the low nM potency of dictyostatin, and the penultimate intermediate in our synthesis is 2 in which the C(9)-OH group is, uniquely, unprotected.

FIG. 2C: In crowded polypropionate arrays, alcohol acylation might be expected to result in non-trivial perturbations to local electronic and steric structure and in turn to global conformation as well as raise concerns about acyl group migration and/or cleavage. By contrast, extension of one of the methyl groups should result in a minimal perturbation of structure and conformation and obviate any concerns about chemical stability. TBS, tert-butyldimethylsilyl; TIPS, tri-isopropylsilyl.

FIGS. 3A and 3B are reprinted with permission from *J. Am. Chem. Soc.* 133, 2427-2436 (2011).

DETAILED DESCRIPTION OF THE INVENTION

Figure 1:
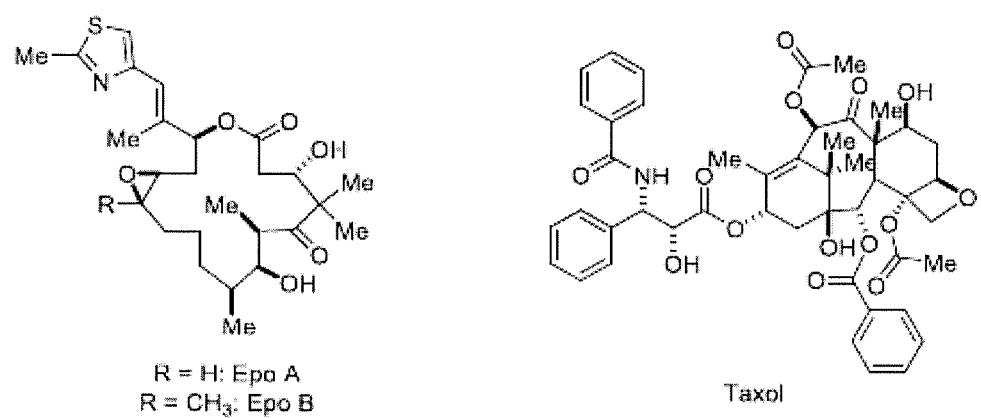
FIG. 1: Structures of the Epothilones and Taxol.

The present invention provides a compound having the structure:

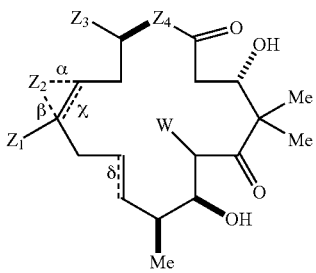

wherein $Z_1$ is —CH$_3$ or —CF$_3$;

$Z_2$ is absent or present and when present is —O—;

$Z_3$ is

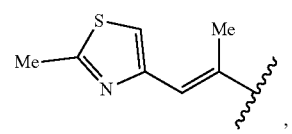

,

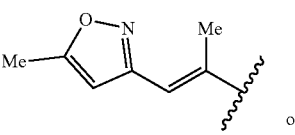

or

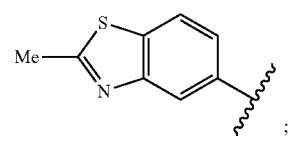

;

$Z_4$ is —O— of —NH—;

W is an organic moiety other than H, C$_1$-C$_3$ alkyl or C$_1$-C$_3$ alkenyl;

α is a bond and is absent or present,

β is a bond and is absent or present,

χ is a bond and is absent or present,

δ is a bond and is absent or present, wherein when α, β, and $Z_1$ are present, then χ is absent, and when χ is present, then α, β, and $Z_1$ are absent or a stereoisomer or a pharmaceutically acceptable salt or ester thereof.

The present invention also provides a compound having the structure:

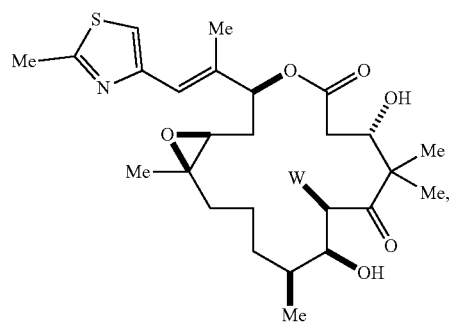

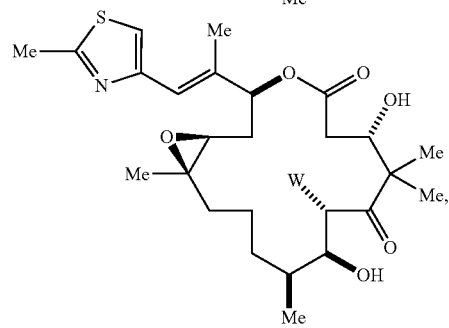

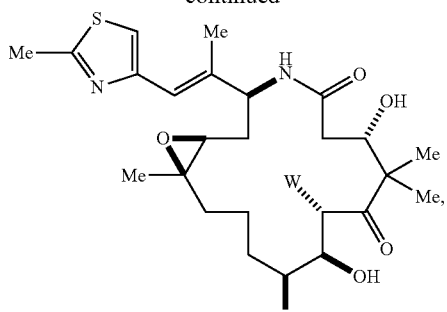

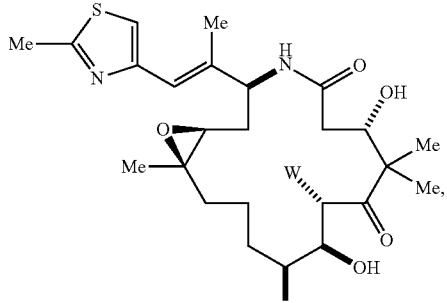

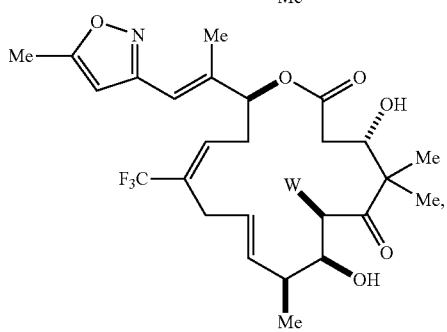

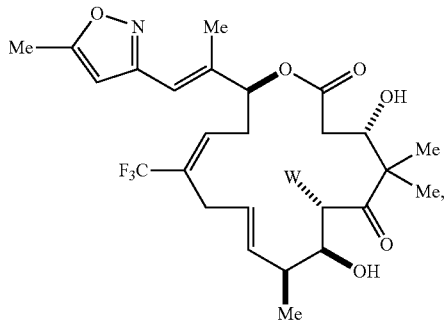

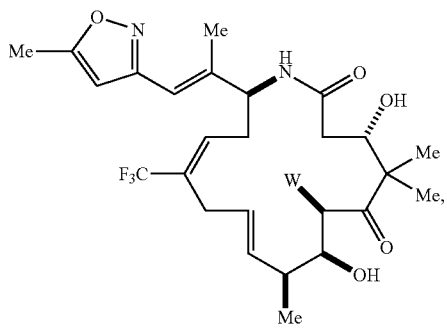

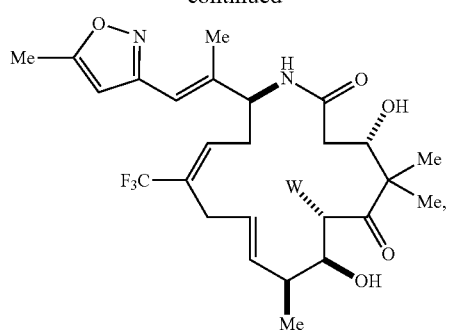
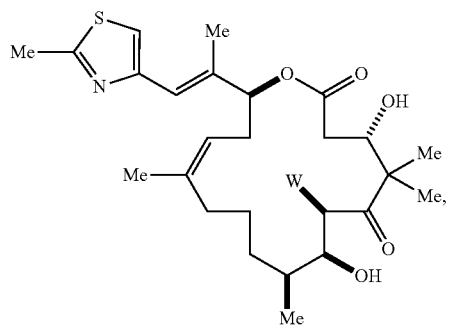
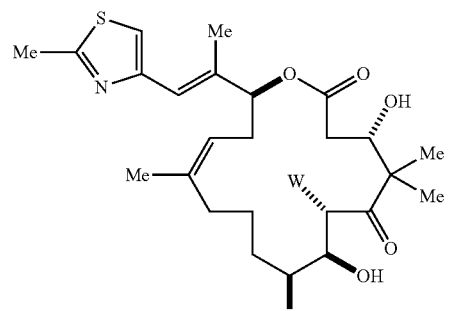
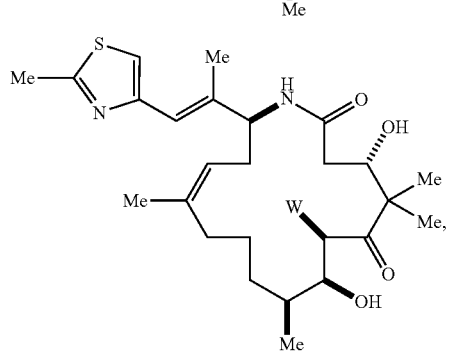
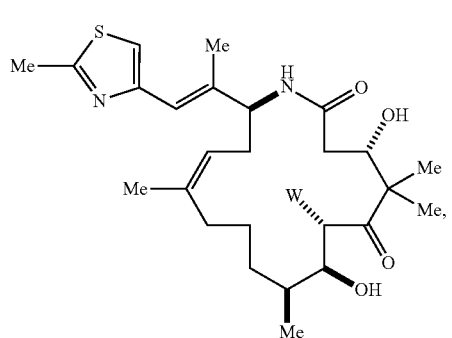
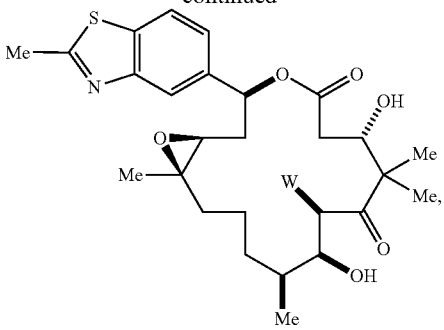
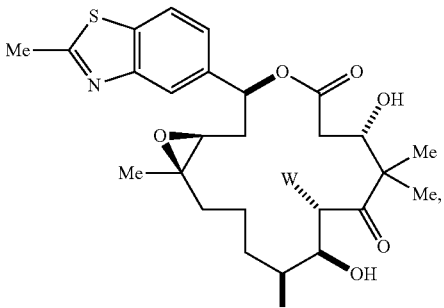
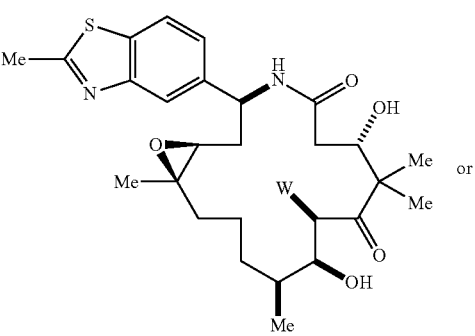
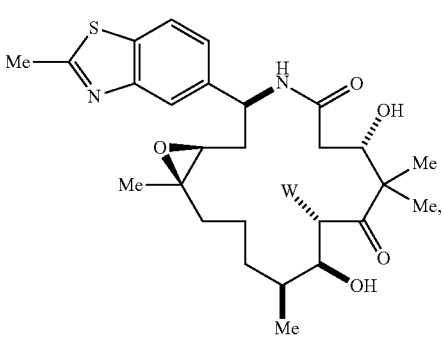
wherein W is an organic moiety other than H, $C_1$-$C_3$ alkyl or $C_1$-$C_3$ alkenyl;
or a stereoisomer or a pharmaceutically acceptable salt or ester thereof.
The present invention also provides a compound having the structure:

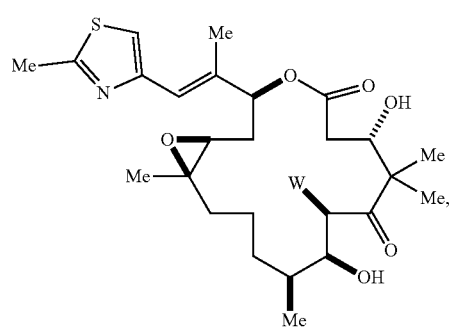
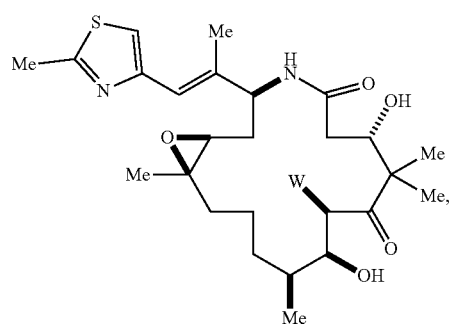
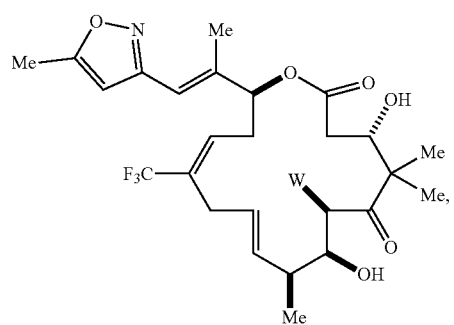
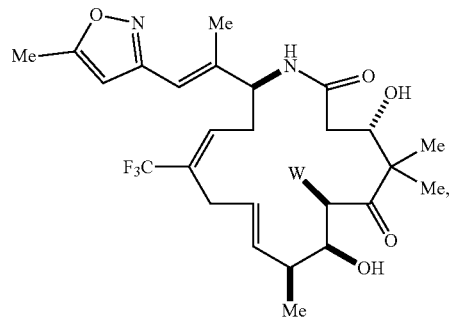
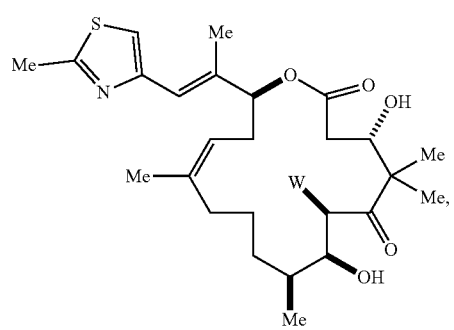

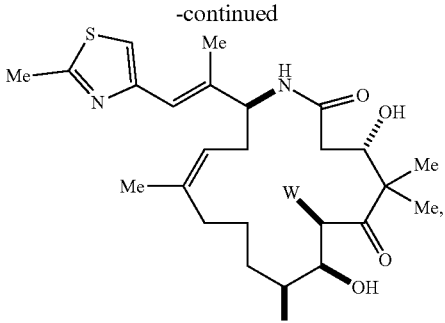
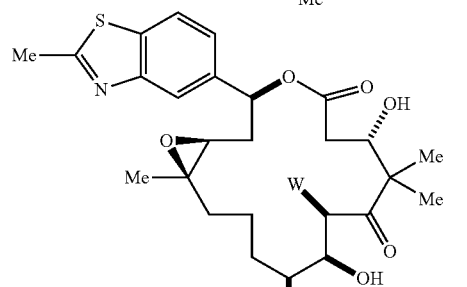
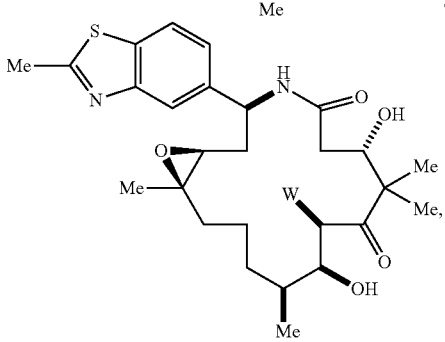

wherein W is an organic moiety other than H, $C_1$-$C_3$ alkyl or $C_1$-$C_3$ alkenyl;

or a stereoisomer or a pharmaceutically acceptable salt or ester thereof.

The present invention provides a compound having the structure:

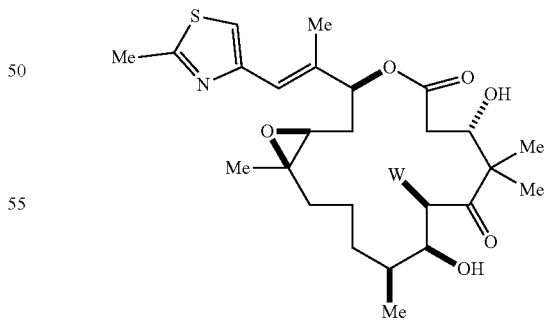

wherein W is an organic moiety other than H, $C_1$-$C_3$ alkyl or $C_1$-$C_3$ alkenyl, or a stereoisomer or a pharmaceutically acceptable salt or ester thereof.

In some embodiments, the compound wherein W is an organic moiety other than H, $C_1$-$C_4$ alkyl or $C_1$-$C_4$ alkenyl.

In some embodiments, the compound wherein W is an organic moiety other than H, $C_1$-$C_5$ alkyl or $C_1$-$C_5$ alkenyl.

In some embodiments, the compound
wherein
W is $C_4$-$C_{20}$ alkyl, $C_4$-$C_{20}$ alkenyl, alkynyl, alkylcycloalkyl, alkylaryl, alkylheteroaryl, alkyl-$N_3$, alkyl-SH, alkyl-OH, alkyl-$NH_2$, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$, or alkyl-maleimide,
wherein
  $R_1$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_2$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_3$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_4$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide.

In some embodiments, the compound
wherein
W is $C_5$-$C_{20}$ alkyl, $C_5$-$C_{20}$ alkenyl, alkynyl, alkylcycloalkyl, alkylaryl, alkylheteroaryl, alkyl-$N_3$, alkyl-SH, alkyl-OH, alkyl-$NH_2$, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$, or alkyl-maleimide,
wherein
  $R_1$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_2$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_3$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_4$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide.

In some embodiments, the compound
wherein
W is $C_6$-$C_{20}$ alkyl, $C_6$-$C_{20}$ alkenyl, alkynyl, alkylcycloalkyl, alkylaryl, alkylheteroaryl, alkyl-$N_3$, alkyl-SH, alkyl-OH, alkyl-$NH_2$, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$, or alkyl-maleimide,
wherein
  $R_1$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_2$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_3$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_4$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide.

In some embodiments, the compound having the structure:

[Chemical structure diagram of an epothilone-like macrocyclic compound bearing a thiazole group, epoxide, and W substituent]

wherein
W is $C_4$-$C_{20}$ alkyl, $C_4$-$C_{20}$ alkenyl, alkynyl, alkylcycloalkyl, alkylaryl, alkylheteroaryl, alkyl-$N_3$, alkyl-SH, alkyl-OH, alkyl-$NH_2$, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$ or alkyl-maleimide,
wherein
  $R_1$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_2$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_3$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide
  $R_4$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide, W is other than

[Chemical structures of three W substituent groups: an alkyl chain terminating in $N_3$; an alkyl chain terminating in NHAc; and a triazole-linked bicyclic carbamate-PEG-urea-n-pentyl group]

In some embodiments, the compound wherein W is $C_4$-$C_{20}$ alkyl, $C_4$-$C_{20}$ alkenyl, alkynyl, alkylcycloalkyl, alkylaryl, alkylheteroaryl, alkyl-$N_3$, alkyl-SH, alkyl-OH, alkyl-$NH_2$, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$, or alkyl-maleimide,
wherein
  $R_1$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide $R_2$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide $R_3$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide $R_4$ is H, alkyl, alkenyl, alkynyl, cycloalkyl, aryl, heteroaryl, polyether, alkyl-$N_3$, alkyl-SH, alkyl-OH, alkyl-$NH_2$ or alkyl-maleimide, and n is 1-3 or 5-20.

In some embodiments, the compound wherein

W is $C_4$-$C_{20}$ alkyl, $C_4$-$C_{20}$ alkenyl, alkynyl, alkylcycloalkyl, alkylaryl, alkylheteroaryl, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$, wherein $R_1$ is alkyl, alkenyl, alkynyl, cycloalkyl, aryl, heteroaryl or a polyether, $R_2$ is alkyl, alkenyl, alkynyl, cycloalkyl, aryl, heteroaryl or a polyether, $R_3$ is H, alkyl, alkenyl, alkynyl, cycloalkyl, aryl, heteroaryl or a polyether, $R_4$ is H, alkyl, alkenyl, alkynyl, cycloalkyl, aryl, heteroaryl or a polyether.

In some embodiments, the compound wherein W is alkyl-$N_3$, alkyl-SH, alkyl-OH, alkyl-$NH_2$, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$ or alkyl-maleimide, $R_1$ is alkyl-$N_3$, alkyl-SH, alkyl-OH, alkyl-$NH_2$, or alkyl-maleimide $R_2$ is alkyl-$N_3$, alkyl-SH, alkyl-OH, alkyl-$NH_2$, or alkyl-maleimide $R_3$ is alkyl-$N_3$, alkyl-SH, alkyl-OH, alkyl-$NH_2$, or alkyl-maleimide, and $R_4$ is alkyl-$N_3$, alkyl-SH, alkyl-OH, alkyl-$NH_2$ or alkyl-maleimide.

In some embodiments, the compound wherein W is —$(CH_2)_n$—$N_3$, wherein n is 1-20.

In some embodiments, the compound wherein W is —$(CH_2)_n$—NHAc, wherein n is 1-20.

In some embodiments, the compound wherein W is

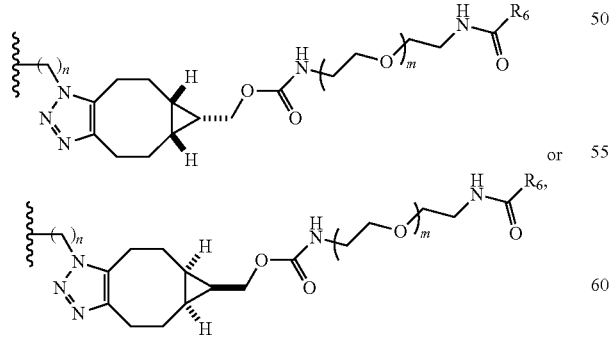

wherein n is 1-20;

m is 1-10; and $R_6$ is H, alkyl, alkenyl, alkynyl, cycloalkyl, aryl, heteroaryl or a polyether.

In some embodiments, the compound wherein W is —$(CH_2)_n$—$N_3$, wherein n is 1-3 or 5-20.

In some embodiments, the compound wherein W is —$(CH_2)_n$—NHAc, wherein n is 1-3 or 5-20.

In some embodiments, the compound wherein W is

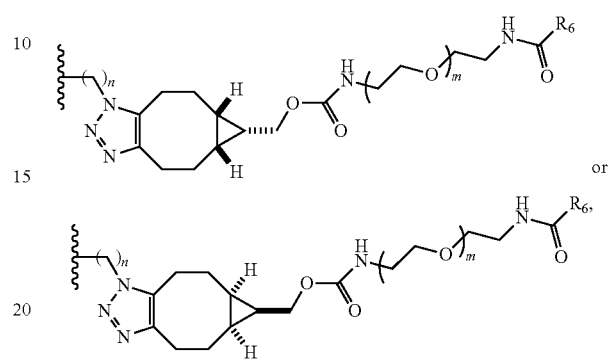

wherein n is 1-3 or 5-20;

m is 1-10; and $R_6$ is H, alkyl, alkenyl, alkynyl, cycloalkyl, aryl, heteroaryl or a polyether.

In some embodiments, the compound wherein W is

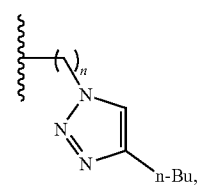

wherein n is 1-20.

In some embodiments, the compound wherein W is

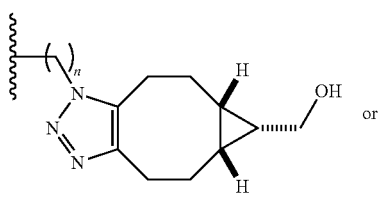

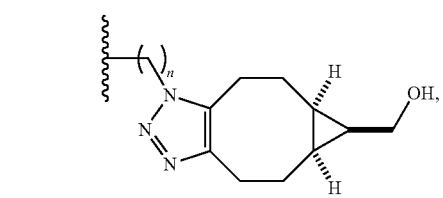

wherein n is 1-20.

In some embodiments, the compound wherein W is

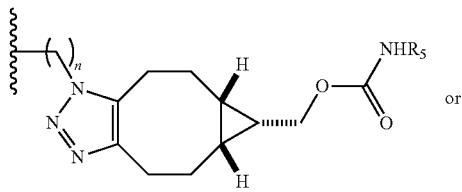

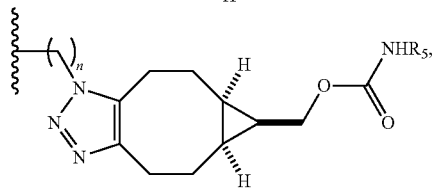

wherein n is 1-20; and
R$_5$ is H, alkyl, alkenyl, alkynyl, cycloalkyl, aryl, heteroaryl or a polyether.

In some embodiments, the compound wherein W is

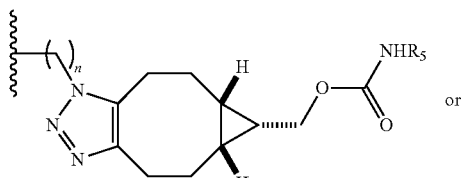

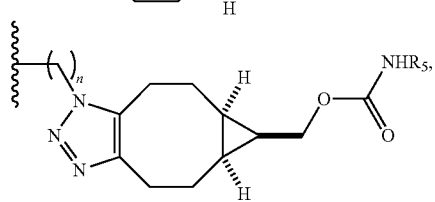

wherein n is 1-20; and
R$_5$ is H, alkyl, alkenyl, alkynyl, cycloalkyl, aryl or heteroaryl.

In some embodiments, the compound wherein W is

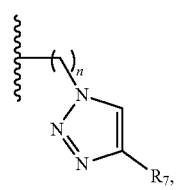

wherein n is 1-20; and
R$_7$ is H, C$_1$-C$_3$ alkyl, C$_5$-C$_{20}$ alkyl, alkenyl, alkynyl, cycloalkyl, aryl, heteroaryl or a polyether.

In some embodiments, the compound wherein W is

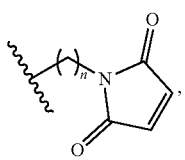

wherein n is 1-20.

In some embodiments, the compound wherein W is

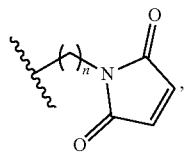

wherein n is 4-20.

In some embodiments, the compound wherein W is

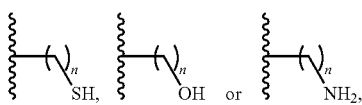

wherein n is 1-20.

In some embodiments, the compound wherein W is

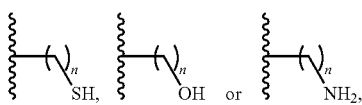

wherein n is 4-20.

In some embodiments, the compound wherein W is

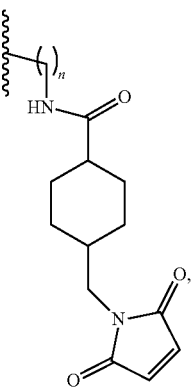

wherein n is 1-20.

In some embodiments, the compound wherein W is

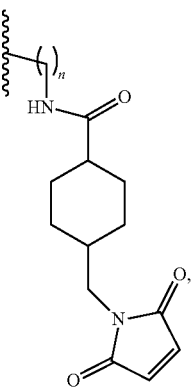

wherein n is 4-20.

17
In some embodiments, the compound wherein W is
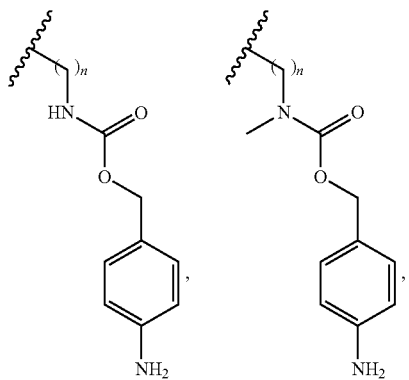
or
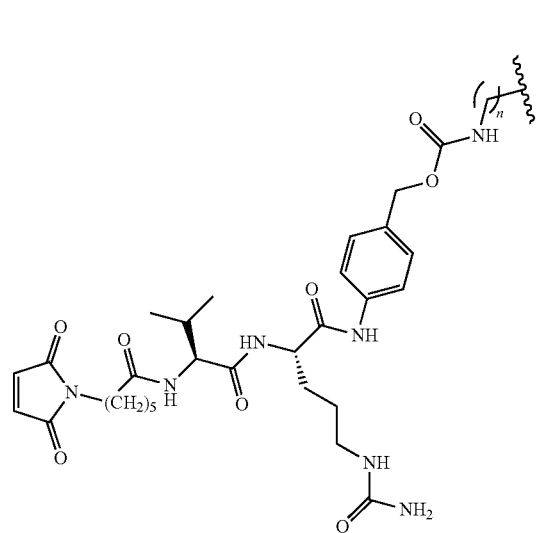
or
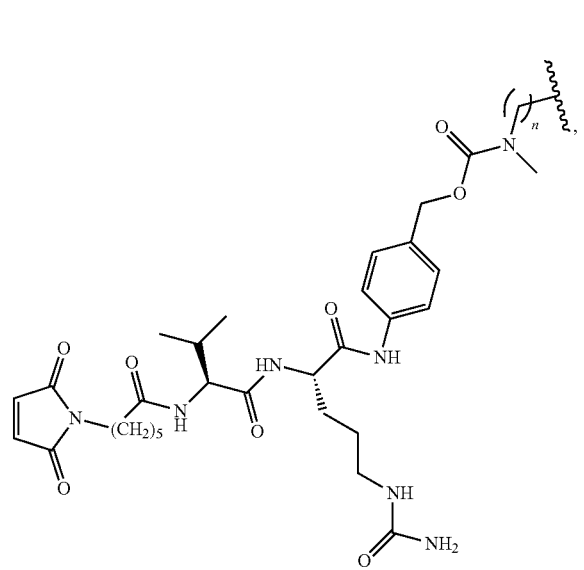
wherein n is 1-20.
18
In some embodiments, the compound wherein W is
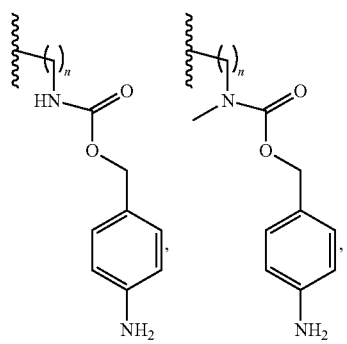
or
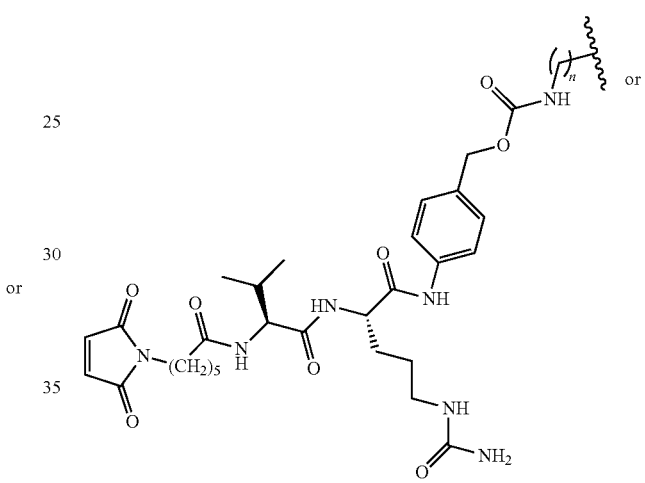
or
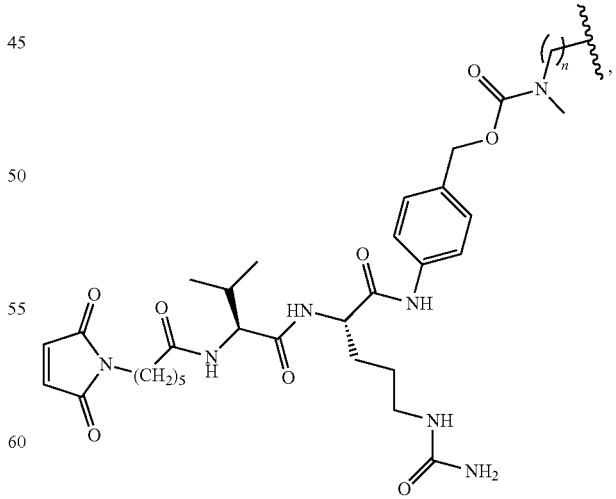
wherein n is 4-20.
In some embodiments, the compound having the structure:

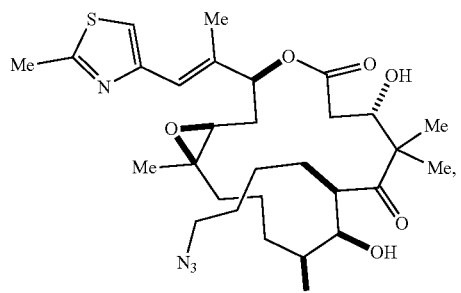
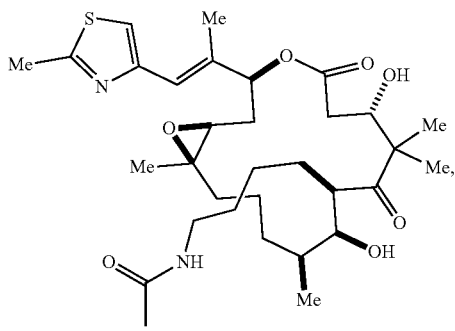
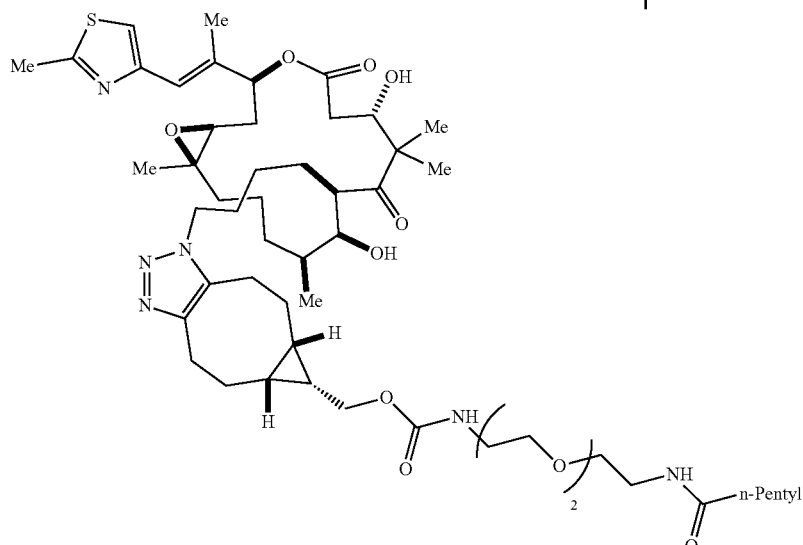

or

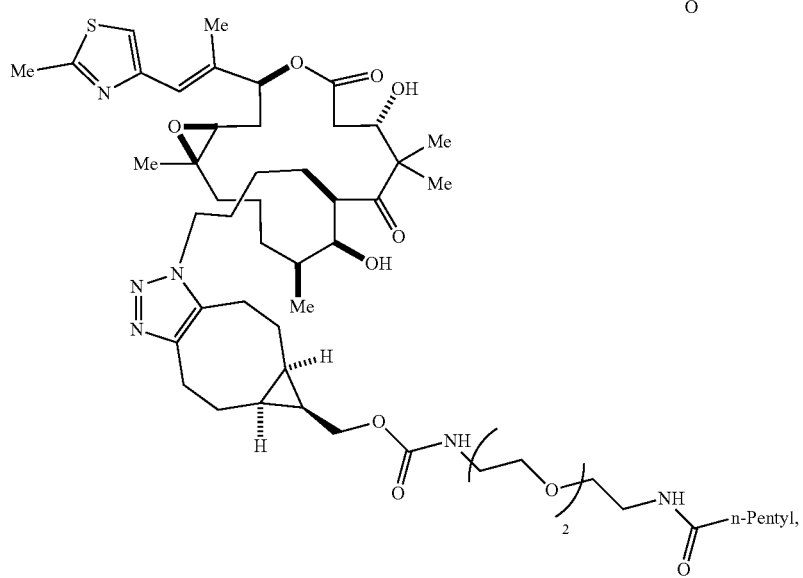

or a stereoisomer or a pharmaceutically acceptable salt or ester thereof.

In some embodiments, the compound wherein W is a chemical linker precursor,
or a stereoisomer or pharmaceutically acceptable salt or ester thereof.

In some embodiments, the compound wherein W is X—Y,
wherein
X is a chemical linker; and
Y is an antibody, folate or imaging agent, or a stereoisomer or pharmaceutically acceptable salt or ester thereof.

The present invention provides a pharmaceutical composition comprising the compound of the present invention and a pharmaceutically acceptable carrier.

In one embodiment, a composition, free of soil extract, comprising the compound of the present invention.

In one embodiment, a composition, free of soil extract, comprising at least 1 mg of the compound of the present invention. In one embodiment, a composition, free of soil extract, comprising at least 2 mg of the compound of the present invention. In some embodiments, a composition, free of soil extract, comprising at least 5 mg of the compound of the present invention. In one embodiment, a composition, free of soil extract, comprising at least 10 mg of the compound of the present invention. In one embodiment, a composition, free of soil extract, comprising at least 25 mg of the compound of the present invention. In one embodiment, a composition, free of soil extract, comprising at least 50 mg of the compound of the present invention. In one embodiment, a composition, free of soil extract, comprising at least 100 mg of the compound of the present invention.

The present invention also provides a pharmaceutical composition comprising the compound having the structure:

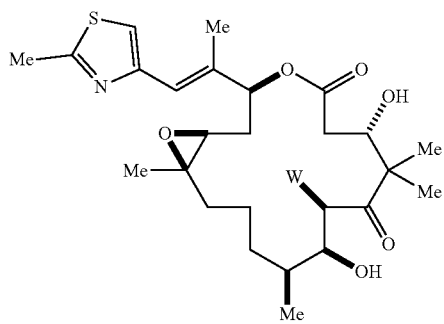

wherein
W is $C_4$-$C_{20}$ alkyl, $C_4$-$C_{20}$ alkenyl, alkynyl, alkylcycloalkyl, alkylaryl, alkylheteroaryl, alkyl-$N_3$, alkyl-SH, alkyl-OH, alkyl-$NH_2$, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$, or a chemical linker precursor,
wherein
$R_1$ is H, alkyl, alkenyl, alkynyl, cycloalkyl, aryl, heteroaryl or a polyether,
$R_2$ is H, alkyl, alkenyl, alkynyl, cycloalkyl, aryl, heteroaryl or a polyether,
$R_3$ is H, alkyl, alkenyl, alkynyl, cycloalkyl, aryl, heteroaryl or a polyether,
$R_4$ is H, $C_2$-$C_{20}$ alkyl, alkenyl, alkynyl, cycloalkyl, aryl, heteroaryl or a polyether,
or a stereoisomer or a pharmaceutically acceptable salt or ester thereof.

The present invention also includes a compound having the structure:

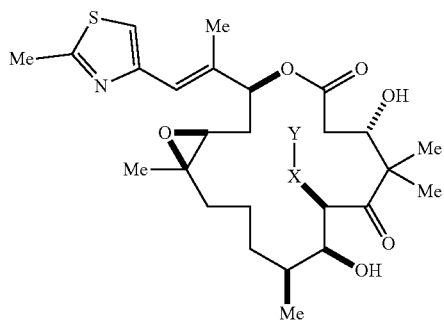

wherein
X is a chemical linker; and
Y is an antibody, folate or imaging agent,
or a stereoisomer or pharmaceutically acceptable salt or ester thereof.

In some embodiments, Y is an antibody. In some embodiments, Y is a folate. In some embodiments, Y is an imaging agent.

In some embodiments, the compound having the structure of Epothilone B wherein the C6 methyl group is replaced with an organic moiety other than H, $C_1$-$C_3$ alkyl or $C_1$-$C_3$ alkenyl.

The present invention provides a compound having the structure:

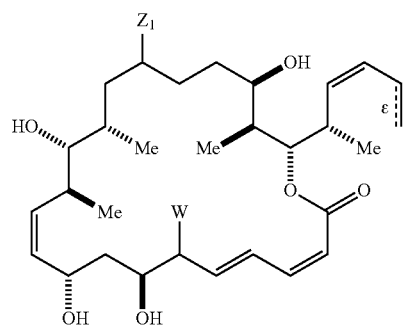

wherein W is an organic moiety other than —H, —$CH_3$,

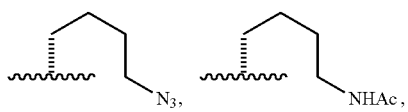

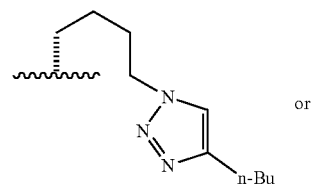

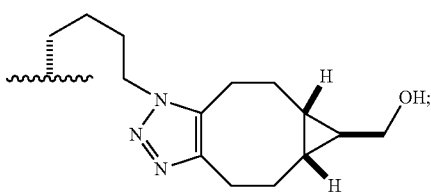

$Z_1$ is —H or —$CH_3$; and
ε is a bond and is absent or present,
or a stereoisomer or a pharmaceutically acceptable salt or ester thereof.

The present invention provides a compound having the structure:

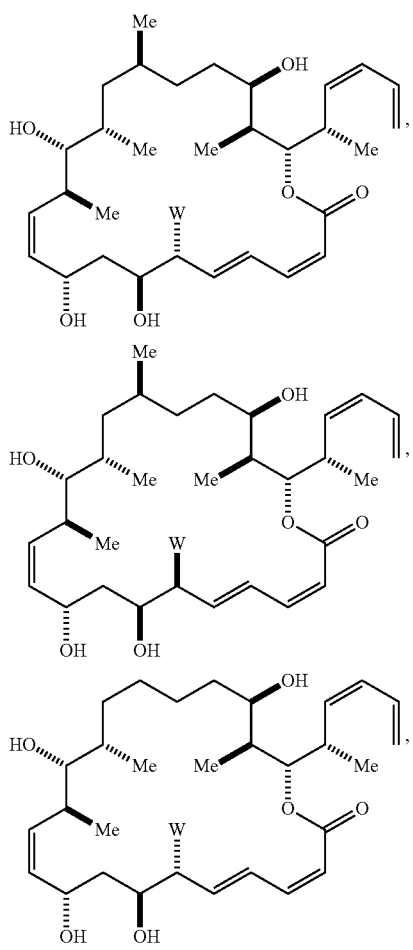
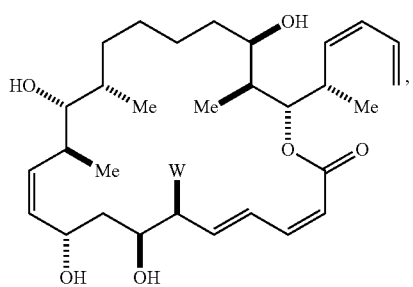
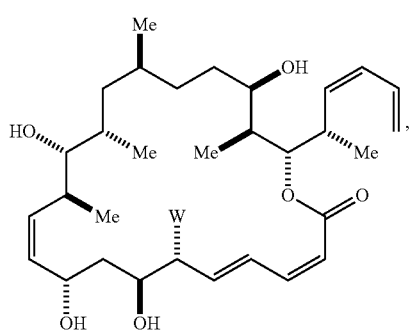
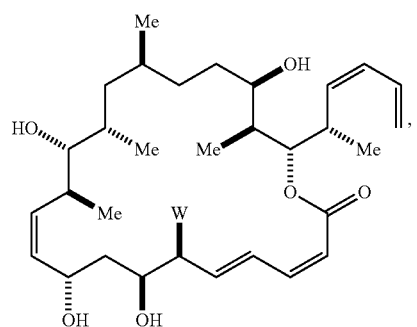
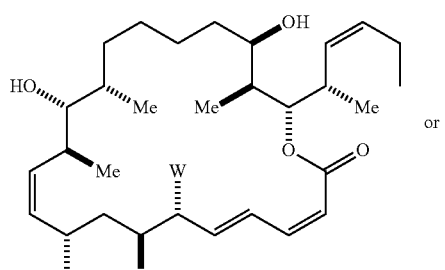
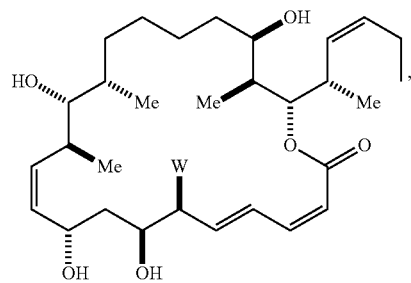
wherein W is an organic moiety other than —H, —CH$_3$,
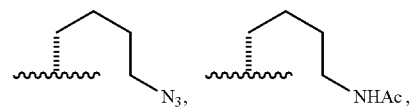
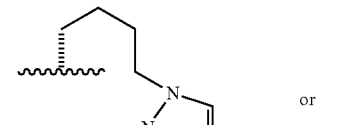
or
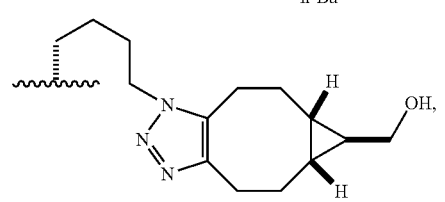
or a stereoisomer or a pharmaceutically acceptable salt or ester thereof.
The present invention provides a compound having the structure:

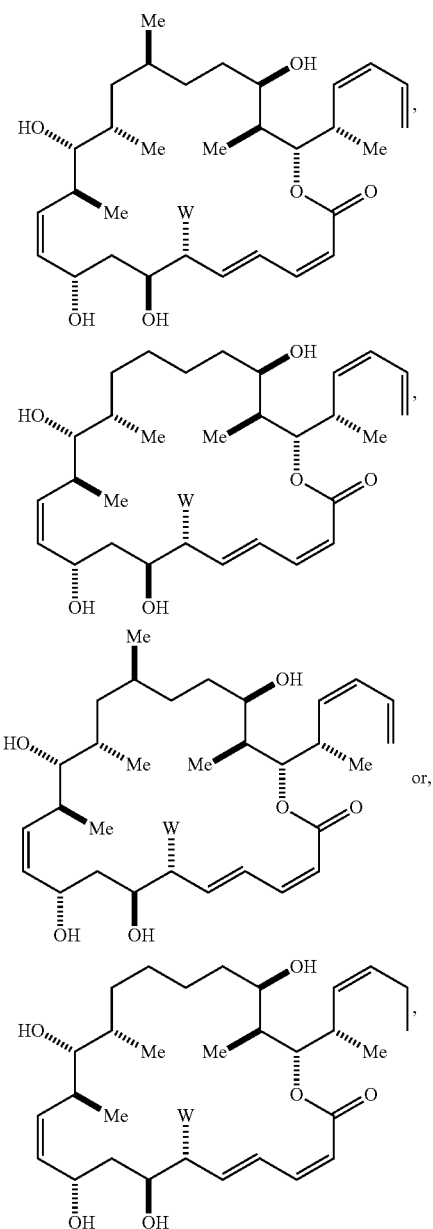

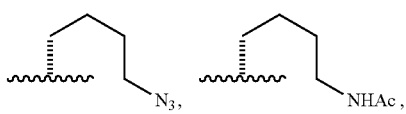

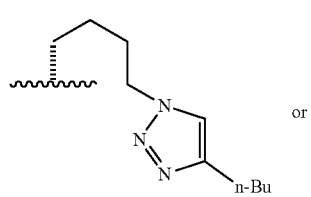

wherein W is an organic moiety other than —H, —CH₃,

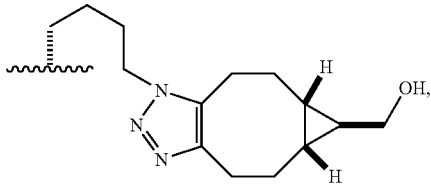

or a stereoisomer or a pharmaceutically acceptable salt or ester thereof.

The present invention provides a compound having the structure:

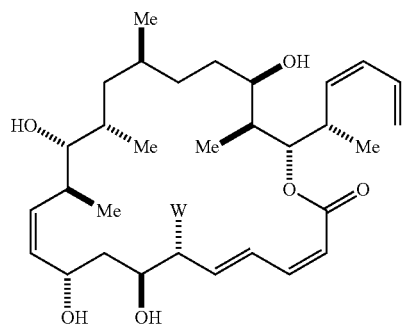

wherein W is an organic moiety other than —H, —CH₃,

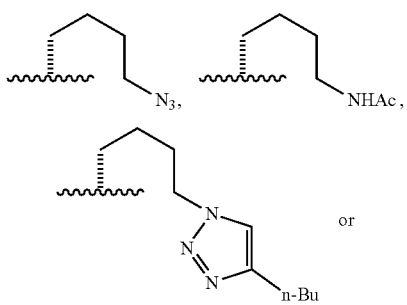

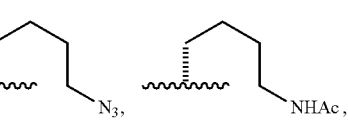

or a stereoisomer or a pharmaceutically acceptable salt or ester thereof.

In some embodiments, the compound wherein W is an organic moiety other than H, $C_1$-$C_2$ alkyl,

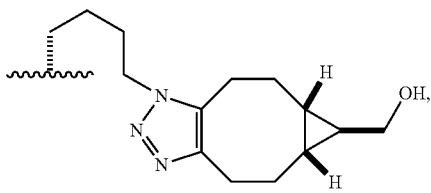

-continued

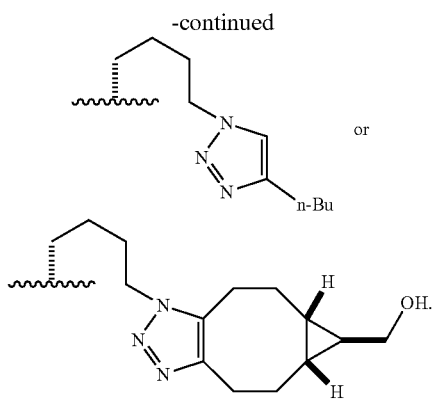

In some embodiments, the compound wherein W is an organic moiety other than H, $C_1$-$C_3$ alkyl,

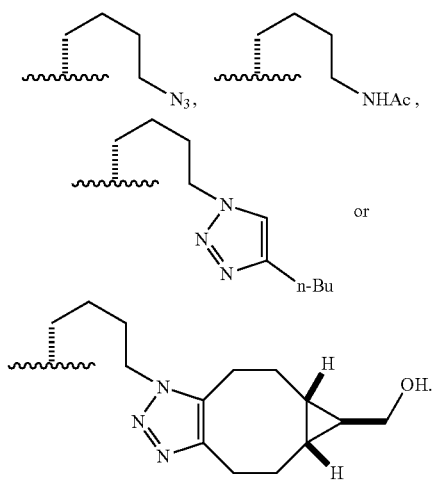

In some embodiments, the compound
wherein
W is $C_2$-$C_{20}$ alkyl, alkenyl, alkynyl, alkylcycloalkyl, alkylaryl, alkylheteroaryl, alkyl-$N_3$, alkyl-SH, alkyl-OH, alkyl-$NH_2$, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$ or alkyl-maleimide,
wherein
$R_1$ is H, alkyl, alkenyl, alkynyl, cycloalkyl, aryl, heteroaryl or a polyether,
$R_2$ is H, alkyl, alkenyl, alkynyl, cycloalkyl, aryl, heteroaryl or a polyether,
$R_3$ is H, alkyl, alkenyl, alkynyl, cycloalkyl, aryl, heteroaryl or a polyether,
$R_4$ is H, alkyl, alkenyl, alkynyl, cycloalkyl, aryl, heteroaryl or a polyether, and
W is other than

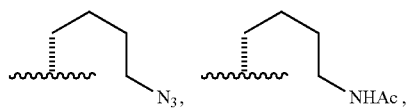

-continued

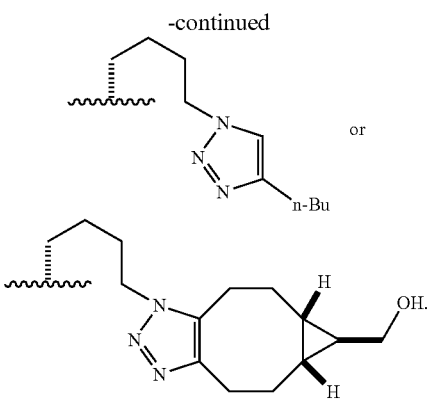

In some embodiments, the compound
wherein W is $C_2$-$C_{20}$ alkyl, alkenyl, alkynyl, alkylaryl, —$(CH_2)_n$-heteroaryl, —$(CH_2)_n$—$N_3$, alkyl-SH, alkyl-OH, alkyl-$NH_2$, alkyl-NH—$R_1$, alkyl-$NR_2R_3$, alkyl-$OR_1$, alkyl-OC(O)—$R_1$, —$(CH_2)_n$—NHAc, —$(CH_2)_n$—NHC(O)—$R_1$, -alkyl-NHC(O)—$R_4$, alkyl-OC(O)—$OR_1$, alkyl-NHC(O)—$NHR_1$, alkyl-NHC(S)—$NHR_1$ or alkyl-maleimide,
wherein
$R_1$ is H, alkyl, alkenyl, alkynyl, cycloalkyl, aryl, heteroaryl or a polyether,
$R_2$ is H, alkyl, alkenyl, alkynyl, cycloalkyl, aryl, heteroaryl or a polyether,
$R_3$ is H, alkyl, alkenyl, alkynyl, cycloalkyl, aryl, heteroaryl or a polyether,
$R_4$ is H, alkyl, alkenyl, alkynyl, cycloalkyl, aryl, heteroaryl or a polyether, and
n is 1-3 or 5-20.
In some embodiments, the compound
wherein
W is $C_4$-$C_{20}$ alkyl, $C_4$-$C_{20}$ alkenyl, alkynyl, alkylcycloalkyl, alkylaryl, alkylheteroaryl, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$,
wherein
$R_1$ is alkyl, alkenyl, alkynyl, cycloalkyl, aryl, heteroaryl or a polyether,
$R_2$ is alkyl, alkenyl, alkynyl, cycloalkyl, aryl, heteroaryl or a polyether,
$R_3$ is H, alkyl, alkenyl, alkynyl, cycloalkyl, aryl, heteroaryl or a polyether,
$R_4$ is H, alkyl, alkenyl, alkynyl, cycloalkyl, aryl, heteroaryl or a polyether.
In some embodiments, the compound
wherein W is alkyl-$N_3$, alkyl-SH, alkyl-OH, alkyl-$NH_2$, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$ or alkyl-maleimide,
$R_1$ is alkyl-$N_3$, alkyl-SH, alkyl-OH, alkyl-$NH_2$, or alkyl-maleimide
$R_2$ is alkyl-$N_3$, alkyl-SH, alkyl-OH, alkyl-$NH_2$, or alkyl-maleimide
$R_3$ is alkyl-$N_3$, alkyl-SH, alkyl-OH, alkyl-$NH_2$, or alkyl-maleimide, and
$R_4$ is alkyl-$N_3$, alkyl-SH, alkyl-OH, alkyl-$NH_2$ or alkyl-maleimide.

In some embodiments, the compound wherein W is —(CH$_2$)$_n$—N$_3$, wherein n is 1-3 or 5-20.

In some embodiments, the compound wherein W is —(CH$_2$)$_n$—NHAc, wherein n is 1-3 or 5-20.

In some embodiments, the compound wherein W is

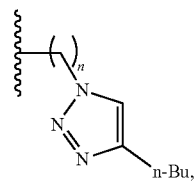

wherein n is 1-3 or 5-20.

9 In some embodiments, the compound wherein W is

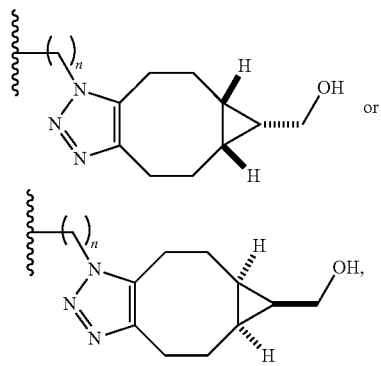

wherein n is 1-3 or 5-20.

In some embodiments, the compound wherein W is

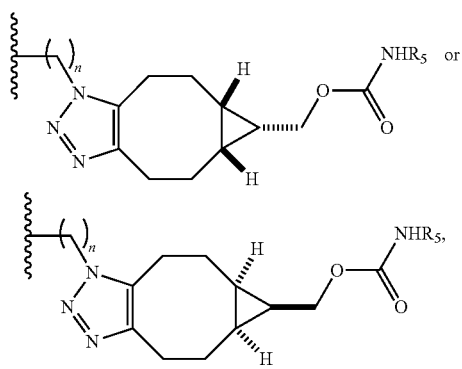

wherein n is 1-20; and
R$_5$ is H, alkyl, alkenyl, alkynyl, cycloalkyl, aryl, heteroaryl or a polyether.

In some embodiments, the compound wherein W is

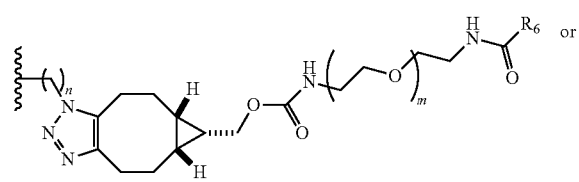

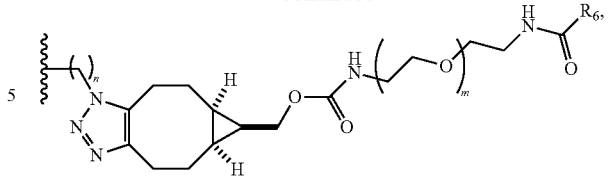

wherein n is 1-20;
m is 1-10; and
R$_6$ is H, alkyl, alkenyl, alkynyl, cycloalkyl, aryl, heteroaryl or a polyether.

In some embodiments, the compound wherein W is

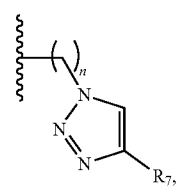

wherein n is 1-20; and
R$_7$ is H, C$_1$-C$_3$ alkyl, C$_5$-C$_{20}$ alkyl, alkenyl, alkynyl, cycloalkyl, aryl, heteroaryl or a polyether.

In some embodiments, the compound wherein W is

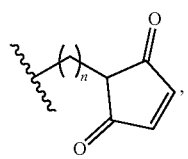

wherein n is 1-20.

In some embodiments, the compound wherein W is

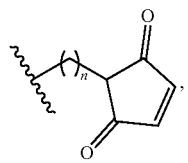

wherein n is 4-20.

In some embodiments, the compound wherein W is

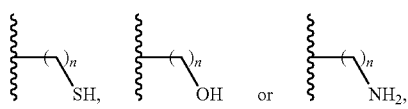

wherein n is 1-20.

In some embodiments, the compound wherein W is

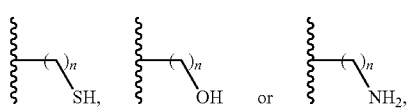

wherein n is 4-20.

In some embodiments, the compound wherein W is
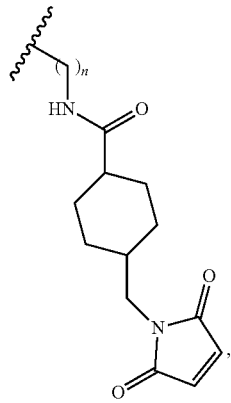
wherein n is 1-20.
In some embodiments, the compound wherein W is
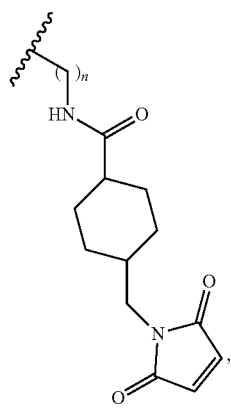
wherein n is 4-20.
In some embodiments, the compound wherein W is
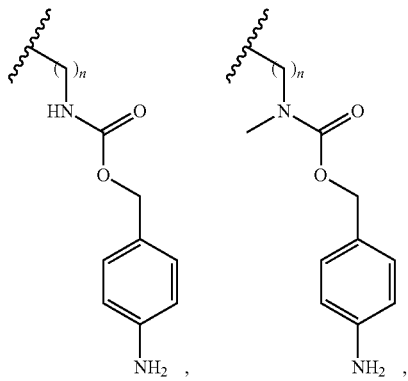
In some embodiments, the compound wherein W is
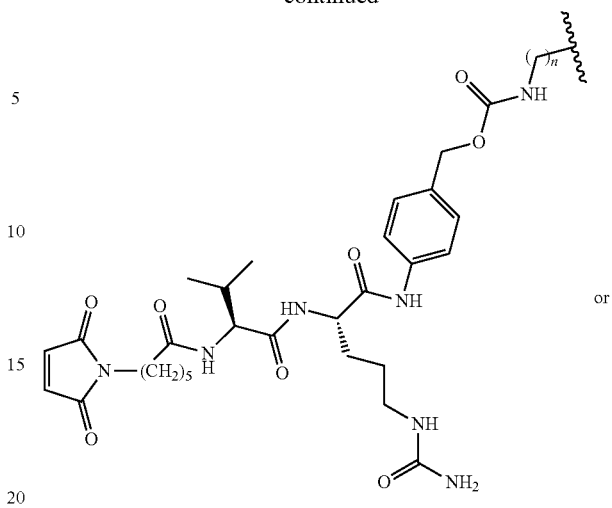
or
wherein n is 1-20.
In some embodiments, the compound wherein W is
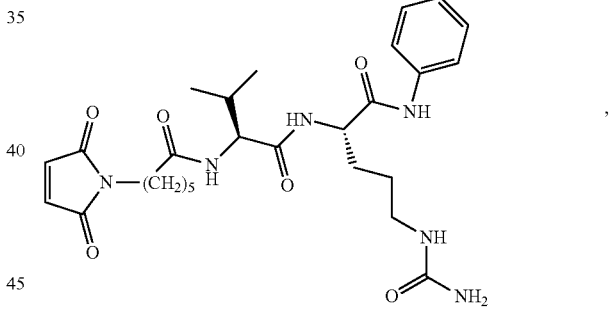
wherein n is 1-20.
In some embodiments, the compound wherein W is
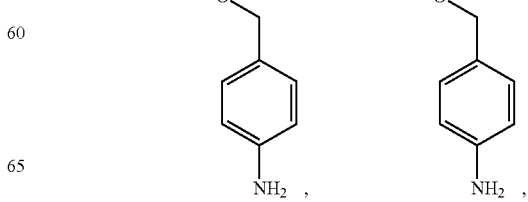

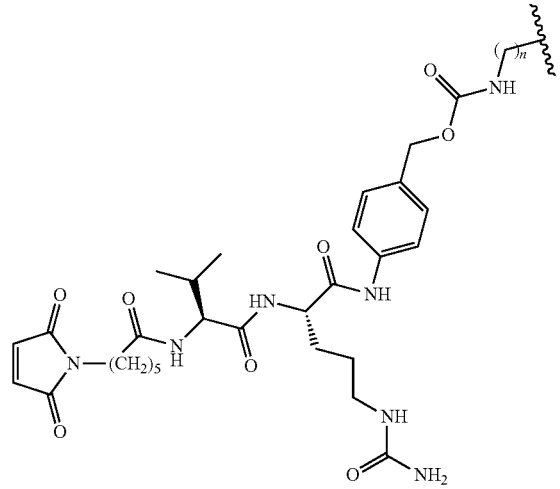
or
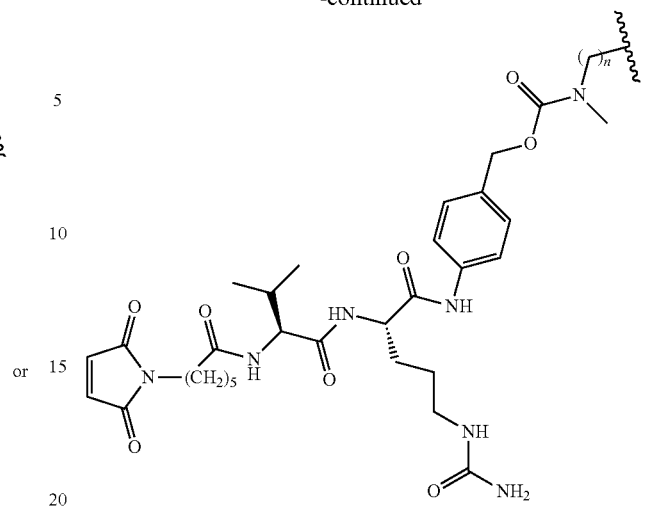
wherein n is 4-20.
In some embodiments, the compound having the structure:
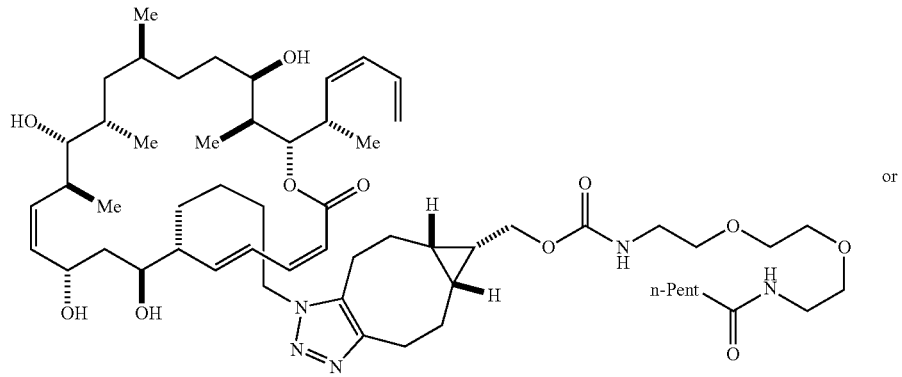
or
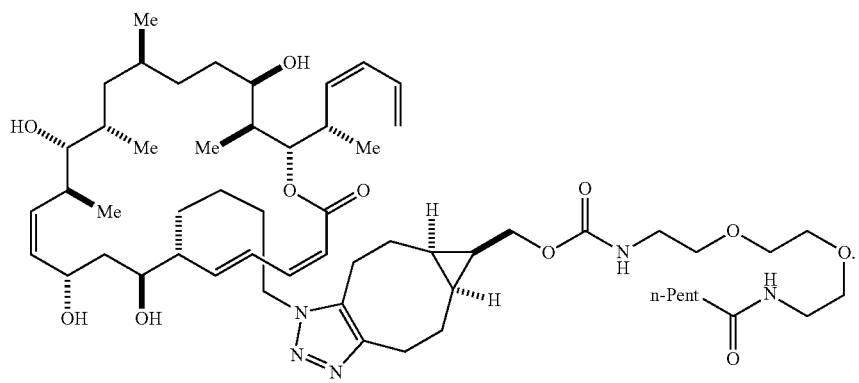

In some embodiments, the compound wherein

W is a chemical linker precursor.

In some embodiments, the compound wherein W is X—Y, wherein

X is a chemical linker; and

Y is an antibody, folate or imaging agent.

The present invention provides a pharmaceutical composition comprising the compound of the present invention and a pharmaceutically acceptable carrier.

In one embodiment, a composition, free of sponge extract, comprising the compound of the present invention.

In one embodiment, a composition, free of sponge extract, comprising at least 1 mg of the compound of the present invention. In one embodiment, a composition, free of sponge extract, comprising at least 2 mg of the compound of the present invention. In some embodiments, a composition, free of sponge extract, comprising at least 5 mg of the compound of the present invention. In one embodiment, a composition, free of sponge extract, comprising at least 10 mg of the compound of the present invention. In one embodiment, a composition, free of sponge extract, comprising at least 25 mg of the compound of the present invention. In one embodiment, a composition, free of sponge extract, comprising at least 50 mg of the compound of the present invention. In one embodiment, a composition, free of sponge extract, comprising at least 100 mg of the compound of the present invention.

The present invention also provides a pharmaceutical composition comprising the compound having the structure:

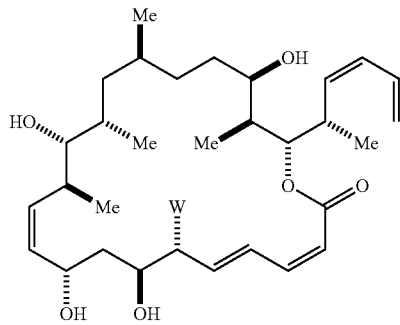

wherein

W is $C_2$-$C_{20}$ alkyl, alkenyl, alkynyl, alkylcycloalkyl, alkylaryl, alkylheteroaryl, alkyl-$N_3$, alkyl-SH, alkyl-OH, alkyl-$NH_2$, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$, or a chemical linker precursor, wherein $R_1$ is H, alkyl, alkenyl, alkynyl, cycloalkyl, aryl, heteroaryl or a polyether, $R_2$ is H, alkyl, alkenyl, alkynyl, cycloalkyl, aryl, heteroaryl or a polyether, $R_3$ is H, alkyl, alkenyl, alkynyl, cycloalkyl, aryl, heteroaryl or a polyether, $R_4$ is H, $C_2$-$C_{20}$ alkyl, alkenyl, alkynyl, cycloalkyl, aryl, heteroaryl or a polyether, and or a stereoisomer or a pharmaceutically acceptable salt or ester thereof, and a pharmaceutically acceptable carrier.

The present invention also includes a compound having the structure:

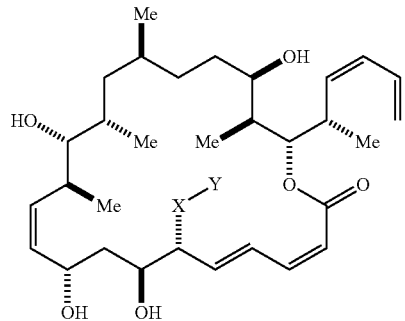

wherein

X is a chemical linker; and

Y is an antibody, folate or imaging agent, or a stereoisomer or pharmaceutically acceptable salt or ester thereof.

In some embodiments, Y is an antibody. In some embodiments, Y is a folate. In some embodiments, Y is an imaging agent.

In some embodiments, the compound having the structure of dictyostatin wherein the C6 methyl group is replaced with an organic moiety other than —H, —$CH_3$,

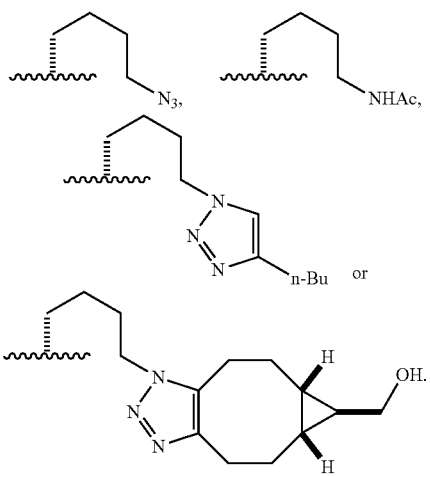

In some embodiments, the compound of the present invention wherein n is an integer from 1-20. In some embodiments, the compound of the present invention wherein n is an integer from 2-20. In some embodiments, the compound of the present invention wherein n is an integer from 1-30. In some embodiments, the compound of the present invention wherein n is an integer from 2-30. In some embodiments, the compound of the present invention wherein n is an integer from 1-40.

In some embodiments, the compound of the present invention wherein n is an integer from 2-40. In some embodiments, the compound of the present invention wherein n is an integer from 1-50. In some embodiments, the compound of the present invention wherein n is an integer from 2-50. In some embodiments, the compound of the present invention wherein n is an integer from 1-3. In some embodiments, the compound of the present invention wherein n is 5-20. In some embodiments, the compound of the present invention wherein n is 4.

In some embodiments, the compound of the present invention wherein n is an integer from 4-20. In some embodiments, the compound of the present invention wherein n is an integer from 5-20. In some embodiments, the compound of the present invention wherein n is an integer from 6-20.

In some embodiments, the compound of the present invention wherein n is an integer from 4-30. In some embodiments, the compound of the present invention wherein n is an integer from 5-30. In some embodiments, the compound of the present invention wherein n is an integer from 6-30.

In some embodiments, the compound of the present invention wherein n is an integer from 4-40. In some embodiments, the compound of the present invention wherein n is an integer from 5-40. In some embodiments, the compound of the present invention wherein n is an integer from 6-40.

In some embodiments, the compound of the present invention wherein n is an integer from 4-50. In some embodiments, the compound of the present invention wherein n is an integer from 5-50. In some embodiments, the compound of the present invention wherein n is an integer from 6-50.

In some embodiments, a composition, free of soil extract, comprising the compound of the present invention. Embodiments of the foregoing composition free of soil extract include each of the embodiments of the compounds described hereinabove.

In some embodiments, a composition, free of sponge extract, comprising the compound of the present invention. Embodiments of the foregoing composition free of sponge extract include each of the embodiments of the compounds described hereinabove.

In some embodiments, a pharmaceutical composition comprising the compound of the present invention and a pharmaceutically acceptable carrier.

In some embodiments, a method for reducing one or more symptoms of disease in a subject, comprising administering an effective amount of the compound of the present invention or the composition of the present invention to the subject so as to treat the disease in the subject.

In some embodiments, a method wherein the disease is cancer. In some embodiments, a method for inhibiting growth of a tumor comprising contacting the tumor with the compound of the present invention or the composition of the present invention. In some embodiments, a method for reducing the size of a tumor comprising contacting the tumor with the compound of the present invention or the composition of the present invention In some embodiments, the invention provides a method of reducing one or more symptoms of any disease that involves carcinomas including but not limited to lung cancer, breast cancer, prostate cancer, cervical cancer, pancreatic cancer, colon cancer, ovarian cancer; stomach cancer, esophagus cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (such as synovium cancer), glioblastoma, lymphoma, and leukemia. Malignant neoplasms are further exemplified by sarcomas (such as osteosarcoma and Kaposi's sarcoma).

In some embodiments, the invention provides an antibody-drug conjugate (ADC) wherein the compound of the present invention is linked through a chemical linker to an antibody. Antibody-drug conjugate (ADC) utilize the specificity of the antibody to deliver drugs selectively to antigen-expressing cancer cells (see, e.g., Perez, H. L. et al. 2013; Chari, R. V. J. et al. 2014; Carter, P. J. et al. 2008). The compound may also be linked to a folate or imaging agent.

The compounds described herein are C6 analogs and C6-epi analogs of epothilone B (Pfeiffer, B. et al. 2012), desoxyepothilone B (Chou, T. et al. 1998), KOS-1803 (Chou, T. et al. 2008), ZK-EPO (Klar, U. et al. 2006), sagopilone (Klar, U. et al. 2012) or ixabepilone (Aghajanian, C. et al. 2007).

The epothilone B C6 analogs 19-21 were modified to incorporate a linker moiety capable of linking, for example, to an antibody, folate or imaging agent, while maintaining or improving activity of the parent compound. The C6 analogs 19-21 show that the epothilones tolerate substitution at the C6 position while maintaining or improving activity. The other epothilone compounds described herein have similar activity to 19-21.

The advantages of the C6 epothilone analogs described herein are that they contain a C6 linker moiety capable of linking, for example, to an antibody or folate, while maintaining or improving activity. Such antibodies or folates target only cancer cells and deliver the epothilone compound only to the cancer cells while sparing healthy cells.

The compounds described herein are C6 analogs and C6-epi analogs of dictyostatin (Eiseman, J. L. et al. 2008), 25,26-dihydrodictyostatin (Jimenez, M. et al. 2011), 16-desmethyldictyostatin (Paterson, I. et al. 2007) or 16-desmethyl-25,26-dihydrodictyostatin (Zhu, W. et al. 2010).

The dictyostatin analogs 1, 26 and 27 were modified to incorporate a linker moiety capable of linking, for example, to an antibody, folate or imaging agent, while maintaining activity of the parent compound.

The C6 analogs 1, 26 and 27 show that the dictyostatins tolerate substitution at the C6 position while maintaining activity. The other compounds described herein have similar activity to 1, 26 and 27.

The advantages of the C6 dictyostatin analogs described herein are that they contain a C6 linker moiety capable of linking, for example, to an antibody or folate, while maintaining activity. Such antibodies or folates target only cancer cells and deliver the dictyostatin compound only to the cancer cells while sparing healthy cells.

As used herein, "chemical linker precursor" is any chemical linker that is not yet bound to an antibody, folate or imaging agent, but that includes a functional group capable of binding to an antibody. An example of a chemical linker precursor is a maleimide group.

As used herein, "chemical linker" is any organic moiety that links a compound with an antibody, folate or imaging agent. The chemical linker can both react with groups on an antibody, folate or imaging agent and on a compound or drug to link the structures together. It is known in the art how to prepare suitable linkers with suitable groups and react linkers with groups to be linked, as well as to functionalize both the linkers and groups to be linked to cause the desired linkage to occur. The chemical linker may be cleavable non-cleavable or releasable linker. The cleavable linker of the conjugate can be cleaved from the compound by, for example, enzymatic cleavage in vivo, to release the compound of the present invention. The ADC may bind to a cell and become internalized prior to the drug being enzymatically released from the antibody to become activated inside the cell. Examples of the chemical linker include, but are not limited to, peptide linkers, self-immolative linkers, disulfide linkers, thioether linkers, hydrazine linkers, maleimide linkers, hydrophilic linkers or other linkers that are generally known in the art. The chemical linker may also link the compound with a drug.

Sulfhydryl groups are useful targets for protein conjugation. Sulfhydryls, also called thiols, exist in proteins in the side-chain of cysteine (Cys, C) amino acids and are available for reaction with thiol-reactive compounds. Sulfhydryls are present in most proteins but are not as numerous as primary amines; thus, conjugating via sulfhydryl groups is more selective. Sulfhydryl-reactive chemical groups that may serve as chemical linker precursors in the compounds of the present invention include, but are not limited to, haloacetyls, maleimides, aziridines, acryloyls, arylating agents, vinylsulfones, pyridyl disulfides, TNB-thiols and disulfide reducing agents. Most of these groups conjugate to sulfhydryls by either alkylation (usually the formation of a thioether bond) or disulfide exchange (formation of a disulfide bond). Maleimide linker precursors reacts specifically with sulfhydryl groups resulting in the formation of a stable thioether linkage.

The term "cleaveable linker" is intended to mean a moiety that is unstable in vivo. The linker allows for activation of the therapeutic agent by cleaving the agent from the rest of the conjugate. The linker may be cleaved in vivo by the biological environment. The cleavage may come from any process without limitation, e.g., enzymatic, reductive, pH, etc. The cleaveable group may be selected so that activation occurs at the desired site of action, which can be a site in or near the target cells (e.g., carcinoma cells).

The term "self-immolative linker" refers to a bifunctional chemical moiety that is capable of covalently linking to two chemical moieties. The self-immolative linker cleaves spontaneously from the second moiety after the bond to first moiety is broken, thereby releasing both moieties.

The cleavable linker or self-immolative linker may be a "traceless" linker because the final active epothilone or dictyostatin compound reveals no trace of the linker to the antibody or folate.

Examples of chemical linkers include but are not limited to, the stable thioether linker MCC (4-[N-maleimidomethyl]cyclohexane-1-carboxylate) found in KADCYLA® and the cathepsin cleavable linker (valine-citrulline) found in ADCETRIS® (see Sochaj, A. M. et al. 2015).

In some embodiments, Y is an antibody having specificity for at least one type of tumor or cancer cell. In some embodiments, X is a cleavable linker. In some embodiments, X is a cleavable linker that is cleavable in the presence of a tumor. In some embodiments, X is a cleavable linker that is cleavable in the presence of a cancer cell.

In some embodiments, X is a cleavable linker comprising an amide, thiourea, thioether, disulfide, polyether amide, or a triazole.

In some embodiments, X is a peptide linker, maleimidocaproyl linker, a mercaptoacetamidocaproyl linker, cathepsin cleavable linker, a succinimidyl 4-(N-maleimidomethyl) cyclohexane-1-carboxylate linker, a maleimide linker, disulfide linker, thioether linker, hydrazine linker or hydrazine linker.

In some embodiments, X is a hydrazine, disulfide, peptide or thioether linker.

The chemical linker may include an attachment group $A_1$, a linker group $A_2$ and/or a spacer group $A_3$.

The term "antibody" as used herein is defined broadly as a protein that characteristically immunoreacts with an epitope (antigenic determinant) of an antigen. As is known in the art, the basic structural unit of an antibody is composed of two identical heavy chains and two identical light chains, in which each heavy and light chain consists of amino terminal variable regions and carboxy terminal constant regions. The antibodies of the present invention include, but are not limited to, polyclonal antibodies, monoclonal antibodies (mAbs), chimeric antibodies, CDR-grafted antibodies, humanized antibodies, human antibodies, catalytic antibodies, multispecific antibodies, as well as fragments, regions or derivatives thereof provided by known techniques, including, for example, enzymatic cleavage, peptide synthesis or recombinant techniques. Various commercially available antibodies may be employed with the methods of the present invention.

As used herein, "monoclonal antibody" means an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants, each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature* 256:495-97 (1975), or may be made by recombinant DNA methods (see, e.g., U.S. Pat. No. 4,816,567). The monoclonal antibodies may also be isolated from phage display libraries using the techniques described, for example, in Clackson et al., *Nature* 352:624-28 (1991) and Marks et al., *J. Mol. Biol.* 222(3): 581-97 (1991).

The term "hybridoma" or "hybridoma cell line" refers to a cell line derived by cell fusion, or somatic cell hybridization, between a normal lymphocyte and an immortalized lymphocyte tumor line. In particular, B cell hybridomas are created by fusion of normal B cells of defined antigen specificity with a myeloma cell line, to yield immortal cell lines that produce monoclonal antibodies. In general, techniques for producing human B cell hybridomas, are well known in the art [Kozbor et al., *Immunol. Today* 4:72 (1983); Cole et al., in *Monoclonal Antibodies and Cancer Therapy*, Alan R. Liss, Inc. 77-96 (1985)].

The term "epitope" refers to a portion of a molecule (the antigen) that is capable of being bound by a binding agent, e.g., an antibody, at one or more of the binding agent's antigen binding regions. Epitopes usually consist of specific three-dimensional structural characteristics, as well as specific charge characteristics.

In some embodiments, the invention provides a drug conjugate wherein the compound of the present invention is linked through a chemical linker to a polymer, lipid, albumin, reporter molecule, imaging agent, vitamin, folate or folic acid.

Imaging agents include, but are not limited to, fluorogenic probes, optical probes, radiolabeled probes, dyes, contrast agents, radioactive contrast agents, MRI contrast agents, PET imaging agents, and SPECT imaging agents. Imaging agents include, but are not limited to, any compositions useful for imaging cancer cells.

Vitamin folic acid (FA) displays high affinity for the folate receptor (FR), a glycosylphosphatidyinositol-linked membrane protein that captures its ligands from the extracellular milieu and transports them inside the cell via a nondestructive, recycling endosomal pathway. Since FR's expression is largely absent from normal tissues, FR is a recognized tumor biomarker (Vlahov, I. R. et al. 2012).

"Free of soil extract" with regard to a composition as used herein means that the composition is absent any amount of soil material or epothilione B containing-soil material. Thus only synthetically produced compounds and compositions are free of soil extract. Any compound or compositions isolated from soil would always contain at least some trace amount of soil material. In some embodiments, the composition of the present invention is free of *Sorangium cellulsum* extract. In some embodiments, the composition of the present invention is free of *Sorangium* extract.

"Free of sponge extract" with regard to a composition as used herein means that the composition is absent any amount of sponge material or dictyostatin containing-sponge material. Thus only synthetically produced compounds and compositions are free of sponge extract. Any compound or compositions isolated from a sponge would always contain at least some trace amount of sponge material. In some embodiments, the composition of the present invention is free of *Spongia* sp. extract. In some embodiments, the composition of the present invention is free of Corallistidae sp. extract Except where otherwise specified, when the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column. Stereoisomers of the compounds of the present invention include enantiomers, diastereomers, and E-Z isomers.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethyl-benzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

In the compounds of the present invention, the substituents may be substituted or unsubstituted, unless specifically defined otherwise.

In the compounds of the present invention, alkyl, alkenyl, alkynyl, alkylaryl, heteroalkyl, cycloalklyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl. These groups may be further substituted by replacing one or more hydrogen atoms with a chemical linker or chemical linker precursor.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, and hexyl. Unless otherwise specified contains one to ten carbons.

Alkyl groups can be unsubstituted or substituted with one or more substituents, including but not limited to halogen, alkoxy, alkylthio, trifluoromethyl, difluoromethyl, methoxy, and hydroxyl.

In some embodiments, W is $C_2$-$C_{20}$ alkyl. In some embodiments, W is $C_2$-$C_{30}$ alkyl. In some embodiments, W is $C_2$-$C_{30}$ alkyl. In some embodiments, W is $C_2$-$C_{40}$ alkyl. In some embodiments, W is $C_2$-$C_{50}$ alkyl.

In some embodiments, "alkyl" is $C_2$-$C_{20}$ alkyl. In some embodiments, "alkyl" is $C_2$-$C_{30}$ alkyl. In some embodiments, "alkyl" is $C_2$-$C_{30}$ alkyl. In some embodiments, W is $C_2$-$C_{40}$ alkyl. In some embodiments, "alkyl" is $C_2$-$C_{50}$ alkyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

As used herein, "heteroalkyl" includes both branched and straight-chain saturated aliphatic hydrocarbon groups having at least 1 heteroatom within the chain or branch.

As used herein, "cycloalkyl" includes cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "heterocycloalkyl" is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains nitrogen, it is understood that the corresponding N-oxides thereof are also encompassed by this definition.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include but are not limited to: phenyl, p-toluenyl (4-methylphenyl), naphthyl, tetrahydro-naphthyl, indanyl, phenanthryl, anthryl or acenaphthyl. In cases where the aryl substituent is bicyclic and one ring is non-aromatic, it is understood that attachment is via the aromatic ring.

The term "alkylaryl" refers to alkyl groups as described above wherein one or more bonds to hydrogen contained therein are replaced by a bond to an aryl group as described above. It is understood that an "alkylaryl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl" as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include but are not limited to phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "ester" is intended to a mean an organic compound containing the R—O—CO—R' group.

The term "amide" is intended to a mean an organic compound containing the R—CO—NH—R', R—CO—NH—R' or R—CO—NR'R" group.

As used herein, "monocycle" includes any stable polycyclic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polycyclic carbon ring of up to 10 atoms that is fused to a polycyclic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

Another aspect of the invention comprises a compound used in the method of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropyl-methacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

General Information. All reactions were carried out under an atmosphere of nitrogen in flame-dried glassware with magnetic stirring unless otherwise indicated. Degassed solvents were purified by passage through an activated alumina column. Thin-layer chromatography (TLC) was carried out on glass-backed silica gel XHL TLC plates (250 µm) from Sorbent Technologies; visualization by UV light, p-anisaldehyde stain, phosphomolybdic acid stain, or potassium permanganate ($KMnO_4$) stain. Gas chromatographic analyses were performed on a Hewlett-Packard 6890 Series Gas Chromatograph equipped with a capillary split-splitless inlet and flame ionization detector with electronic pneumatics control using a Supelco ß-Dex 325 (30 m×0.25 mm) capillary GLC column. $^1H$ NMR spectra were recorded on a Bruker DPX-400 (400 MHz) or a Bruker Avance III 500 (500 MHz) spectrometer and are reported in ppm from $CDCl_3$ internal standard (7.26 ppm). Data are reported as follows: (bs=broad singlet, s=singlet, d=doublet, t=triplet, q=quartet, quin=quintet, sep=septet, m=multiplet, dd=doublet of doublets, ddd=doublet of doublet of doublets; coupling constant(s) in Hz; integration). Proton decoupled $^{13}C$ NMR spectra were recorded on a Bruker Avance III 500 (125 MHz) spectrometer and are reported in ppm from $CDCl_3$ internal standard (77.16 ppm). Infrared spectra were recorded on a Perkin-Elmer Spectrum Two (Diamond ATR) IR spectrometer. Optical rotations were recorded on a Jasco DIP-1000 digital polarimeter.

Example 1. Epothilone B Analogs $C_1$-$C_9$ Fragment Synthesis

The following synthesis was used to access C6 methyl derivatives of the C1-C9 epothilone fragment. The linker group was installed by utilizing a substituted alkyne in place of propyne (in synthesis of epo B) for the epoxide opening step (Scheme 1). The required stereochemistry for this C6 position would be set using the "aprotic" Tamao oxidation conditions.

Scheme 1.

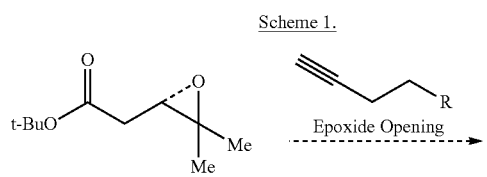

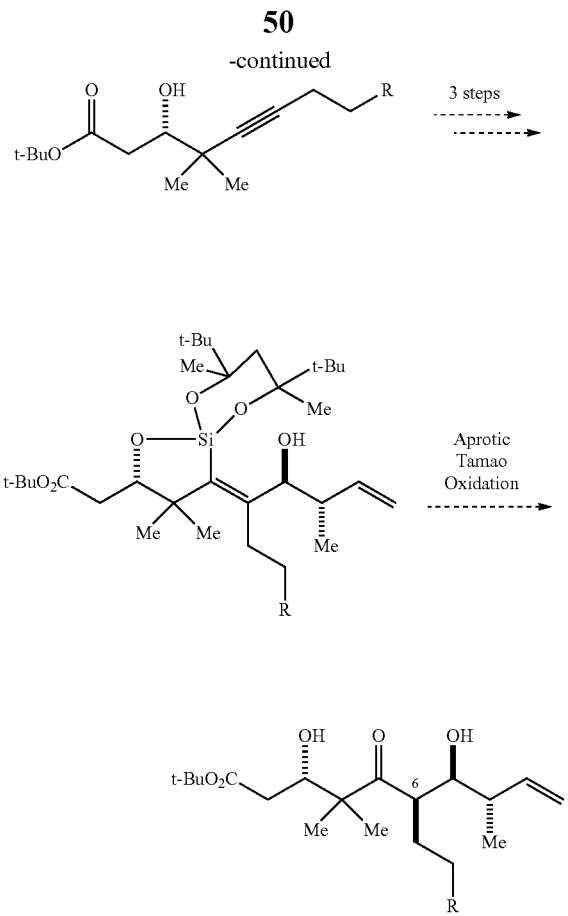

In choosing a linker group to install, it was decided to initially target a carbon chain with a terminal chloride, which could later be converted to an azide. With an azide at the end of the linker, the potential existed for use of either a click reaction (Dommerholt, J. et al. 2010; Hein, J. E. et al. 2010) or traceless Staudinger ligation (Soellner, M. B. et al. 2006) for covalent attachment to a longer tether.

Putting this approach into practice, it was found that the epoxide-opening step proceeded smoothly using chloroalkyne 2 to afford 3 in 84% yield. Silylation with chlorosilane 4 followed by rhodium-catalyzed silylformylation provided 6, as expected. However, crotylation with reagent 7 exhibited decreased rate and selectivity, providing a 3.5:1 mixture of desired 1,5-anti-diols with 1,5-syn-diol. After removing the undesired 1,5-syn-diol product by chromatography, 8 was isolated in 37% yield over 3 steps from 3 in a 2:1 mixture of diastereomers at silicon.

Scheme 2.

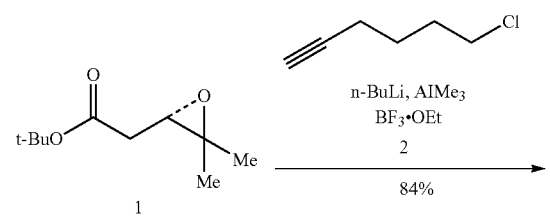

-continued
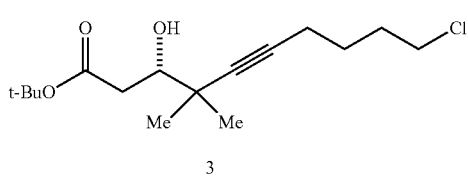
3
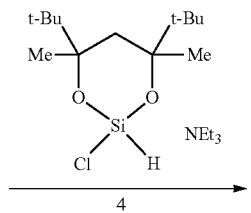
4
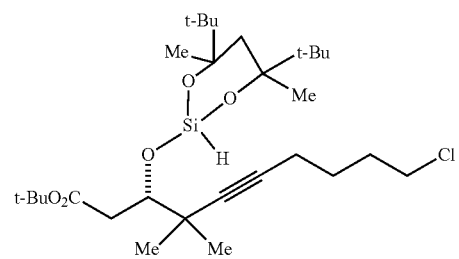
5
(1:1 mixture of diastereomers @ Si)
Rh(acac)(CO)$_2$
400 psi CO
→
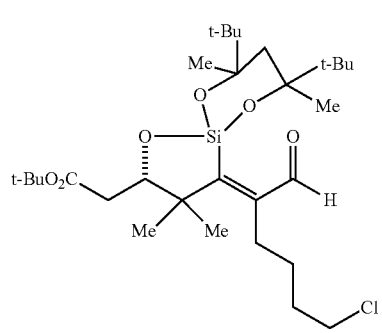
6
(1:1 mixture of diastereomers @ Si)
i. 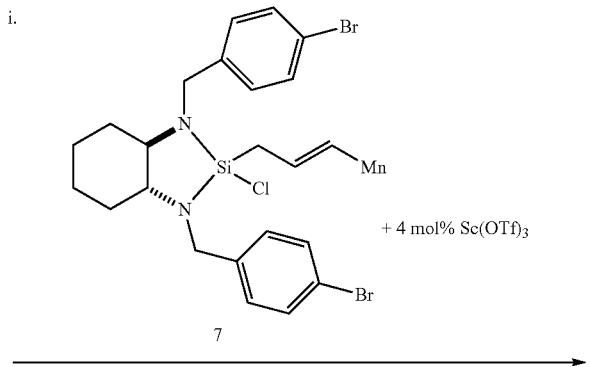
7
ii. TBAF·3H$_2$O
37% over 3 steps
→
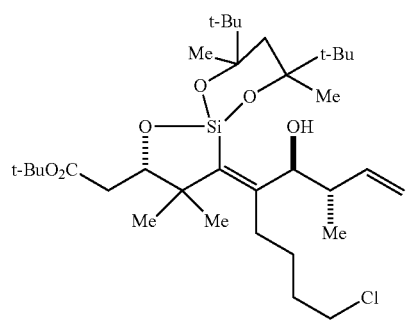
8
(2:1 mixture of diastereomers @ Si)

Moving forward to test the new substrates 8 in the "aprotic" Tamao oxidation, it was found that the selectivity for this reaction had increased (relative to the use of propyne in place of 2), providing access to 9 in 75% yield and >18:1 d.r (Scheme 3). With the $C_1$-$C_9$ analog fragment in hand, the synthesis of our targeted C6 linker analog of epothilone B could proceed.

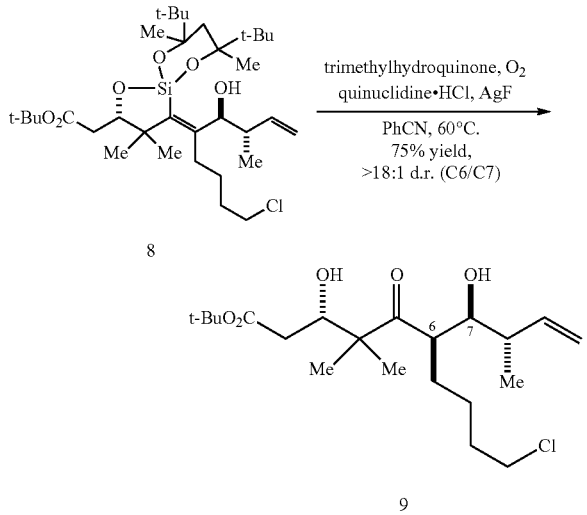

Experimentals

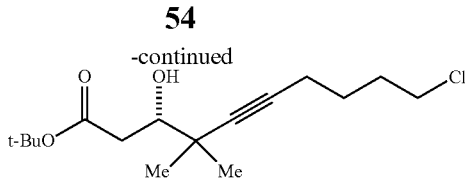

To a cooled (0° C.) solution of 2 (2.3 mL, 19.1 mmol) in $Et_2O$ (60 mL) was added n-BuLi (7.6 mL, 2.5M in hexane, 19.1 mmol) dropwise. After 5 minutes, $AlMe_3$ (9.1 mL, 2M in toluene, 18.3 mmol) was added dropwise. The reaction was warmed to room temperature and stirred for 15 minutes. The reaction was then cooled to −78° C. and 1 (1.62 g, 8.70 mmol) was added as a solution in $Et_2O$ (15 mL), followed by $BF_3 \cdot OEt_2$ (2.2 mL, 17.4 mmol). After 45 minutes, the reaction was slowly quenched with MeOH (20 mL). The mixture was stirred for 10 minutes then poured into 30 mL of saturated aqueous $NaHCO_3$ solution of pH 10. After stirring for about 45 minutes, the layers were separated and the aqueous layer extracted with $Et_2O$ (3×60 mL). The combined organics were washed with brine, dried over $MgSO_4$, filtered, and concentrated. The crude material was purified by silica gel chromatography (8% EtOAc/hexanes, p-anisaldehyde stain) to provide 3 as a clear, yellow oil (2.20 g, 84% yield). $^1$H NMR (500 MHz, $CDCl_3$) δ 3.75 (ddd, J=10.4, 4.5, 2.3 Hz, 1H), 3.56 (t, J=6.6 Hz, 2H), 2.91 (d, J=4.5 Hz, 1H), 2.62 (dd, J=16.0, 2.4 Hz, 1H), 2.39 (dd, J=16.0, 10.4 Hz, 1H), 2.21 (t, J=7.0 Hz, 2H), 1.92-1.82 (m, 2H), 1.69-1.60 (m, 2H), 1.47 (s, 9H), 1.20 (s, 3H), 1.18 (s, 3H); $^{13}$C NMR (125 MHz, $CDCl_3$) δ 172.8, 85.4, 81.6, 81.3, 74.6, 44.7, 38.8, 36.3, 31.8, 28.3, 26.4, 26.3, 24.9, 18.2; IR (film): 3494, 2974, 2934, 2868, 1712, 1455, 1392, 1367, 1302, 1254, 1151, 1079, 1041, 950, 762, 651 cm$^{-1}$; LRMS (FAB+) calcd $C_{16}H_{28}ClO_3$ [M+H]$^+$: 303.16, found 303.29; $[\alpha]^{20}_D$ −28.7 (c 1.20, $CHCl_3$).

To a cooled (0° C.) solution of silane 4 (817 mg, 2.93 mmol) in CH$_2$Cl$_2$ (28 mL) was added β-ketoester 3 (845 mg, 2.79 mmol) as a solution in CH$_2$Cl$_2$ (10 mL), followed by NEt$_3$ (0.58 mL, 4.19 mmol). The reaction was warmed to room temperature after 30 minutes. $^1$H NMR analysis was used to determine the conversion of the reaction mixture. Additional silane was added if starting material remained. Once complete, the reaction was concentrated and the residue filtered with Et$_2$O through an oven-dried frit. The filtrate was concentrated to provide intermediate 5 as a 1:1 mixture of diastereomers, which was used directly in the next step. Since this intermediate is difficult to purify due to hydrolytic sensitivity, and both diastereomers useful for our purposes, characterization reflects the mixture we obtained. Observed spectra: $^1$H NMR (500 MHz, CDCl$_3$) δ 4.47 (m, 2H), 4.13 (m, 2H), 3.55 (t, J=6.6 Hz, 4H), 2.76 (m, 2H), 2.44 (m, 2H), 2.19 (t, J=6.9 Hz, 4H), 1.92-1.81 (m, 4H), 1.69 (m, 4H), 1.67-1.57 (m, 4H), 1.47 (m, 18H), 1.37-1.28 (m, 12H), 1.21 (m, 6H), 1.12 (m, 6H), 0.94-0.87 (m, 36H); $^{13}$C NMR (125 MHz, CDCl$_3$) δ 171.2, 171.2, 86.3, 86.2, 81.2, 81.1, 80.7, 80.6, 80.0, 79.8, 79.6, 79.3, 77.4, 76.1, 75.9, 44.8, 40.5, 40.1, 39.2, 39.2, 39.1, 39.0, 38.3, 38.2, 36.2, 36.1, 31.7, 31.6, 28.4, 28.3, 27.3, 27.1, 27.1, 26.2, 25.8, 25.7, 24.9, 24.9, 24.9, 23.7, 23.4, 18.2, 18.2.

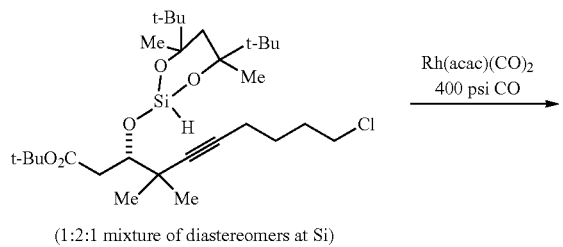

(1:2:1 mixture of diastereomers at Si)

Rh(acac)(CO)$_2$
400 psi CO

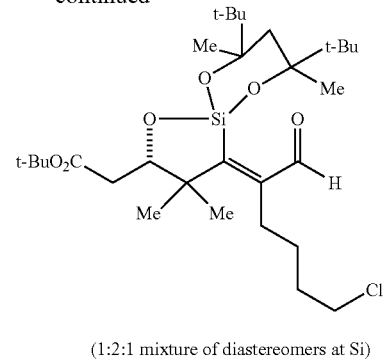

(1:2:1 mixture of diastereomers at Si)

A glass liner for a Parr bomb was charged with the crude 5 (from previous reaction) as a solution in CH$_2$Cl$_2$ (5.6 mL). The bomb was assembled and pressurized with CO to approximately 500 psi and then vented. This procedure was repeated two more times, then the bomb was pressurized again to 500 psi and stirred for about fifteen minutes.

The bomb was carefully vented and opened, then Rh(acac)(CO)$_2$ (0.223 mmol, 58 mg) was added. The bomb was reassembled and pressurized to 500 psi with CO then stirred at ambient temperature. After 24 hours, the bomb was carefully vented and opened. $^1$H NMR analysis indicated complete consumption of starting material and clean formation of product 6 as a 1.2:1 mixture of diastereomers. This reaction solution was used directly in the following crotylation reaction. Observed spectra of the diastereomeric mixture were as follows: $^1$H NMR (500 MHz, CDCl$_3$) δ 10.09 (s, 1H), 10.04 (s, 1H), 4.16 (dd, J=10.3, 3.4 Hz, 1H), 4.10 (dd, J=10.0, 2.8 Hz, 1H), 3.57 (m, 4H), 2.59-2.40 (m, 6H), 2.35 (dd, J=14.4, 10.0 Hz, 1H), 2.15 (dd, J=14.6, 10.4 Hz, 1H), 1.93-1.80 (m, 8H), 1.48 (m, 18H), 1.46 (s, 3H), 1.43 (s, 3H), 1.38 (s, 3H), 1.35 (s, 3H), 1.32 (s, 3H), 1.27 (m, 6H), 1.14 (s, 3H), 0.98 (s, 9H), 0.97-0.93 (m, 28H); $^{13}$C NMR (125 MHz, CDCl$_3$) δ 195.8, 195.6, 171.1, 170.6, 165.1, 163.1, 152.3, 151.6, 81.3, 81.2, 80.7, 80.6, 80.5, 80.1, 80.0, 78.2, 48.2, 47.3, 44.6, 41.7, 39.6, 39.5, 39.3, 39.2, 38.5, 37.9, 37.9, 33.0, 32.9, 28.1, 27.9, 27.8, 27.5, 27.0, 26.9, 26.7, 26.6, 25.8, 25.6, 24.9, 24.9, 24.9, 24.5, 23.8, 21.3; LRMS (FAB+) calcd C$_{30}$H$_{54}$ClO$_6$Si [M+H]$^+$: 573.33, found 573.7.

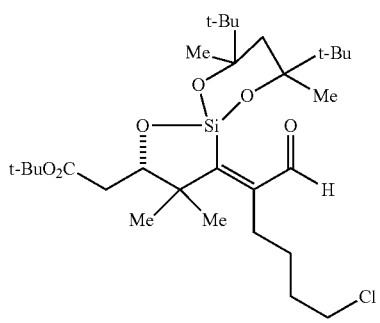

(1:1 mixture of diastereomers at Si)

i.

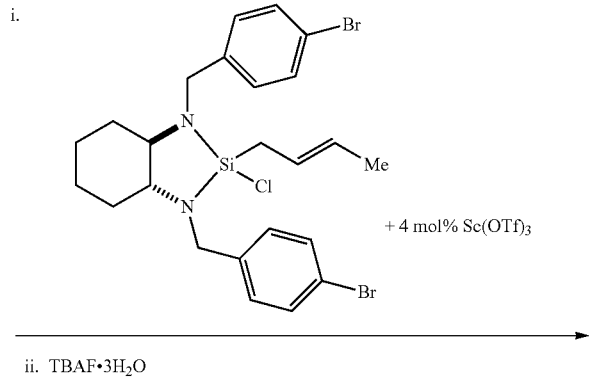

+4 mol% Sc(OTf)$_3$ ii. TBAF·3H$_2$O

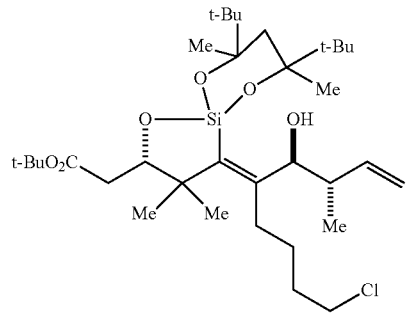

(2:1 mixture of diastereomers at Si)

To a solution of the reaction mixture from aldehyde 6 formation in CH$_2$Cl$_2$ (28 mL) was added (R, R)-trans-crotylsilane diamine reagent 37 (2.38 g, 4.19 mmol) and Sc(OTf)$_3$ (138 mg, 0.279 mmol). After 24 hours at room temperature, additional Sc(OTf)$_3$ and reagent were added. After another 16 hours, the reaction was still incomplete as judged by $^1$H NMR. The solution was then cooled to 0° C. and tetrabutylammonium fluoride (TBAF) trihydrate (879 mg, 2.79 mmol) was added portion-wise over 20 minutes. After about 3 hours, the reaction was concentrated and the residue purified via silica gel chromatography (5% EtOAc/hexanes) to afford 8 (658 mg, 37% over 3 steps) as a viscous yellow oil. 8 was a 2:1 mixture of diastereomers at silicon. (Another diastereomer that was formed in equal amount with the minor from unselective crotylation of one of the aldehyde diastereomers was removed via the silica gel chromatography.) $^1$H NMR (400 MHz, CDCl$_3$) 5.76 (m, 3H), 5.06-4.89 (m, 6H), 4.39 (d, J=2.3 Hz, 2H), 4.34 (d, J=2.3 Hz, 1H), 4.19-4.11 (m, 3H), 3.58 (m, 6H), 2.99 (d, J=3.4 Hz, 1H), 2.95 (d, J=3.1 Hz, 2H), 2.83 (m, 3H), 2.52 (m, 6H), 2.30 (m, 3H), 1.99 (m, 3H), 1.82 (m, 12H), 1.76-1.61 (m, 5H), 1.57-1.48 (m, 4H), 1.47 (m, 34H), 1.44 (m, 13H), 1.34-1.25 (m, 17H), 1.26-1.17 (m, 13H), 1.00-0.97 (m, 57H); $^{13}$C NMR (125 MHz, CDCl$_3$) δ 173.3, 173.1, 162.2, 138.9, 138.8, 134.6, 114.9, 114.8, 80.7, 80.6, 80.4, 80.1, 79.9, 79.9, 79.7, 74.2, 74.1, 44.7, 41.8, 41.4, 41.3, 39.9, 39.8, 39.5, 39.4, 38.7, 38.4, 38.3, 37.9, 37.6, 32.8, 32.7, 31.6, 29.8, 28.4, 28.2, 28.1, 28.1, 27.9, 27.7, 27.1, 26.4, 26.1, 25.9, 25.5, 25.2, 25.1, 25.1, 25.0, 24.7, 24.4, 22.7, 18.3, 18.2, 14.1; HRMS (DART+) calcd C$_{34}$H$_{61}$O$_6$ClSi [M+H]$^+$: 629.3986, found 629.4004.

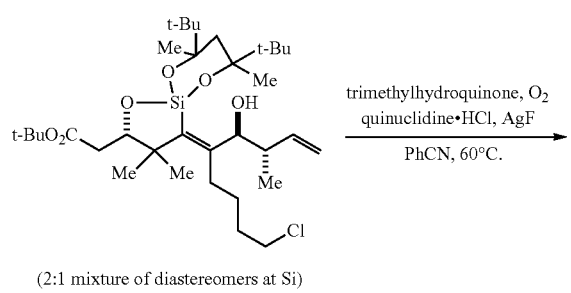

(2:1 mixture of diastereomers at Si)

trimethylhydroquinone, O$_2$
quinuclidine•HCl, AgF
PhCN, 60°C.

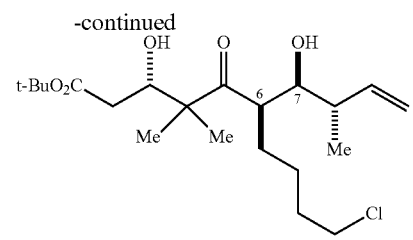

To a solution of trimethylhydroquinone (515 mg, 3.39 mmol), quinuclidine hydrochloride (450 mg, 3.05 mmol), and silver fluoride (459 mg, 3.62 mmol) in benzonitrile (5.0 mL) was added 8 (711 mg, 1.13 mmol) as a solution in benzonitrile (6.3 mL). The solution was purged with O$_2$ then the reaction was heated to 60° C. (oil bath, external temperature) and stirred overnight under a balloon of O$_2$. After 22 hours, the reaction was cooled to room temperature and diluted with CHCl$_3$ (15 mL). The solution was filtered through Celite, then washed with distilled water. The aqueous layer was extracted with CHCl$_3$ (3×15 mL). The combined organics were washed with brine, dried over MgSO$_4$, filtered, and concentrated. The residue was purified via silica gel chromatography (stepwise: 10% EtOAc/hexanes, 30% EtOAc/hexanes) to 9 (345 mg, 75%) as a brown oil with >18:1 diastereomeric ratio (d.r.) with respect to the newly formed stereocenter at C6. $^1$H NMR (300 MHz, CDCl$_3$) δ 5.87 (ddd, J=17.8, 10.4, 7.7 Hz, 1H), 5.12 (dd, J=8.4, 1.5 Hz, 1H), 5.09-5.05 (m, 1H), 4.24 (dt, J=10.0, 3.2 Hz, 1H), 3.61 (dt, J=8.1, 2.6 Hz, 1H), 3.53 (td, J=6.6, 3.4 Hz, 2H), 3.36 (d, J=3.5 Hz, 1H), 3.23 (dt, J=8.8, 3.2 Hz, 1H), 2.54 (d, J=2.6 Hz, 1H), 2.40 (dd, J=16.1, 2.9 Hz, 1H), 2.31 (dd, J=16.2, 9.7 Hz, 2H), 1.89-1.71 (m, 3H), 1.47 (s, 9H), 1.43-1.29 (m, 2H), 1.23 (s, 3H), 1.10 (s, 3H), 1.03 (d, J=6.8 Hz, 3H); $^{13}$C NMR (125 MHz, CDCl$_3$) 219.7, 172.5, 141.2, 115.4, 81.8, 73.7, 72.9, 52.0, 48.4, 44.8, 41.3, 37.4, 33.00, 28.2, 25.5, 24.7, 22.2, 19.2, 16.9; IR (film): 3494, 2971, 2932, 2872, 1706, 1457, 1392, 1368, 1303, 1253, 1221, 1153, 1033, 997, 915, 765, 727, 650 cm$^{-1}$; LRMS (FAB+) calcd C$_{21}$H$_{37}$ClO$_5$Na [M+Na]$^+$: 427.22, found 427.5; [α]$^{20}_D$ −46.7 (c 0.45, CHCl$_3$).

Synthesis Epo B Core

In the synthesis of our C6 linker analog, a previously described route reported by the Danishefsky group was used, which had been demonstrated to provide access to epothilone B (Rivkin, A. et al. 2002; Rivkin, A. et al. 2003; Rivkin, A. et al. 2004; Stachel, S. J. et al. 2001). Following the double TES protection and the tert-butyl ester cleavage of 9, fragment 10 was used directly for the esterification of fragment 12. Ring-closing metathesis of 12 using Grubbs second generation catalyst provided 13 in 66% yield (Scheme 4).

Experimentals

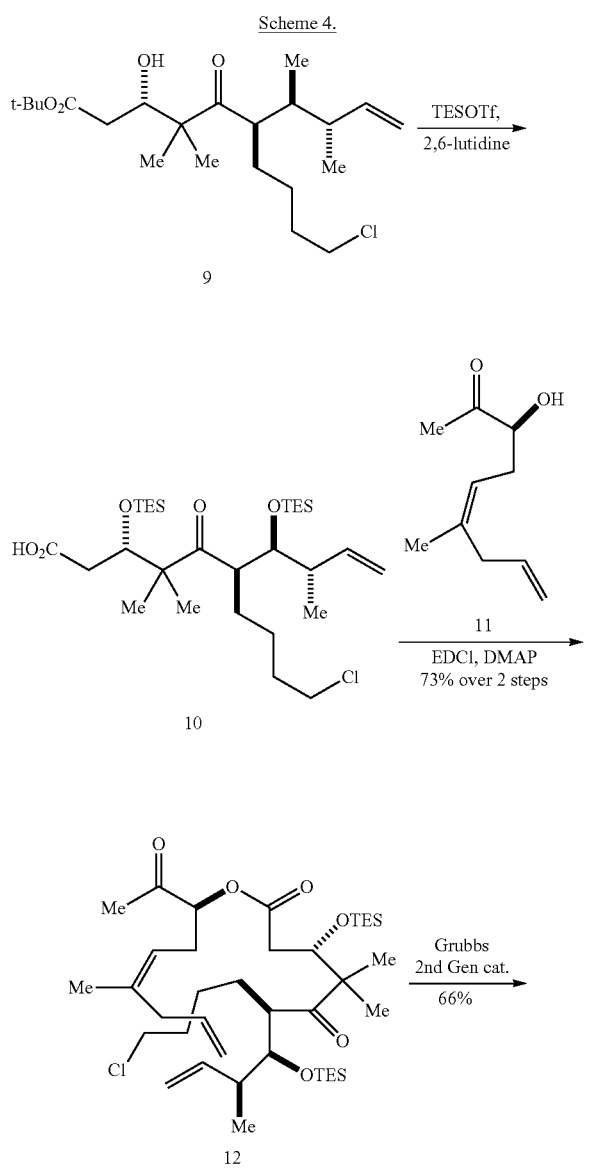

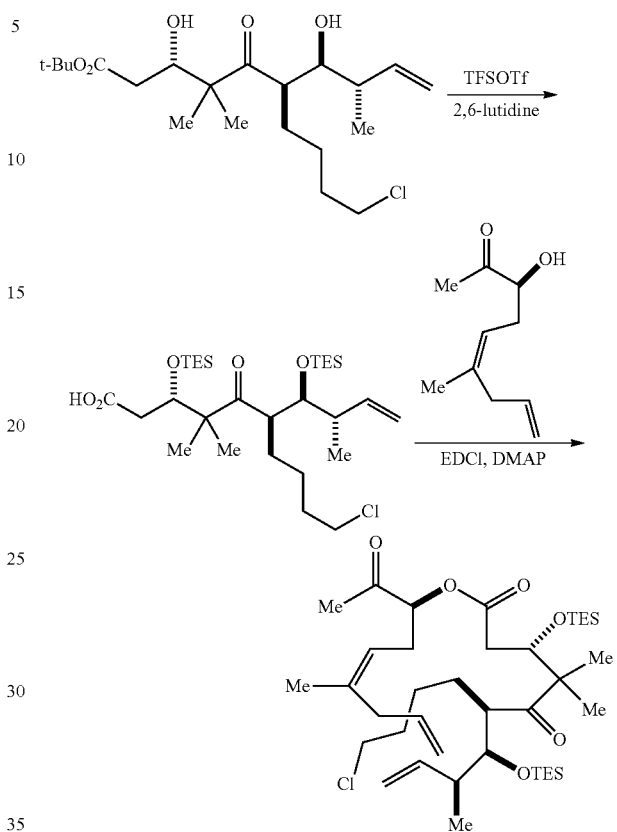

To a cooled (−78° C.) solution of 9 (345 mg, 0.852 mmol) in CH$_2$Cl$_2$ (8.8 mL) was added 2,6-lutidine (0.61 mL, 5.27 mmol). TESOTf (0.40 mL, 1.76 mmol) was then added dropwise. After 30 minutes, a second portion of TESOTf (0.40 mL, 1.76 mmol) was added and the cold bath was removed, allowing the reaction to warm to room temperature. After 2 hours, the reaction was diluted with Et$_2$O (80 mL), washed with 5% aqueous KHSO$_4$ (2×10 mL) then brine (15 mL), and then dried over Na$_2$SO$_4$ and concentrated. The residue was dissolved in aqueous THF (15 mL, 6:1 THF/H$_2$O) and treated with saturated aqueous NaHCO$_3$ (2 mL). After stirring at room temperature for 20 minutes, the mixture was diluted with Et$_2$O (20 mL) and acidified with 5% aqueous KHSO$_4$ (10 mL). The layers were separated then the aqueous layer extracted with Et$_2$O (2×15 mL). The combined organic layers were washed with brine, dried over Na$_2$SO$_4$, filtered, and concentrated to provide 10 as a mixture with TESOH. The crude product was used directly in the next step. For characterization purpose, purification via silica gel chromatography (15% EtOAc/hexanes, pH 7 buffered silica gel) provided 10 as a light yellow oil. $^1$H NMR (500 MHz, CDCl$_3$) δ 10.73 (bs, 1H), 5.94-5.79 (m, 1H), 5.11-4.98 (m, 2H), 4.32 (dd, J=7.4, 2.9 Hz, 1H), 3.86 (dd, J=5.3, 3.3 Hz, 1H), 3.50 (t, J=6.6 Hz, 2H), 3.03-3.00 (m, 1H), 2.60 (dd, J=16.6, 2.9 Hz, 1H), 2.33 (dd, J=16.6, 7.3 Hz, 1H), 2.20-2.13 (m, 1H), 1.76-1.59 (m, 3H), 1.51-1.45 (m, 1H), 1.39-1.28 (m, 2H), 1.21 (s, 3H), 1.12 (s, 3H), 1.05 (s, 3H), 0.98-0.94 (m, 18H), 0.71-0.52 (m, 12H). $^{13}$C NMR (125 MHz, CDCl$_3$) δ 216.6, 177.0, 140.2, 115.5, 75.8, 74.3, 53.3, 51.6, 45.0, 44.3, 39.6, 33.2, 27.0, 25.4, 24.2, 19.5, 18.7, 7.3, 7.1, 5.6, 5.3; IR (film): 2955, 2877, 2916, 1709, 1692, 1458, 1416, 1302, 1238, 1093, 1003, 914, 731 cm$^{-1}$; LRMS (FAB+) calcd C$_{27}$H$_{57}$ClO$_5$Si$_2$ [M+H]$^+$: 577.34, found 577.95; [α]$^{24}_D$ −22.6 (c 1.43, CHCl$_3$).

To a cooled (0° C.) solution of dried 11 (207 mg, 1.23 mmol) in CH$_2$Cl$_2$ (5.0 mL) was added solid DMAP (172 mg, 1.41 mmol) and EDCI (270 mg, 1.41 mmol). After stirring for 15 minutes, the crude 10 (azeotroped 3× with benzene) was added slowly as a solution in CH$_2$Cl$_2$ (7.6 mL). After 5 minutes, the cooling bath was removed and the reaction was allowed to warm to ambient temperature. After 4 hours, the reaction mixture was filtered directly though a plug of silica gel (10% EtOAc/hexanes). Purification via silica gel chromatography (2.5% EtOAc/hexanes) provided 12 (453 mg, 73% over 2 steps). $^1$H NMR (500 MHz, CDCl$_3$) δ 5.86 (ddd, J=17.2, 10.6, 8.1 Hz, 1H), 5.83-5.64 (m, 1H), 5.19 (t, J=7.2 Hz, 1H), 5.07-4.99 (m, 4H), 4.97 (t, J=6.2 Hz, 1H), 4.28 (dd, J=7.3, 2.8 Hz, 1H), 3.84 (dd, J=4.9, 3.5 Hz, 1H), 3.50 (t, J=6.6 Hz, 2H), 3.04-3.01 (m, 1H), 2.80-2.73 (m, 2H), 2.70 (dd, J=17.2, 2.9 Hz, 1H), 2.48 (t, J=6.8 Hz, 2H), 2.39 (dd, J=17.2, 7.4 Hz, 1H), 2.21-2.15 (m, 1H), 2.13 (s, 3H), 1.76-1.62 (m, 6H), 1.50-1.46 (m, 1H), 1.34 (d, J=8.0 Hz, 2H), 1.24 (s, 4H), 1.10 (s, 3H), 1.04 (d, J=7.0 Hz, 3H), 0.98-0.92 (m, 18H), 0.61 (q, J=8.2 Hz, 12H); $^{13}$C NMR (125 MHz, CDCl$_3$) δ 216.1, 205.3, 172.1, 140.3, 137.4, 135.4, 119.0, 115.8, 115.4, 78.8, 75.8, 74.7, 53.0, 51.8, 45.0, 44.4, 39.5, 36.5, 33.3, 29.2, 26.8, 26.6, 25.4, 24.0, 23.7, 20.4, 18.6, 7.3, 7.2, 5.6, 5.2; IR (film): 2955, 2877, 2911, 1731, 1693, 1638, 1458, 1416, 1379, 1295, 1238, 1161, 1092, 1003, 913, 728 cm$^{-1}$; HRMS (FAB+) calcd C$_{39}$H$_{70}$ClO$_6$Si$_2$ [M−H]$^+$: 725.45, found 725.4413; [α]$^{24}_D$ −24.5 (c 0.84, CHCl$_3$).

phy provided pure product for characterization. $^1$H NMR (400 MHz, CDCl$_3$) δ 5.58 (dd, J=15.8, 8.1 Hz, 1H), 5.34 (t, J=5.9 Hz, 1H), 5.19 (t, J=8.0 Hz, 1H), 4.96 (dd, J=9.2, 2.4 Hz, 1H), 4.17 (dd, J=9.7, 2.5 Hz, 1H), 4.10 (d, J=9.7 Hz, 1H), 3.61-3.42 (m, 2H), 3.17-3.04 (m, 1H), 3.03-2.89 (m, 2H), 2.72 (dd, J=15.4, 2.6 Hz, 1H), 2.62-2.52 (m, 1H), 2.52-2.43 (m, 1H), 2.38 (dd, J=14.5, 7.5 Hz, 1H), 2.29 (p, J=7.1 Hz, 1H), 2.21 (s, 3H), 1.78-1.67 (m, 3H), 1.66 (s, 3H), 1.54-1.38 (m, 2H), 1.27-1.19 (m, 1H), 1.17 (s, 3H), 1.11 (s, 3H), 1.05 (d, J=7.1 Hz, 3H), 1.00 (t, J=7.9 Hz, 9H), 0.91 (t, J=7.9 Hz, 9H), 0.67 (q, J=7.9 Hz, 6H), 0.57 (q, J=8.1 Hz, 6H); $^{13}$C NMR (125 MHz, CDCl$_3$) 213.9, 204.8, 171.4, 140.3, 132.6, 129.7, 118.6, 79.2, 77.0, 75.8, 54.0, 53.7, 44.8, 41.0, 40.3, 34.9, 33.1, 29.1, 28.3, 26.6, 23.8, 23.7, 23.6, 23.5, 21.4, 7.3, 7.1, 5.8, 5.4. IR (film): 2955, 2877, 2911, 1744, 1730, 1692, 1459, 1415, 1380, 1357, 1305, 1239, 1158, 1102, 1007, 855, 728 cm$^{-1}$; LRMS (FAB+) calcd C$_{37}$H$_{68}$ClO$_6$Si$_2$ [M+H]$^+$: 699.42, found 699.46; [α]$^{22}_D$ −10.0 (c 0.71, CHCl$_3$).

Completion of C(6) Azide Analog Synthesis

The thiazole-containing side chain was installed via Wittig olefination of 13 using the phosphonium ylide derived from 14 to complete the construction of the epothilone skeleton. Silyl group deprotection followed by selective diimide reduction of the C9-C10 disubstituted olefin provided 17. We chose this point to install the azide, forming 18 in excellent yield. This was followed by diastereoselective epoxidation using dimethyldioxirane to access our desired C6 linker analog of epothilone B 19 (Scheme 5).

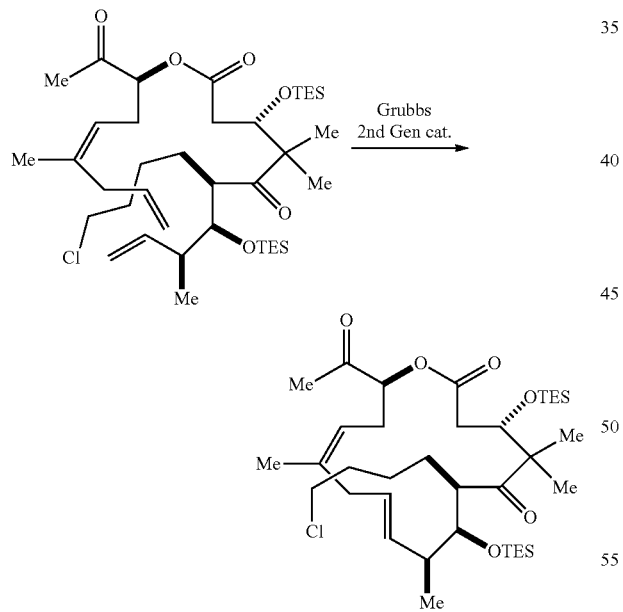

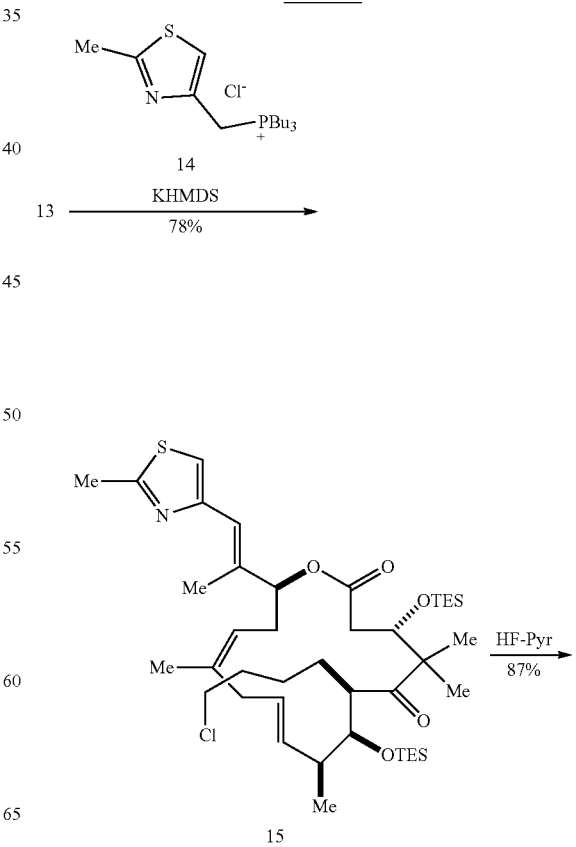

To a refluxing solution of 12 (93 mg, 0.128 mmol) in toluene (250 mL) was added a solution of Grubbs second generation catalyst (16 mg, 0.0192 mmol) in toluene (10 mL). After 30 minutes, the solution was cooled to 0° C. and then filtered through a plug of silica gel (hexanes then CH$_2$Cl$_2$). The combined filtrate was concentrated then the residue purified via silica gel chromatography (7.5% EtOAc/hexanes) to provide 13 (60 mg, 66%) as a 10:1 mixture with an unidentified but related impurity. Further chromatogra-

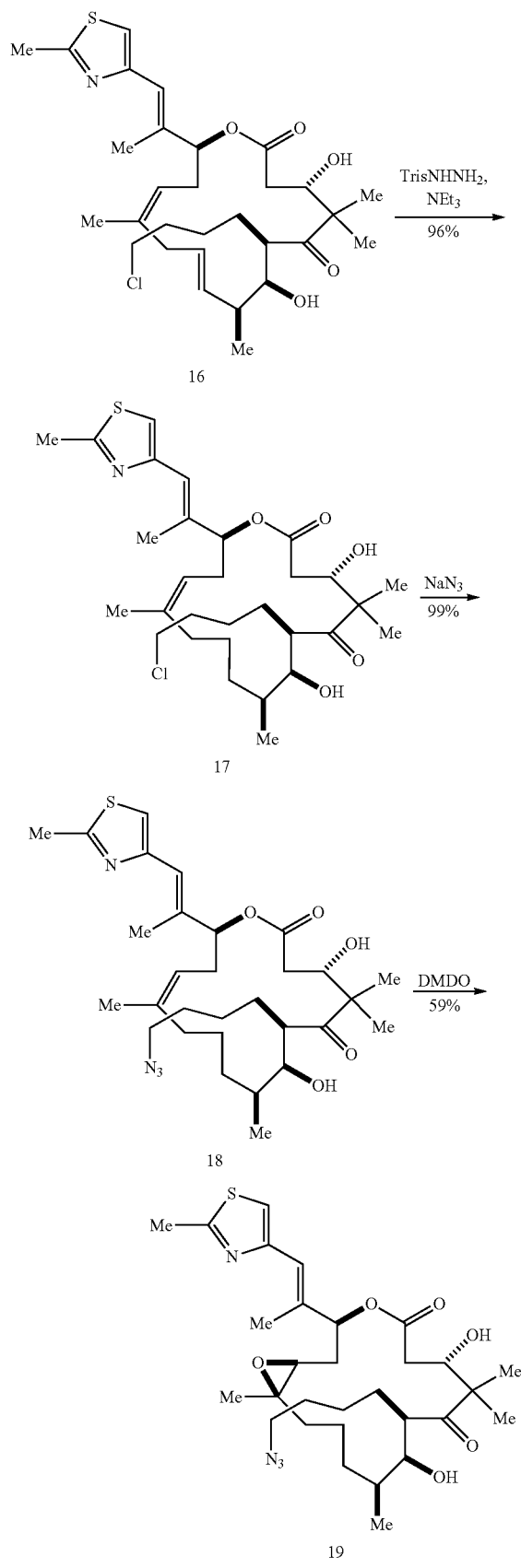

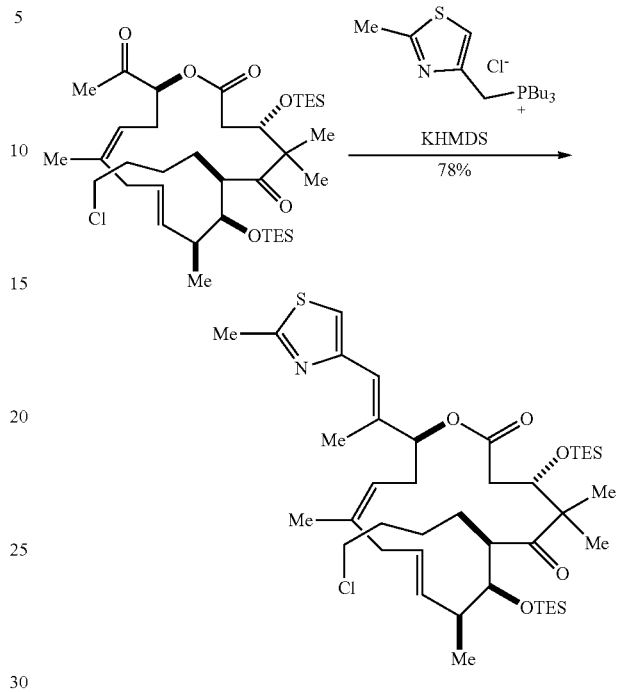

Experimentals

To a cooled (0° C.) solution of Wittig reagent 14 (180 mg, 0.515 mmol) in THF (4.6 mL) was added KHMDS (1.03 mL, 0.515 mmol). The mixture was stirred for 30 minutes, then cooled to −78° C. To the solution was added 13 (60 mg, 0.0858 mmol) as a solution in THF (4.0 mL), and the resulting mixture allowed to warm to about −20° C. over the course of 1.5 hour. The reaction was quenched with sat. aq. NH$_4$Cl (8 mL) and extracted with EtOAc (3×15 mL). The combined organic layers were dried over Na$_2$SO$_4$ and concentrated. The residue was purified via silica gel chromatography (4% EtOAc/hexanes) to afford 15 (53 mg, 78%) as a 14:1 mixture with the Z-isomer. Pure compound was obtained through further silica gel chromatography for characterization purposes. $^1$H NMR (400 MHz, CDCl$_3$) δ 6.96 (s, 1H), 6.56 (s, 1H), 5.66 (dd, J=15.7, 8.1 Hz, 1H), 5.40-5.28 (m, 2H), 5.22 (dd, J=10.0, 5.7 Hz, 1H), 4.31 (dd, J=9.5, 1.8 Hz, 1H), 4.11 (d, J=9.7 Hz, 1H), 3.56-3.40 (m, 2H), 3.15 (dd, J=14.5, 6.8 Hz, 1H), 3.00 (dt, J=9.6, 4.0 Hz, 1H), 2.71 (s, 3H), 2.71-2.62 (m, 2H), 2.47 (dd, J=14.6, 2.1 Hz, 1H), 2.41 (dd, J=14.6, 5.7 Hz, 1H), 2.24-2.13 (m, 2H), 2.13 (d, J=1.3 Hz, 3H), 1.90-1.78 (m, 1H), 1.75-1.61 (m, 5H), 1.54-1.37 (m, 2H), 1.22-1.12 (m, 1H), 1.11 (s, 3H), 1.07 (d, J=7.1 Hz, 3H), 1.04 (s, 3H), 1.01 (t, J=7.9 Hz, 9H), 0.88 (t, J=7.9 Hz, 9H), 0.68 (q, J=8.0 Hz, 6H), 0.56 (qd, J=8.3, 7.9, 1.7 Hz, 6H); $^{13}$C NMR (125 MHz, CDCl$_3$) δ 214.9, 170.7, 164.7, 152.7, 138.1, 138.1, 132.0, 129.6, 120.9, 120.4, 116.3, 79.3, 76.3, 74.8, 53.9, 53.8, 44.8, 41.2, 41.1, 35.4, 33.3, 33.2, 28.1, 24.5, 23.7, 23.5, 21.9, 21.7, 19.4, 15.1, 7.4, 7.1, 5.9, 5.5; IR (film): 2956, 2877, 2911, 1739, 1690, 1459, 1414, 1379, 1240, 1181, 1100, 1031, 1009, 971, 731 cm$^{-1}$; LRMS (FAB+) calcd C$_{42}$H$_{73}$ClNO$_5$SSi$_2$ [M+H]$^+$: 794.44, found 794.5; [α]$^{21}_D$ −11.5 (c 0.66, CHCl$_3$).

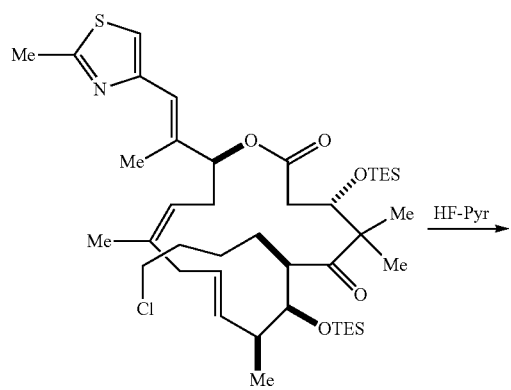

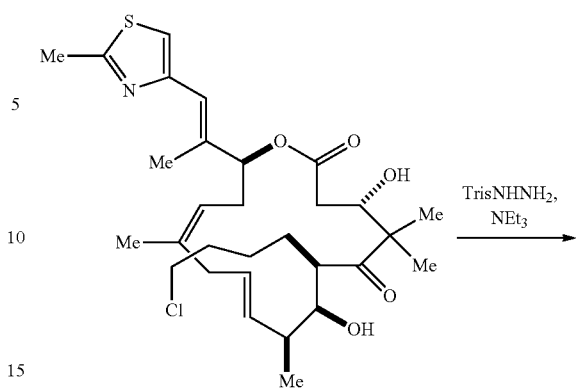

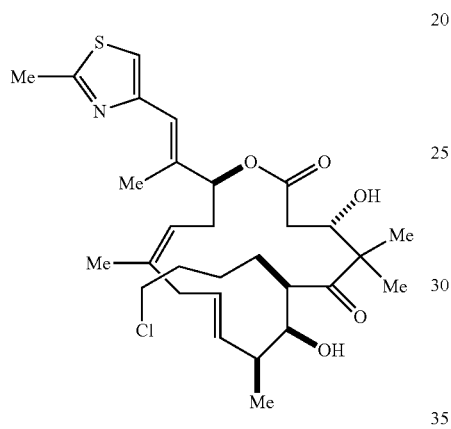

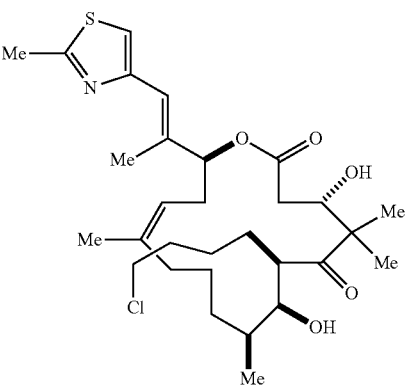

To a cooled (0° C.) solution of 15 (42 mg, 0.0528 mmol) in THF (1.1 mL) in a plastic tube was added HF pyridine (0.24 mL). After addition, the reaction was warmed to ambient temperature and stirred for 3 hours. The reaction was cooled to 0° C. and TMSOMe (2.5 mL) was added dropwise. After the addition, the reaction was warmed to ambient temperature and stirred for 15 minutes. The reaction was concentrated and dried under high vacuum, then the residue purified by silica gel chromatography (10% EtOAc/DCM) to provide 16 (26 mg, 87%). $^1$H NMR (400 MHz, CDCl$_3$) δ 6.97 (s, 1H), 6.54 (s, 1H), 5.58 (ddd, J=15.7, 7.6, 5.0 Hz, 1H), 5.47 (dd, J=15.7, 7.3 Hz, 1H), 5.33 (dd, J=9.0, 2.9 Hz, 1H), 5.12 (dd, J=9.2, 5.3 Hz, 1H), 4.29 (dt, J=8.2, 3.6 Hz, 1H), 3.77-3.67 (m, 1H), 3.51 (td, J=6.6, 4.1 Hz, 2H), 3.36-3.24 (m, 1H), 3.21 (d, J=4.8 Hz, 1H), 2.94 (dd, J=14.8, 7.6 Hz, 1H), 2.70 (s, 3H), 2.68-2.56 (m, 2H), 2.53 (dd, J=20.7, 4.1 Hz, 1H), 2.48-2.40 (m, 2H), 2.42-2.30 (m, 2H), 2.08 (s, 2H), 1.95-1.85 (m, 1H), 1.80-1.67 (m, 5H), 1.55-1.37 (m, 1H), 1.39-1.26 (m, 6H), 1.09 (d, J=6.9 Hz, 3H), 1.01 (s, 3H); $^{13}$C NMR (125 MHz, CDCl$_3$) 217.3, 170.8, 165.1, 152.3, 138.0, 137.8, 131.3, 129.9, 120.5, 119.7, 116.2, 78.4, 75.5, 72.7, 53.0, 51.1, 44.8, 39.3, 39.2, 35.3, 32.9, 32.3, 28.0, 24.6, 23.9, 21.6, 20.6, 19.4, 19.3, 15.9; IR (film): 3460, 2964, 2930, 2871, 1730, 1687, 1506, 1446, 1377, 1293, 1252, 1187, 1155, 1044, 977, 755 cm$^{-1}$; LRMS (FAB+) calcd C$_{30}$H$_{45}$ClNO$_5$S [M+H]+: 566.26, found 566.32; [α]$^{22}_D$ −82.4 (c 0.75, CHCl$_3$).

To a solution of 16 (26 mg, 0.0459 mmol) and Tris-NHNH$_2$ (548 mg, 1.84 mmol) in ClCH$_2$CH$_2$Cl (13 mL) at 50° C. (external temp, oil bath) was added NEt$_3$ (0.26 mL, 1.84 mmol). After 8 hours, the reaction was cooled to ambient temperature and diluted with EtOAc, then filtered through a plug of silica gel. The filtrate was concentrated, then the residue purified via silica gel chromatography (30% EtOAc/hexanes) to provide 17 (25 mg, 96%). $^1$H NMR (500 MHz, CDCl$_3$) δ 6.95 (s, 1H), 6.56 (s, 1H), 5.23 (dd, J=10.3, 2.1 Hz, 1H), 5.12 (dd, J=10.0, 4.6 Hz, 1H), 4.25 (d, J=10.6 Hz, 1H), 3.77-3.68 (m, 1H), 3.58-3.42 (m, 3H), 3.29 (dt, J=7.9, 4.1 Hz, 1H), 2.70 (s, 3H), 2.68-2.60 (m, 1H), 2.57 (d, J=3.7 Hz, 1H), 2.48 (dd, J=14.8, 10.4 Hz, 1H), 2.39 (dd, J=14.8, 2.8 Hz, 1H), 2.33-2.27 (m, 1H), 2.27-2.21 (m, 1H), 2.07 (s, 3H), 1.91-1.70 (m, 6H), 1.69 (s, 3H), 1.66-1.56 (m, 1H), 1.48-1.37 (m, 3H), 1.33 (s, 3H), 1.29-1.21 (m, 2H), 1.08 (s, 3H), 1.04 (d, J=7.0 Hz, 3H); $^{13}$C NMR (125 MHz, CDCl$_3$) δ 219.2, 170.7, 165.2, 152.2, 139.6, 139.2, 120.4, 119.5, 115.9, 79.4, 74.4, 72.6, 53.5, 48.9, 44.8, 39.6, 36.2, 33.0, 32.8, 32.3, 30.7, 27.0, 25.1, 25.0, 23.8, 22.1, 19.7, 19.3, 17.1, 15.9; IR (film): 3474, 2960, 2932, 2871, 1731, 1686, 1507, 1464, 1446, 1377, 1337, 1291, 1252, 1187, 1151, 1072, 1029, 981, 755 cm$^{-1}$; LRMS (FAB+) calcd C$_{30}$H$_{47}$ClNO$_5$S [M+H]$^+$: 568.28, found 568.34; [α]$^{23}_D$ −55.0 (c 0.70, CHCl$_3$).

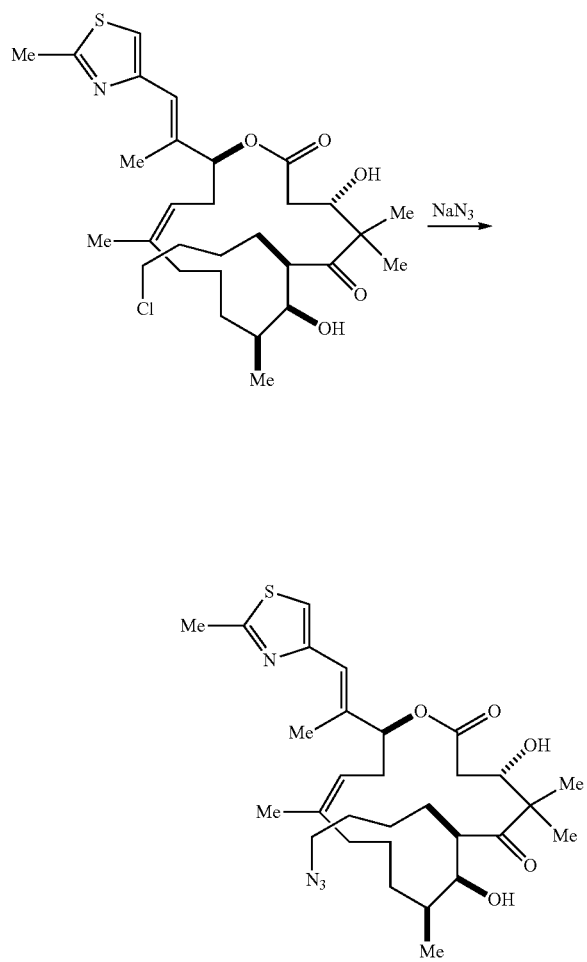

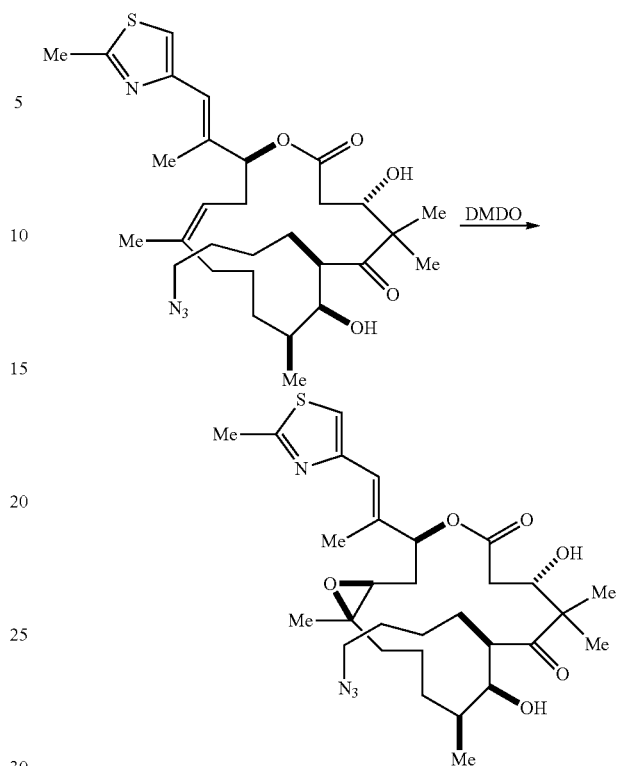

To a solution of 17 (25 mg, 0.044 mmol) in DMF (0.5 mL) was added NaN$_3$ (3.4 mg, 0.0523 mmol). The reaction was heated to 60° C. (external temp, oil bath) and stirred overnight. After 24 hours, the reaction was cooled to ambient temperature, then diluted with EtOAc and deionized water. The layers were separated and the aqueous layer extracted with EtOAc (3×5 mL). The combined organic layers were dried over Na$_2$SO$_4$ and concentrated. The residue was purified via silica gel chromatography to provide 18 (25 mg, 99%). $^1$H NMR (400 MHz, CDCl$_3$) δ 6.95 (s, 1H), 6.56 (s, OH), 5.22 (d, J=9.8 Hz, 1H), 5.11 (dd, J=10.0, 4.8 Hz, 1H), 4.31-4.23 (m, 1H), 3.75-3.65 (m, 2H), 3.59 (d, J=5.6 Hz, 1H), 3.32-3.23 (m, 3H), 2.69 (s, 3H), 2.67-2.61 (m, 1H), 2.62-2.56 (m, 2H), 2.48 (dd, J=14.8, 10.4 Hz, 1H), 2.38 (dd, J=14.8, 2.9 Hz, 1H), 2.33-2.26 (m, 1H), 2.28-2.18 (m, 2H), 2.06 (d, J=1.3 Hz, 3H), 1.88-1.71 (m, 4H), 1.69 (s, 2H), 1.67-1.59 (m, 3H), 1.58-1.51 (m, 1H), 1.37-1.28 (m, 6H), 1.07 (s, 3H), 1.04 (d, J=7.0 Hz, 3H); $^{13}$C NMR (125 MHz, CDCl$_3$) δ 219.1, 170.7, 165.1, 152.2, 139.6, 139.2, 120.4, 119.5, 115.9, 79.3, 74.4, 72.5, 53.4, 51.3, 48.9, 39.6, 36.2, 32.8, 32.3, 30.7, 29.5, 27.3, 25.0, 23.7, 22.0, 19.7, 19.2, 17.1, 15.9; IR (film): 3464, 2955, 2927, 2854, 2096, 1733, 1685, 1463, 1378, 1289, 1261, 1184, 1148, 1075, 1029, 803 cm$^{-1}$; LRMS (FAB+) calcd C$_{30}$H$_{47}$N$_4$O$_5$S [M+H]$^+$: 575.32, found 575.40; [α]$^{21}_D$ −51.0 (c 0.68, CHCl$_3$).

To a cooled (−78° C.) solution of 18 (25 mg, 0.0433 mmol) in CH$_2$Cl$_2$ (2.2 mL) was added a cooled (−78° C.) solution of DMDO (1.5 mL, 0.130 mmol, 0.086M in acetone) via cannula. After the addition was complete, the solution was warmed to −50° C. and stirred for 2 hours. Additional DMDO solution was added since there was starting material remaining. After another 2 hours the reaction seemed to have stalled, so dimethyl sulfide was added to quench any remaining DMDO, then the solution concentrated. The residue was purified via silica gel chromatography (pH 7 buffered silica gel, 40% EtOAc/hexanes) to provide 19 (14.5 mg, 59%). $^1$H NMR (400 MHz, CDCl$_3$) δ 6.97 (s, 1H), 6.55 (s, 1H), 5.46 (t, J=5.0 Hz, 1H), 4.61 (d, J=5.7 Hz, 1H), 4.27 (ddd, J=10.2, 5.5, 2.5 Hz, 1H), 3.63 (q, J=5.3 Hz, 1H), 3.44 (dt, J=8.3, 3.9 Hz, 1H), 3.26 (td, J=6.7, 4.1 Hz, 2H), 2.87 (d, J=5.8 Hz, 1H), 2.80 (t, J=6.2 Hz, 1H), 2.70 (s, 3H), 2.56 (dd, J=14.3, 10.3 Hz, 1H), 2.41 (dd, J=14.3, 2.6 Hz, 1H), 2.10 (d, J=1.3 Hz, 3H), 2.02 (t, J=5.7 Hz, 2H), 1.92-1.77 (m, 1H), 1.78-1.69 (m, 2H), 1.64-1.50 (m, 4H), 1.53-1.41 (m, 1H), 1.37 (s, 3H), 1.33-1.22 (m, 9H), 1.03 (s, 3H), 0.99 (d, J=6.9 Hz, 3H); $^{13}$C NMR (125 MHz, CDCl$_3$) δ 220.0, 170.7, 165.2, 152.1, 137.0, 119.4, 116.4, 76.7, 75.5, 73.5, 61.4, 61.0, 53.2, 51.3, 50.4, 39.0, 34.8, 32.2, 31.7, 30.1, 29.4, 28.3, 25.2, 22.3, 21.2, 21.1, 20.5, 19.3, 17.5, 16.2; IR (film): 3446, 2960, 2926, 2859, 2095, 1735, 1685, 1504, 1463, 1379, 1345, 1289, 1259, 1183, 1144, 1050, 1025, 978, 803, 735 cm$^{-1}$; LRMS (FAB+) calcd C$_{30}$H$_{47}$N$_4$O$_6$S [M+H]$^+$: 591.31, found 591.45; [α]$^{23}_D$ −71.6 (c 0.53, CHCl$_3$).

Azide Derivatization

After obtaining the azide-containing analog 19, we were able to access both a triazole derivative 3.36 and an acetamide derivative 3.37, through a strain-released click reaction Dommerholt, J. et al. 2010) and traceless Staudinger ligation (Soellner, M. B. et al. 2006), respectively (Scheme 6).

Scheme 6.
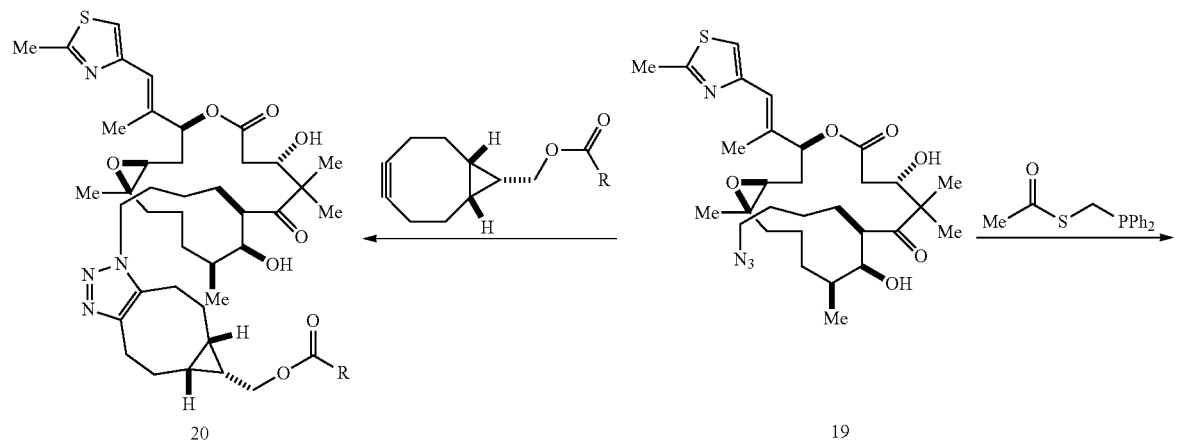
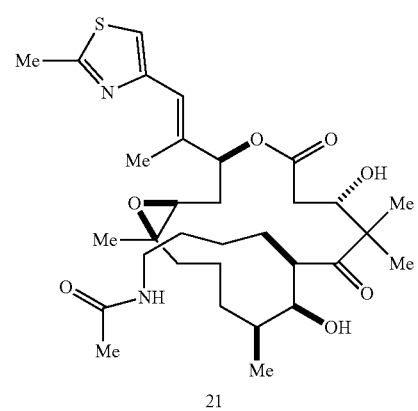
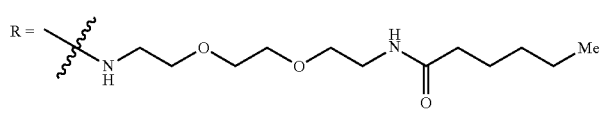
Experimentals
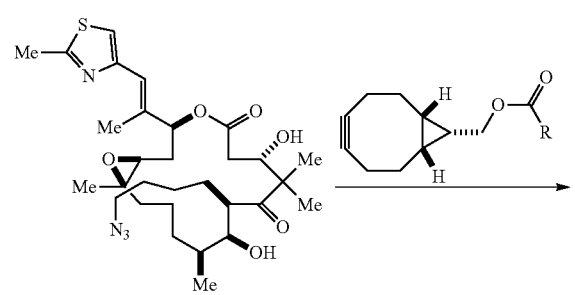
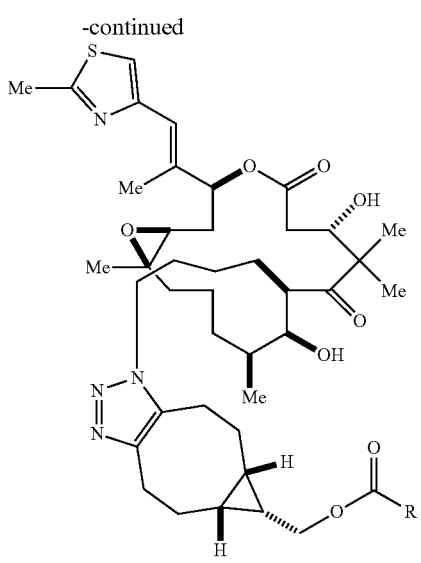

-continued

R =
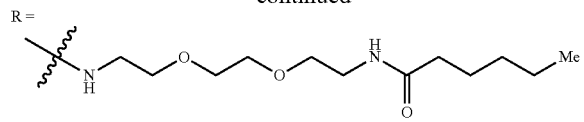

To 19 (2.4 mg, 0.00406 mmol) was added the alkyne (1.7 mg, 0.00406 mmol) as a solution in a 1:2 mixture of CD$_3$CN:D$_2$O (0.5 mL). This was left to stir overnight at ambient temperature, then the next day loaded directly onto a plug of silica gel and filtered (EtOAc then acetone). The filtrate was concentrated, then the residue purified via silica gel chromatography (4% MeOH/CH$_2$Cl$_2$) to provide 20 (4.0 mg, 97%). $^1$H NMR (500 MHz, CDCl$_2$) δ 6.97 (s, 1H), 6.56 (s, 1H), 5.95 (s, 1H), 5.46 (dd, J=6.5, 3.5 Hz, 1H), 5.18 (s, 1H), 4.42 (s, 1H), 4.28-4.18 (m, 3H), 4.16 (d, J=8.0 Hz, 2H), 3.69-3.54 (m, 9H), 3.46 (q, J=5.3 Hz, 2H), 3.43-3.33 (m, 5H), 3.17-3.05 (m, 3H), 2.93-2.83 (m, 2H), 2.81 (t, J=6.2 Hz, 1H), 2.70 (s, 3H), 2.69-2.61 (m, 1H), 2.55 (dd, J=14.3, 10.1 Hz, 1H), 2.41 (dd, J=14.4, 2.9 Hz, 1H), 2.27-2.19 (m, 1H), 2.17 (t, J=7.6 Hz, 2H), 2.10 (d, J=1.2 Hz, 3H), 2.06-1.97 (m, 2H), 1.96-1.84 (m, 1H), 1.85-1.75 (m, 1H), 1.79-1.69 (m, 1H), 1.68-1.61 (m, 2H), 1.60-1.47 (m, 6H), 1.47-1.35 (m, 1H), 1.37-1.28 (m, 7H), 1.27 (s, 4H), 1.26-1.15 (m, 3H), 1.03-0.97 (m, 5H), 0.89 (t, J=6.9 Hz, 4H); $^{13}$C NMR (125 MHz, CDCl$_3$) δ 219.5, 170.7, 165.2, 156.8, 152.1, 145.0, 144.9, 137.0, 132.8, 119.6, 116.4, 76.7, 75.0, 73.5, 70.4, 70.4, 70.2, 70.2, 62.8, 61.4, 61.2, 53.1, 53.1, 50.3, 47.4, 41.0, 39.3, 39.1, 36.9, 35.0, 32.1, 31.9, 31.6, 30.3, 29.9, 27.7, 26.1, 25.6, 24.0, 23.2, 22.8, 22.6, 22.5, 22.3, 21.6, 21.1, 20.5, 20.2, 19.6, 19.3, 17.9, 17.7, 16.1, 14.1; IR (film): 3341, 2956, 2930, 2869, 1713, 1696, 1649, 1549, 1535, 1466, 1379, 1253, 1143, 1100, 1048, 1024, 753 cm$^{-1}$; LRMS (FAB+) calcd C$_{53}$H$_{85}$N$_6$O$_{11}$S [M+H]$^+$: 1013.59, found 1013.79; [α]$^{22}$$_D$ −31.9 (c 0.44, CHCl$_3$).

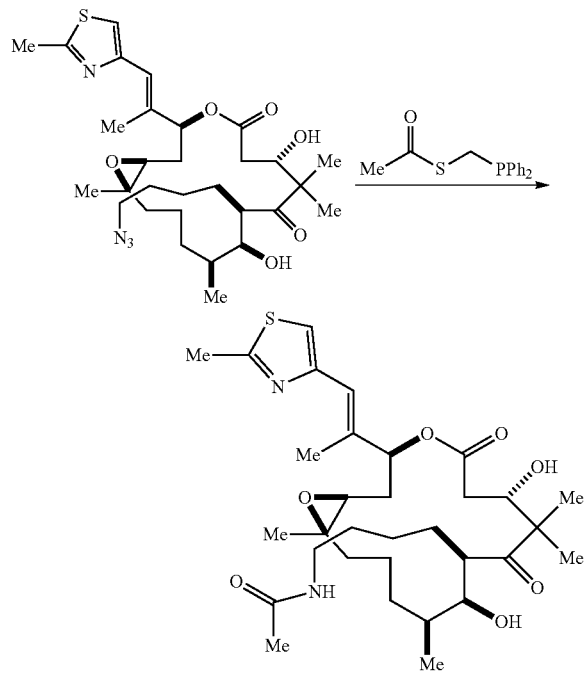

To 19 (5.6 mg, 0.00948 mmol) was added the phosphinothioester (75 mg, 0.260 mmol) as a solution in 1:1 THF:D$_2$O (2 mL). The reaction was allowed to stir overnight at ambient temperature. Most of the starting material transformed into an unidentified side product, but a small amount of 21 (0.7 mg, 11% yield) was isolated from silica gel chromatography (5% MeOH/CH$_2$Cl$_2$). $^1$H NMR (400 MHz, CHCl$_3$) δ 6.97 (s, 1H), 6.56 (s, 1H), 5.53-5.39 (m, 2H), 4.51 (d, J=5.9 Hz, 1H), 4.29-4.19 (m, 1H), 3.72-3.60 (m, 1H), 3.42 (dt, J=8.3, 4.3 Hz, 1H), 3.33-3.12 (m, 2H), 3.01 (d, J=5.7 Hz, 1H), 2.81 (t, J=6.2 Hz, 1H), 2.70 (s, 3H), 2.56 (dd, J=14.4, 10.1 Hz, 1H), 2.42 (dd, J=14.4, 2.9 Hz, 1H), 2.10 (d, J=1.3 Hz, 3H), 2.06-1.97 (m, 1H), 1.97 (s, 3H), 1.94-1.79 (m, 1H), 1.74-1.63 (m, 1H), 1.54-1.37 (m, 10H), 1.35 (s, 3H), 1.31-1.17 (m, 8H), 1.03 (s, 3H), 0.99 (d, J=6.8 Hz, 3H); LRMS (APCI+) calcd C$_{32}$H$_{51}$N$_2$O$_7$S [M+H]$^+$: 607.33, found 606.86.

Additional C(6)-Analogs

The compounds of the present invention are C(6)-analogs of Epo B, which have improved potency relative to Epo B, or similar or slightly diminished potency with an improved pharmacokinetic profile. Additional C(6)-analogs of Epo B are prepared using the methods described herein.

Biological Data

Compounds 19, 20 and 21 were assayed for cell growth inhibition against four cell lines (PC3 (prostate), MCF7 (breast), H522 (lung), and OVCAR8 (ovarian)) alongside reference samples of Epo A, ixabepilone and taxol (Table 1). From this data, it appears that our linker analogs have not lost activity through extension of the methyl group or through incorporation of the amide or triazole functionalities at the end of the butyl linker. The IC$_{50}$ values for the C(6) analogs were similar or lower than Epo A for each cell line and were lower than taxol in the PC3 and H522 assay.

TABLE 1

The IC$_{50}$ values for Epo B analogs in cell growth inhibition assays.

| Compound | PC3 (Prostate) | MCF7 (Breast) | H522 (Lung) | OVCAR8 (Ovarian) |
|---|---|---|---|---|
| Taxol | 6 | <0.13 | 2.6 | 1.9 |
| Ixabepilone | 4 | 2 | 2.5 | 3.3 |
| Epo A | 7 | 7 | 5.5 | 6 |
| 19 | 2.1 | <0.65 | 0.4 | 1 |
| 20 | 2.3 | <0.65 | 0.5 | 7 |
| 21 | 1 | 0.65 | 0.6 | 2.2 |

Example 2. Dictyostatin Analogs

Synthesis of Key Intermediate 14

In our synthesis of dictyostatin (Ho, S. et al. 2013), the C(6) methyl group is installed in a Sc(OTf)3-catalyzed crotylation (Kim H. et al. 2011) of aldehyde 3 to give ketone 4 (Scheme 1a). To incorporate a 4-azidobutyl group instead, we employed a cross-metathesis reaction between allylsilane 5 and 6-chlorohex-1-ene using the 2nd generation Hoveyda-Grubbs catalyst (HG-II) (Garber, S. B. et al. 2000) to produce 6 (~3:1 E:Z), which was employed in situ in a Sc(OTf)3-catalyzed allylation of aldehyde 3. After treatment with HCl to hydrolyze the ketal, ketone 7 was isolated as a 3:1 mixture of diastereomers in 58% overall yield (90% ee for the major diastereomer). The moderate diastereoselectivity of the metathesis reaction notwithstanding, this experimentally simple one-pot assemblage of 7 further highlights the versatility of our allylsilane platform. Subjection of 7 (~3:1 dr) to the one-pot protection/bromination reaction gave 8 (~3:1 dr), which was subjected to the Arbuzov/transesterification method we developed (Ho, S. et al. 2013)

to give Still-Gennari-type β-ketophosphonate 9 (~3:1 dr). Displacement of the chloride with NaN3 delivered 10 (~3:1 dr). Finally, Heck reaction with iodide 11 (TMSE=2-trimethylsilyethyl) produced completed fragment 12 in 58% overall yield. The diastereomers were separable at this stage, and we were able to isolate 12 in 30% yield (Scheme 1b).
Scheme 1a.
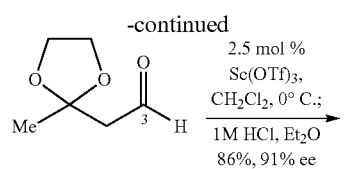
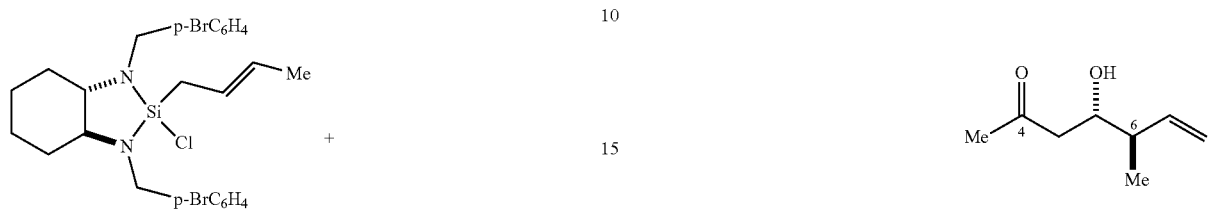
Scheme 1b.
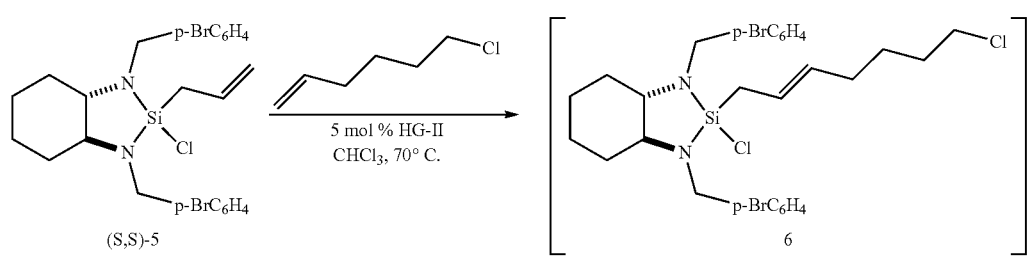
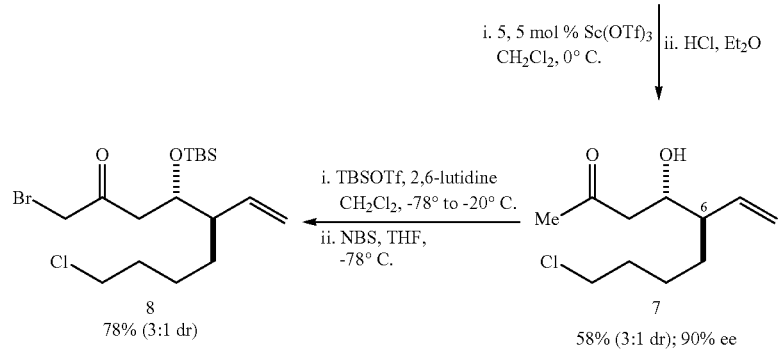
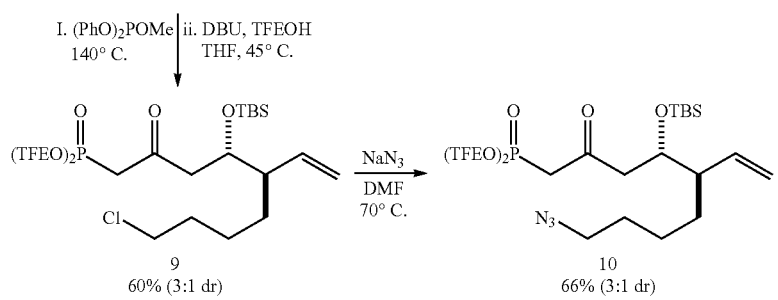
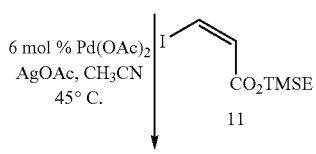

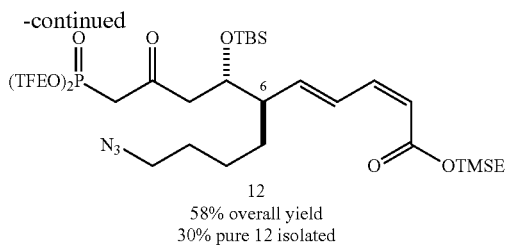

12
58% overall yield
30% pure 12 isolated

Experimentals

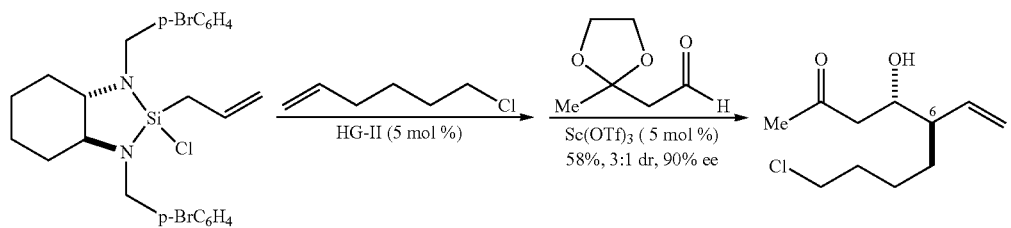

To a solution of the (S,S)-allylsilane (6.7 g, 12 mmol, 1.1 equiv) and 6-chloro-1-hexene (3.2 mL, 24 mmol, 2.2 equiv) in CHCl$_3$ (60 mL, 0.2M) was added 2$^{nd}$ generation Hoveyda-Grubbs catalyst (378 mg, 0.60 mmol, 5 mol %). The reaction mixture was heated to 70° C. After 5 h, the reaction mixture was cooled to 0° C. Aldehyde 3 (1.4 g, 11 mmol, 1 equiv) was added, followed by scandium triflate (270 mg, 0.60 mmol, 5 mol %). After vigorously stirring for 2.5 h at 0° C., the reaction mixture was concentrated, re-suspended in Et$_2$O (60 mL), and quenched at 0° C. with 1N HCl (60 mL). This acidic isolation serves both to hydrolyze the C9 ketal and protonate the diaminocyclohexane controller. After stirring overnight, the reaction mixture was filtered. The aqueous layer of the filtrate was separated and extracted with EtOAc (3×100 mL). The combined organic layers were washed with saturated aqueous NaHCO$_3$ (50 mL), dried over MgSO$_4$, filtered, and concentrated. Purification was accomplished by silica gel flash column chromatography (10-40% EtOAc/Hex) affording methyl ketone 7 (1.4 g, 3:1 dr, 58% combined yield) as a dark red oil, presumably contaminated with ruthenium. A more complete purification was therefore performed after the following step. The enantiomeric excess of 7 was determined to be 91% ee by $^1$H NMR and chiral GC analysis of the derived (R)-MTPA Mosher ester. TLC R$_f$=0.3 (25% EtOAc/Hex); IR (thin film) 3446 (bs), 2935, 1707, 1359, 1000, 917, 733 cm$^{-1}$; $^1$H NMR (500 MHz, CDCl$_3$) δ (major diastereomer) 5.66 (dt, J=17.3, 9.8 Hz, 1H, C$_5$H), 5.17-5.02 (m, 2H, C$_4$H$_2$), 4.03 (dt, J=6.3, 3.4 Hz, 1H, C$_7$H), 3.51 (t, J=6.7 Hz, 2H, α-Cl), 2.84 (d, J=2.9 Hz, 1H, OH), 2.70-2.45 (m, 2H, C$_8$H$_2$), 2.16 (s, 3H, C$_{10}$H$_3$), 1.96 (app. tt, J=8.9, 4.1 Hz, 1H, C$_6$H), 1.83-1.67 (m, 2H, β-Cl), 1.56-1.17 (m, 4H); $^{13}$C NMR (125 MHz, CDCl$_3$) δ (major diastereomer) 209.9, 138.0, 117.9, 69.7, 49.7, 48.0, 45.1, 32.7, 31.0, 30.1, 24.8; HRMS: Exact mass calcd for C$_{11}$H$_{19}$ClNaO$_2$ [M+Na]$^+$: 241.0971; found 241.0984 (TOF MS ES+).

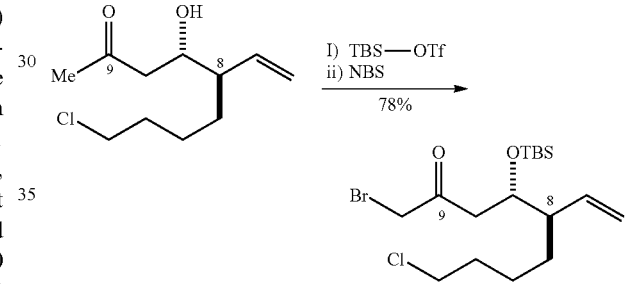

To a cooled (−78° C.) solution of ketone 7 (360 mg, 2.5:1 dr, 1.7 mmol, 1 equiv) in CH$_2$Cl$_2$ (17 mL, 0.1M) was added 2,6-lutidine (778 μL, 6.9 mmol, 4.2 equiv) and freshly-distilled TBS-OTf (794 μL, 3.5 mmol, 2.1 equiv). The reaction mixture was allowed to warm to 0° C. as the dry ice bath expired. After 3 h, the reaction mixture was re-cooled to −78° C., and a solution of N-bromosuccinimide (352 mg, 2.0 mmol, 1.2 equiv) in THF (8.5 mL) was added over 30 min. After 3 h, the reaction mixture was quenched with saturated aqueous NaHCO$_3$ (20 mL). The aqueous layer was separated and extracted with CH$_2$Cl$_2$ (3×20 mL). The combined organic layers were dried over MgSO$_4$, filtered, and concentrated. Purification was accomplished by pH 7.0 buffered silica gel flash column chromatography (1% EtOAc/Hex) affording bromoketone 8 as a mixture of C6 diastereomers (530 mg, 2.5:1 dr, 78% combined yield). This material was used without further purification, and the separation of diastereomers was performed at a later stage. TLC R$_f$=0.53 (10% EtOAc/Hex, one spot); IR (thin film) 2930, 2857, 1717, 1462, 1253, 1074, 834, 776 cm$^{-1}$; $^1$H NMR (500 MHz, CDCl$_3$) δ 5.62 (ddd, J=17.3, 10.3, 9.1 Hz, 1H, C$_5$H major), 5.59 (ddd, J=17.2, 10.3, 8.6 Hz, 1H, C$_5$H minor), 5.15-4.99 (m, 2H, C$_4$H$_2$), 4.19 (ddd, J=6.8, 5.7, 3.0 Hz, 1H, C$_7$H major), 4.13 (ddd, J=7.1, 5.5, 4.3 Hz, 1H, C$_7$H minor), 3.90 (s, 2H, C$_{10}$H$_2$ minor), 3.88 (s, 2H, C$_{10}$H$_2$ major), 3.51 (t, J=6.7 Hz, 2H, α-Cl), 2.81-2.61 (m, 2H, C$_8$H$_2$), 2.16-2.10 (m, 1H, C$_6$H minor), 2.07 (app. tt, J=9.3, 3.3 Hz, 1H, C$_6$H major), 1.83-1.67 (m, 2H), 1.58-1.43 (m, 2H), 1.37-1.19 (m, 2H), 0.87 (s, 9H, TBS), 0.08 (s, 3H, TBS), 0.01 (s, 3H, TBS); $^{13}$C NMR (125 MHz, CDCl$_3$) δ (major diastereomer) 200.7, 138.1, 117.8, 71.6, 50.0, 45.1, 44.7, 35.8, 32.8, 29.4, 26.0, 25.0, 18.2, −4.4, −4.5; HRMS: Exact mass calcd for C$_{17}$H$_{31}$BrClO$_2$Si [M−H]$^−$: 409.0965; found 409.0971 (FAB+).

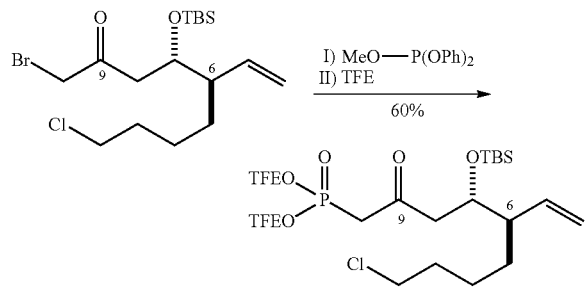

Bromoketone 8 (880 mg, 2.5:1 dr, 2.1 mmol, 1 equiv) and methyl-diphenylphosphite (686 µL, 3.2 mmol, 2 equiv) were combined together neat and heated to 140° C. After 7 h, aliquot $^1$H-NMR indicated full conversion of bromoketone 8 (this reaction time may vary depending on the scale of the reaction). The reaction mixture was cooled to 0° C. TFE (9.3 mL, 60 equiv), THF (4.7 mL), and DBU (479 µL, 3.2 mmol, 1.5 equiv) were added in that order. The reaction mixture was heated to 45° C. After 1 h, the reaction mixture was cooled to room temperature and filtered over a silica gel plug, eluting with 50% EtOAc/Hex (250 mL). The filtrate was concentrated and purified by silica gel flash column chromatography (2-20% EtOAc/Hex) affording TFE phosphonate 9 as a mixture of C6 diastereomers (732 mg, 2.5:1 dr, 60% combined yield). This material was used without further purification, and the separation of diastereomers was performed at a later stage. TLC R$_f$=0.4 (20% EtOAc/Hex); IR (thin film) 2932, 2859, 1718, 1294, 1259, 1169, 1069, 962, 836 cm$^{-1}$; $^1$H NMR (500 MHz, CDCl$_3$) δ 5.65-5.51 (m, 1H, C$_5$H), 5.15-4.96 (m, 2H, C$_4$H$_2$), 4.48-4.37 (m, 4H, TFE), 4.16 (app. td, J=6.1, 2.9 Hz, 1H, C$_7$H major), 4.09 (app. td, J=6.3, 4.7 Hz, 1H, C$_7$H minor), 3.51 (t, J=6.7 Hz, 2H, α-Cl), 3.34-3.17 (m, 2H, C$_{10}$H$_2$), 2.75-2.58 (m, 2H, C$_8$H$_2$), 2.14-2.01 (m, 1H, C$_6$H), 1.82-1.67 (m, 2H), 1.57-1.41 (m, 2H), 1.37-1.18 (m, 2H), 0.86 (s, 9H, TBS), 0.07 (s, 3H, TBS), 0.01 (s, 3H, TBS); $^{13}$C NMR (125 MHz, CDCl$_3$) δ (major diastereomer) 200.1 (d, $^2J_{C,P}$=7.0 Hz), 138.0, 122.6 (qd, J=277.6, 8.6 Hz, 2C), 117.8, 70.9, 62.6 (qd, J=38.1, 5.4 Hz), 62.5 (qd, J=38.1, 5.3 Hz), 49.9, 49.1 (d, $^3J_{C,P}$=5.4 Hz), 45.0, 42.7 (d, $^1J_{C,P}$=138.8 Hz), 32.8, 29.3, 25.9, 25.0, 18.1, −4.5, −4.6; HRMS: Exact mass calcd for C$_{21}$H$_{35}$ClF$_6$O$_5$PSi [M−H]$^−$: 575.1584; found 575.1602 (FAB+).

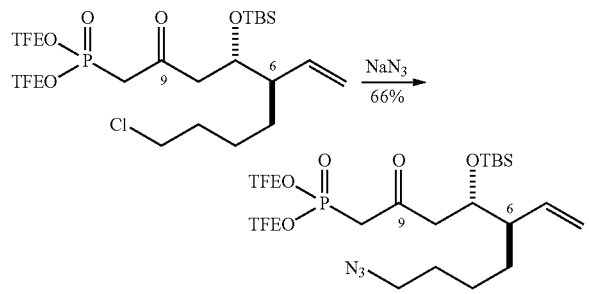

To a solution of chloride 9 (342 mg, 0.59 mmol, 1 equiv) in DMF (4 mL, 0.12M) was added sodium azide (46 mg, 0.71 mmol, 1.2 equiv). The reaction mixture was heated to 70° C. After 7 h, aliquot 1H-NMR indicated full conversion of starting material. The reaction mixture was allowed to cool to room temperature and directly purified by silica gel flash column chromatography (5-30% EtOAc/Hex) affording azide 10 as a mixture of C6 diastereomers (227 mg, 66% yield). This material was used without further purification, and the separation of diastereomers was performed at a later stage. TLC R$_f$=0.55 (30% EtOAc/Hex; product co-spots with starting material); IR (thin film) 2932, 2859, 2096, 1718, 1259, 1170, 1068, 836 cm$^{-1}$; $^1$H NMR (500 MHz, CDCl$_3$) δ (major diastereomer) 5.60 (ddd, J=17.2, 10.3, 9.0 Hz, 1H, C$_5$H), 5.13 (dd, J=10.3, 1.9 Hz, 1H, C$_4$H$_a$), 5.00 (dd, J=17.2, 1.9 Hz, 1H, C$_4$H$_b$), 4.50-4.37 (m, 4H, TFE), 4.16 (app. td, J=6.1, 2.9 Hz, 1H, C$_7$H), 3.29-3.21 (m, 4H, C$_{10}$H$_2$, α-N$_3$), 2.69-2.65 (m, 2H, C$_8$H$_2$), 2.06 (app. ddd, J=12.8, 6.4, 3.4 Hz, 1H, C$_6$H), 1.66-1.48 (m, 3H), 1.45-1.20 (m, 3H), 0.87 (s, 9H, TBS), 0.08 (s, 3H, TBS), 0.02 (s, 3H, TBS); $^{13}$C NMR (125 MHz, CDCl$_3$) δ (major diastereomer) 200.1 (d, $^2J_{C,P}$=6.9 Hz), 138.0, 122.6 (qd, J=277.5, 8.2 Hz, 2C), 117.9, 71.0, 62.6 (qd, J=38.0, 5.4 Hz), 62.5 (qd, J=37.9, 5.3 Hz), 51.5, 50.0, 49.2 (d, $^3J_{C,P}$=5.1 Hz), 42.8 (d, $^1J_{C,P}$=138.8 Hz), 30.0, 29.0, 25.9 (3C), 24.9, 18.2, −4.5, −4.5; LRMS: Exact mass calcd for C$_{21}$H$_{37}$F$_6$N$_3$O$_5$PSi [M+H]$^+$: 584.2; found 584.2 (FAB+).

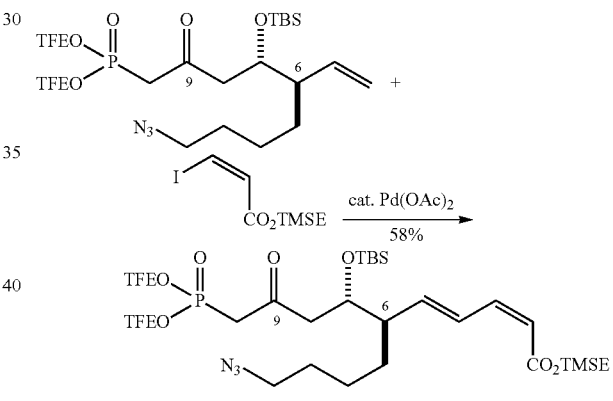

To a solution of phosphonate 10 (191 mg, 0.33 mmol, 1 equiv) and iodo-acrylate (195 mg, 0.65 mmol, 2 equiv) in MeCN (3.3 mL, 0.1M) was added AgOAc (109 mg, 0.65 mmol, 2 equiv) and Pd(OAc)$_2$ (2.2 mg, 0.0098 mmol, 3 mol %). The reaction mixture was heated to 45° C. Additional Pd(OAc)$_2$ was added at t=16 h (2.2 mg, 3 mol %) and t=24 h (1.1 mg, 1.5 mol %; total of 7.5 mol %). After a total reaction time of 40 h, the reaction mixture was cooled to room temperature and filtered over celite, eluting with 50% EtOAc/Hex (50 mL) The filtrate was washed with pH 7.0 buffer solution (20 mL). The aqueous layer was separated and extracted with 50% EtOAc/Hex (3×20 mL). The combined organic layers were dried over MgSO$_4$, filtered, and concentrated. Purification was accomplished by pH 7.0 buffered silica gel flash column chromatography (5-30% EtOAc/Hex) affording pure cis-dienoate 12 (74 mg, 30% yield) and a mixture of C6 epimers (68 mg, 28% yield; 58% combined yield). TLC R$_f$=0.50 (35% EtOAc/Hex); [α]$^{22}_D$ −4.0 (c=1.0, CH$_2$Cl$_2$); IR (thin film) 2953, 2858, 2096, 1713, 1254, 1172, 1069, 837 cm$^{-1}$; $^1$H NMR (500 MHz, CDCl$_3$) δ 7.35 (dd, J=15.5, 11.1 Hz, 1H, C$_4$H), 6.53 (t, J=11.3 Hz, 1H, C$_3$H), 5.84 (dd, J=15.5, 9.4 Hz, 1H, C$_5$H), 5.62 (d, J=11.3 Hz, 1H, C$_2$H), 4.49-4.39 (m, 4H, TFE), 4.24-4.17 (m, 3H, TMSE, C$_7$H), 3.34-3.20 (m, 2H, C$_{10}$H$_2$), 3.25 (t, J=6.9 Hz, 2H, α-N$_3$), 2.67 (app. d, J=6.1 Hz, 2H, C$_8$H$_2$), 2.26-2.19 (m, 1H, C$_6$H), 1.64-1.52 (m, 3H), 1.44-1.32 (m, 2H), 1.32-1.24 (m, 1H), 1.04-0.99 (m, 2H, TMSE), 0.87 (s, 9H, TBS), 0.09 (s, 3H, TBS), 0.05 (s, 9H, TMSE), 0.02 (s, 3H, TBS); $^{13}$C NMR (125 MHz, CDCl$_3$) δ 199.7 (d, $^2J_{C,P}$=6.9 Hz), 166.7, 144.3, 143.6, 129.6, 122.6 (qd, J=277.5, 8.1 Hz, 2C), 117.3, 70.7, 62.5 (app. qt, J=38.0, 5.9 Hz, 2C), 62.3, 51.4, 49.6 (d, $^3J_{C,P}$=4.9 Hz), 49.1, 42.7 (d, $^1J_{C,P}$=137.9 Hz), 30.3, 29.0, 26.0 (3C), 24.9, 18.2, 17.5, −1.4 (3C), −4.4, −4.6; LRMS: Exact mass calcd for C$_{29}$H$_{50}$F$_6$N$_3$NaO$_7$PSi$_2$ [M+Na]$^+$: 776.27; found 776.18 (FAB+).

Synthesis of C(6)-(4-azidobutyl) Analog

With a supply of fragment 12 in hand, its incorporation into the completed dictyostatin framework proved straightforward using our previously described synthesis (Scheme 2a). Thus, Still-Gennari-type coupling of 12 with previously described aldehyde 13 resulted in the isolation of pure Z-isomer 14 in 75% yield. Deprotection of the TMSE ester with tris(dimethylamino)-sulfonium difluorotrimethylsilicate (TAS-F) to give acid 15 was followed by macrolactonization using the Shiina method, leading to the isolation of macrolactone 16 in 54% overall yield from 13 (2 steps). Reduction of the C(9) ketone using the CBS protocol with catecholborane (Corey, E. J. et al. 1998) gave 17 in 79% yield. Finally, global silyl ether deprotection with unbuffered HF.pyridine delivered the targeted C(6)-(4-azidobutyl) analog 1 in 76% yield. Because we had previously prepared and stored a significant supply of aldehyde 13, this synthesis of 1 required just 10 total steps from 5, 3, and 6-chlorohex-1-ene.

Sxheme 2a.

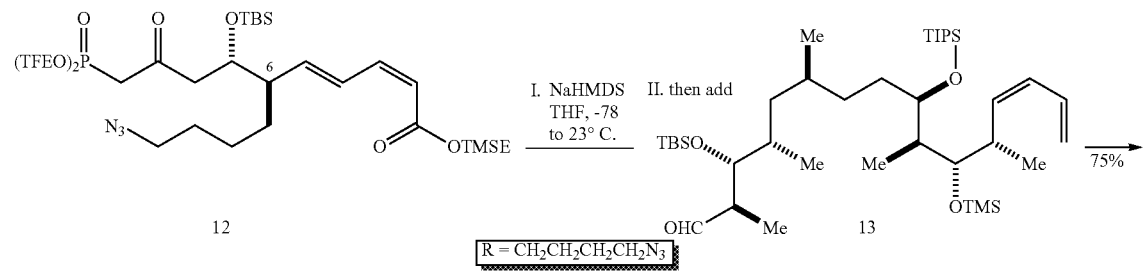

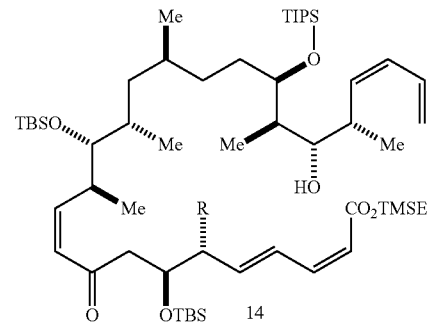

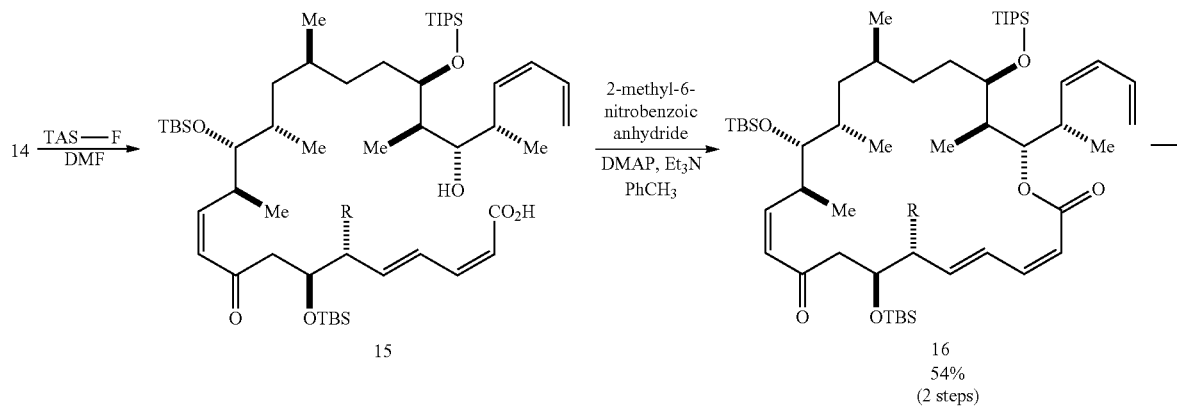

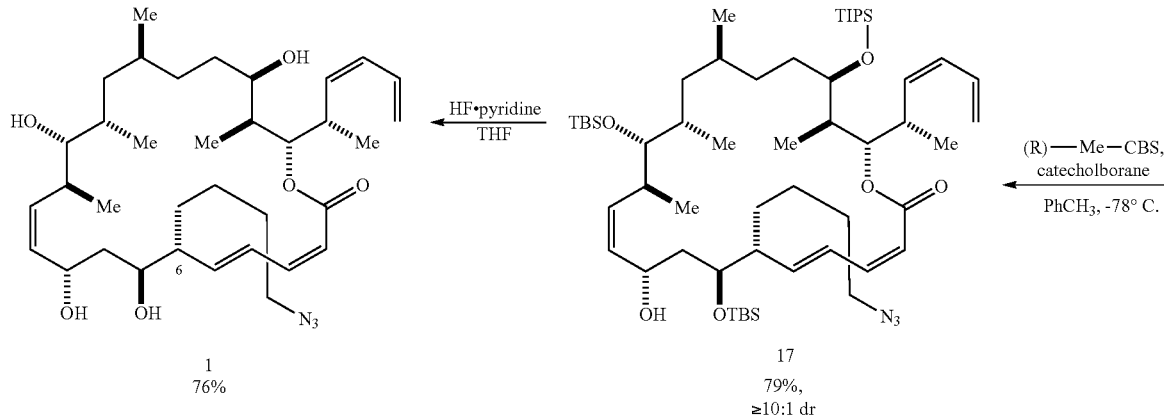

Experimentals

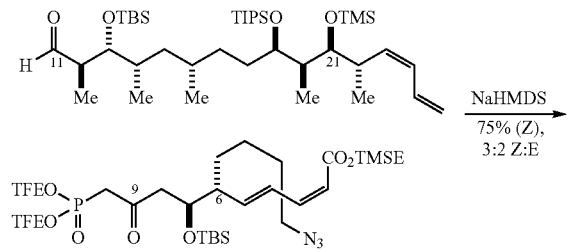

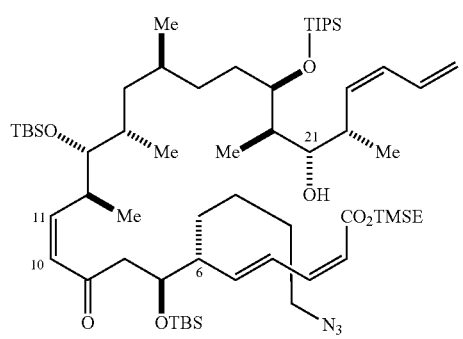

To a cooled (−78° C.) solution of phosphonate 12 (60 mg, 0.080 mmol, 1.5 equiv) in THF (1 mL, 0.05M) was added NaHMDS (1M THF, 69 µL, 0.069 mmol, 1.3 equiv). After 20 min, the aldehyde (37 mg, 0.053 mmol, 1 equiv) was added, and the reaction mixture was allowed to warm to room temperature. After 48 h, the reaction mixture was quenched at 0° C. with a solution of PPTS (5 mg) in MeOH (2 mL). After 2 h, the reaction mixture was diluted with pH 7.0 buffer solution (10 mL). The aqueous layer was separated and extracted with EtOAc (5×10 mL). The combined organic layers were dried over $MgSO_4$, filtered, and concentrated. Purification was accomplished by silica gel flash column chromatography (4% EtOAc/Hex) affording a 3:1 Z:E mixture of enone 14 (44 mg of Z-isomer, 75% yield of Z-isomer). TLC $R_f$=0.50 (10% EtOAc/Hex); $[\alpha]^{22}_D$ −14.7 (c=0.33, $CH_2Cl_2$); IR (thin film) 2930, 2862, 2095, 1713, 1637, 1604, 1461, 1251, 1172, 1059, 835, 774, 675 cm$^{-1}$; $^1$H NMR (500 MHz, $CDCl_3$) δ 7.37 (dd, J=15.5, 11.3 Hz, 1H, $C_4H$), 6.66 (dt, J=16.9, 10.6 Hz, 1H, $C_{25}H$), 6.57 (t, J=11.3 Hz, 1H, $C_3H$), 6.32 (dd, J=11.6, 9.7 Hz, 1H, $C_{11}H$), 6.09 (t, J=11.0 Hz, 1H, $C_{24}H$), 6.03 (d, J=11.7 Hz, 1H, $C_{10}H$), 5.94 (dd, J=15.5, 9.4 Hz, 1H, $C_5H$), 5.61 (d, J=11.3 Hz, 1H, $C_2H$), 5.49 (t, J=10.3 Hz, 1H, $C_{23}H$), 5.21 (dd, J=16.9, 2.0 Hz, 1H, $C_{26}H_a$), 5.12 (d, J=10.3 Hz, 1H, $C_{26}H_b$), 4.31 (td, J=6.0, 2.6 Hz, 1H, $C_7H$), 4.26-4.21 (m, 2H, TMSE), 4.01-3.93 (m, 1H, $C_{19}H$), 3.77-3.67 (m, 1H, $C_{12}H$), 3.60-3.56 (m, 1H, $C_{21}H$), 3.50 (app. t, J=3.4 Hz, 1H, $C_{13}H$), 3.26 (t, J=7.0 Hz, 2H, α-$N_3$), 2.88-2.80 (m, 1H, $C_{22}H$), 2.78 (d, J=1.7 Hz, 1H, OH), 2.61-2.50 (m, 2H, $C_8H_2$), 2.27-2.19 (m, 1H, $C_6H$); $^{13}$C NMR (125 MHz, $CDCl_3$) δ 199.3, 166.7, 152.5, 144.8, 144.6, 135.9, 132.6, 129.6, 129.3, 125.4, 117.6, 116.7, 79.9, 79.3, 78.5, 71.0, 62.2, 51.5, 50.1, 49.5, 41.2, 37.4, 36.5, 36.2, 36.1, 32.7, 31.9, 30.9, 30.9, 29.1, 26.3, 26.1, 25.0, 20.7, 19.3, 18.6, 18.5, 18.4, 18.2, 18.0, 17.6, 15.9, 13.6, 5.9, −1.3, −3.5, −3.8, −4.1, −4.6. HRMS: Exact mass calcd for $C_{61}H_{118}N_3O_7Si_4$ [M+H]$^+$: 1116.8047; found 1116.7997 (TOF MS ASAP+).

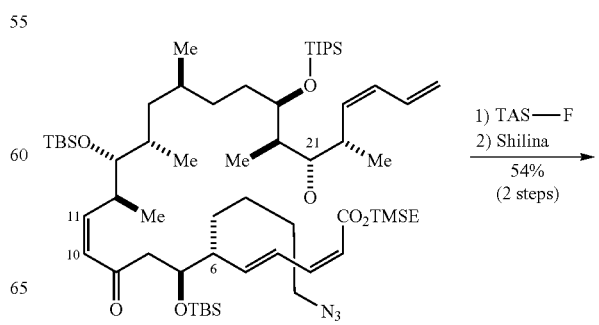

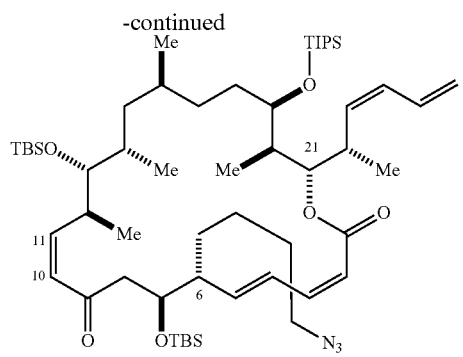

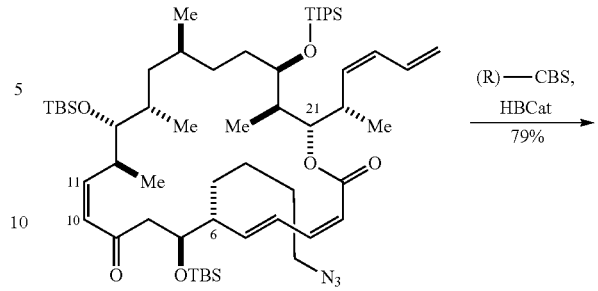

C1 Deprotection: To a cooled (0° C.) solution of TMSE ester14 (44 mg, 0.039 mmol, 1 equiv) in DMF (3.9 mL, 0.01M) was added a solution of TAS-F (11 mg, 0.041, 1.05 equiv) in DMF (0.5 mL) dropwise. The reaction mixture was allowed to warm to room temperature. After 20 h, the reaction mixture was diluted with $Et_2O$ (10 mL) and quenched at 0° C. with 1M $NaHSO_4$ (5 mL). The reaction mixture was further diluted with saturated aqueous NaCl (5 mL) and extracted with $Et_2O$ (5×10 mL). The combined organic layers were dried over $MgSO_4$, filtered, and concentrated to afford acid 15, which was used immediately without purification.

Macrolactonization: To a solution of crude acid 15 in Toluene (39 mL, 0.001M) was added 2-methyl-6-nitrobenzoic anhydride (41 mg, 0.12 mmol, 3 equiv), DMAP (5 mg, 0.039 mmol, 1 equiv), and $NEt_3$ (55 μL, 0.39 mmol, 10 equiv). After 24 h, the reaction mixture was quenched with saturated aqueous $NaHCO_3$ (20 mL) The aqueous layer was separated and extracted with EtOAc (3×50 mL). The combined organic layers were dried over $MgSO_4$, filtered, and concentrated. Purification was accomplished by pH 7.0 buffered silica gel flash column chromatography (1-5% EtOAc/Hex) affording macrocycle 16 (21 mg, 54% yield over 2 steps). TLC $R_f$=0.52 (10% EtOAc/Hex); $[\alpha]^{19}_D$ −9.7 (c=1.0, $CH_2Cl_2$); IR (thin film) 2931, 2864, 2096, 1707, 1462, 1380, 1255, 1051, 836, 775 $cm^{-1}$; $^1H$ NMR (500 MHz, $CDCl_3$) δ 7.13 (dd, J=15.6, 11.1 Hz, 1H, $C_4H$), 6.62-6.52 (m, 2H, $C_{25}H$, $C_3H$), 6.38 (dd, J=11.7, 10.2 Hz, 1H, $C_{11}H$), 6.09 (d, J=11.7 Hz, 1H, $C_{10}H$), 6.04 (t, J=11.2 Hz, 1H, $C_{24}H$), 5.91 (dd, J=15.5, 9.0 Hz, 1H, $C_5H$), 5.61 (d, J=11.6 Hz, 1H, $C_2H$), 5.47 (t, J=10.8 Hz, 1H, $C_{23}H$), 5.36 (dd, J=9.1, 2.9 Hz, 1H, $C_{21}H$), 5.21 (d, J=16.8 Hz, 1H, $C_{26}H_a$), 5.13 (d, J=10.6 Hz, 1H, $C_{26}H_b$), 4.17-4.11 (m, 1H, $C_7H$), 3.89-3.80 (m, 1H, $C_{19}H$), 3.80-3.69 (m, 1H, $C_{12}H$), 3.32 (dd, J=5.7, 2.0 Hz, 1H, $C_{13}H$), 3.26 (t, J=7.0 Hz, 2H, α-$N_3$), 3.19-3.11 (m, 1H, $C_{22}H$), 2.61 (dd, J=13.8, 6.8 Hz, 1H, $C_8H_a$), 2.45 (dd, J=13.8, 4.9 Hz, 1H, $C_8H_b$), 2.13 (m, 1H, $C_6H$); $^{13}C$ NMR not included due to rotamers causing significant line broadening; LRMS: Exact mass calcd for $C_{53}H_{103}N_3NaO_6Si_3$ $[M+Na]^+$: 1020.7; found 1020.8 (FAB+).

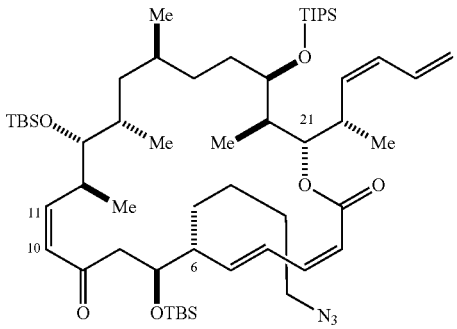

To a cooled (−78° C.) solution of enone 16 (18 mg, 18 μmol, 1 equiv) in Toluene (360 μL, 0.05M) was added (R)-2-Methyl-CBS oxazaborolidine (1M Tol, 90 μL, 90 μmol, 5 equiv) and catecholborane (50% w/w Toluene, 50 μL, 0.18 mmol, 10 equiv). After 24 h at −78° C., the reaction mixture was quenched with MeOH (2 mL), followed by saturated aqueous $NaHCO_3$ (2 mL). The aqueous layer was separated and extracted with $Et_2O$ (5×10 mL). The combined organic layers were dried over $MgSO_4$, filtered, and concentrated. Purification was accomplished by silica gel flash column chromatography (5-10% EtOAc/Hex) affording allylic alcohol 17 (14 mg, 79% yield). TLC $R_f$=0.32 (10% EtOAc/Hex); $[E]^{22}_D$ −114 (c=0.1, $CH_2Cl_2$); IR (thin film) 3492, 2930, 2863, 2096, 1711, 1462, 1254, 1052, 836, 775, 678 $cm^{-1}$; $^1H$ NMR (500 MHz, $CDCl_3$) δ 7.04 (dd, J=15.4, 11.4 Hz, 1H, $C_4H$), 6.57 (dt, J=16.9, 10.5 Hz, 1H, $C_{25}H$), 6.52 (t, J=11.4 Hz, 1H, $C_3H$), 6.06 (t, J=11.1 Hz, 1H, $C_{24}H$), 5.98 (dd, J=15.7, 7.6 Hz, 1H, $C_5H$), 5.69 (t, J=9.9 Hz, 1H, $C_{11}H$), 5.60 (d, J=11.4 Hz, 1H, $C_2H$), 5.43-5.35 (m, 2H, $C_{23}H$, $C_{10}H$), 5.28-5.17 (m, 2H, $C_{21}H$, $C_{26}H_a$), 5.09 (d, J=9.6 Hz, 1H, $C_{26}H_b$), 4.55 (t, J=9.5 Hz, 1H, $C_9H$), 4.05 (dt, J=9.9, 2.9 Hz, 1H, $C_7H$), 3.77 (bs, 1H, $C_{19}H$), 3.23 (m, 3H, $C_{13}H$, α-$N_3$), 3.08 (bs, 1H, $C_{22}H$), 2.73-2.64 (m, 1H, $C_{12}H$), 2.31 (bs, 1H, $C_6H$), 1.86 (bs, 1H, $C_{20}H$); $^{13}C$ NMR not included due to rotamers causing substantial line broadening; HRMS: Exact mass calcd for $C_{56}H_{104}N_3O_5Si_3$ $[M+H-H_2O]^+$: 982.7284; found 982.7284 (TOF MS ASAP+).

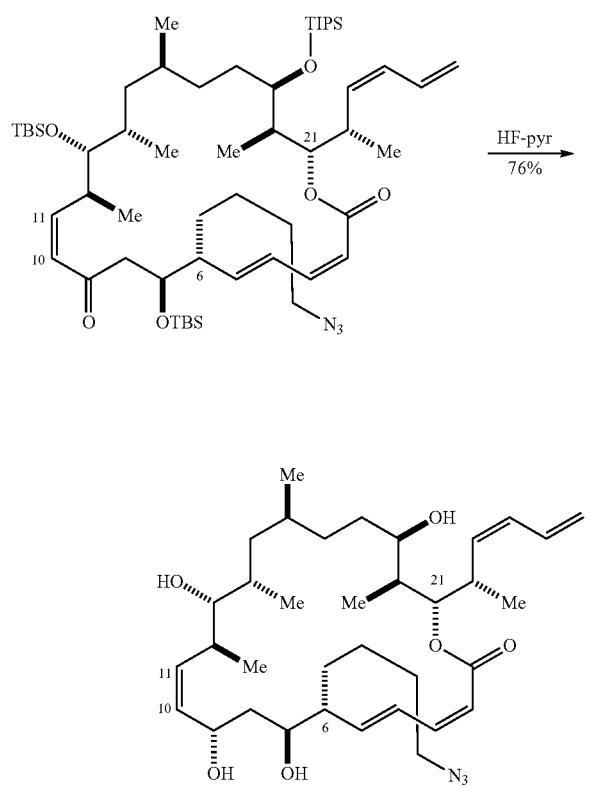

To a cooled (0° C.) solution of 17 (14 mg) in THF (2 mL) in a Nalgene tube was added HF-pyridine (100 μL). The reaction mixture was allowed to warm to room temperature. At t=24 h, 48 h, and 60 h, additional HF-pyridine (100 μL; total of 400 μL) was added. After a total reaction time of 90 h, the reaction mixture was slowly quenched at 0° C. with saturated aqueous NaHCO$_3$ (10 mL) and then diluted with CH$_2$Cl$_2$ (20 mL). The aqueous layer was separated and extracted with CH$_2$Cl$_2$ (5×20 mL). The combined organic layers were dried over MgSO$_4$, filtered, and concentrated. Purification was accomplished by silica gel flash column chromatography (50-100% EtOAc/Hex) affording 1 (6.5 mg, 76% yield). TLC R$_f$=0.48 (80% EtOAc/Hex); [α]$^{18D}$ 48.5 (c=0.1, CH$_2$Cl$_2$); IR (thin film) 3403, 2925, 2096, 1694, 1456, 1277, 1042, 961 cm$^{-1}$; $^1$H NMR (500 MHz, CDCl$_3$) δ 7.34 (dd, J=15.8, 11.3 Hz, 1H, C$_4$H), 6.64-6.55 (m, 1H, C$_{25}$H), 6.49 (t, J=11.3 Hz, 1H, C$_3$H), 6.02 (dd, J=15.9, 7.4 Hz, 1H, C$_5$H), 5.99 (t, J=11.0 Hz, 1H, C$_{24}$H), 5.57 (t, J=10.2 Hz, 1H, C$_{10}$H), 5.49 (d, J=11.3 Hz, 1H, C$_2$H), 5.34 (t, J=10.5 Hz, 1H, C$_{11}$H), 5.26 (t, J=10.5 Hz, 1H, C$_{23}$H), 5.18 (dd, J=16.9, 1.9 Hz, 1H, C$_{26}$H$_a$), 5.10 (d, J=10.1 Hz, 1H, C$_{26}$H$_b$), 4.94 (dd, J=8.2, 2.6 Hz, 1H, C$_{21}$H), 4.81 (dt, J=10.4, 5.7 Hz, 1H, C$_9$H), 4.01-3.96 (m, 1H, C$_7$H), 3.51-3.46 (m, 1H, C$_{19}$H), 3.30-3.24 (m, 3H, C$_{13}$H, α-N$_3$), 3.04-2.94 (m, 1H, C$_{22}$H), 2.81-2.70 (m, 1H, C$_{12}$H), 2.27-2.20 (m, 1H, C$_6$H), 1.91-1.83 (m, 1H, C$_{20}$H), 1.06 (d, J=6.8 Hz, 3H, C$_{20}$CH$_3$), 1.00 (d, J=6.7 Hz, 3H, C$_{22}$CH$_3$), 0.94 (app. t, J=6.5 Hz, 6H, C$_{12}$CH$_3$, C$_{14}$CH$_3$), 0.90 (d, J=6.4 Hz, 3H, C$_{16}$CH$_3$); $^{13}$C NMR (125 MHz, CDCl$_3$) δ 166.7, 145.7, 145.2, 134.9, 134.0, 133.0, 132.2, 130.3, 128.5, 118.1, 116.3, 76.3, 76.2, 73.3, 70.1, 66.5, 51.5, 47.5, 42.4, 40.0, 38.9, 35.3, 35.3, 32.1, 31.6, 31.4, 29.9, 29.5, 29.3, 24.5, 21.3, 17.8, 17.6, 14.2, 10.4; HRMS: Exact mass calcd for C$_{35}$H$_{55}$N$_3$NaO$_5$ [M+Na-H$_2$O]$^+$: 620.4039; found 620.4043 (TOF MS ES+).

Synthesis of C(12)-(4-azidobutyl) Analog

To incorporate the 4-azidobutyl group at C(12), we adapted our recently reported two pot/three step protocol for the rapid synthesis of stereotriads (Foley, C. N. et al. 2014). Thus, silylformylation of 6-chlorohex-1-yne gave aldehyde 18 which was directly crotylated with (S,S)-cis EZCrotyl-Mix (Kim, H. et al. 2011) to give 19 in 90% yield and 95% ee (Scheme 3a). Tamao oxidation/anti-diastereoselective tautomerization proceeded smoothly and with 10:1 diastereoselectivity, and following protection of the aldehyde, 20 was isolated in 66% yield over two steps. The remainder of the fragment synthesis followed our dictyostatin synthesis with the added azide displacement step, and produced, by way of intermediates 21, 22, and 23, iodide 24. Iodide 24 was then used to produce the C(12)-(4-azidobutyl) analog of dictyostatin 2 according to previously described dictyostatin synthesis (Ho, S. et al. 2013).

Scheme 3a.

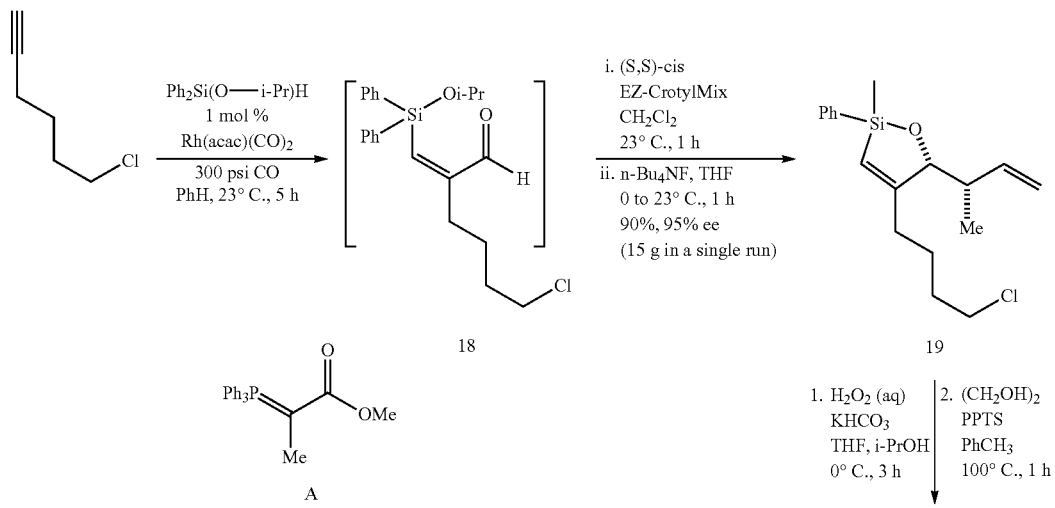

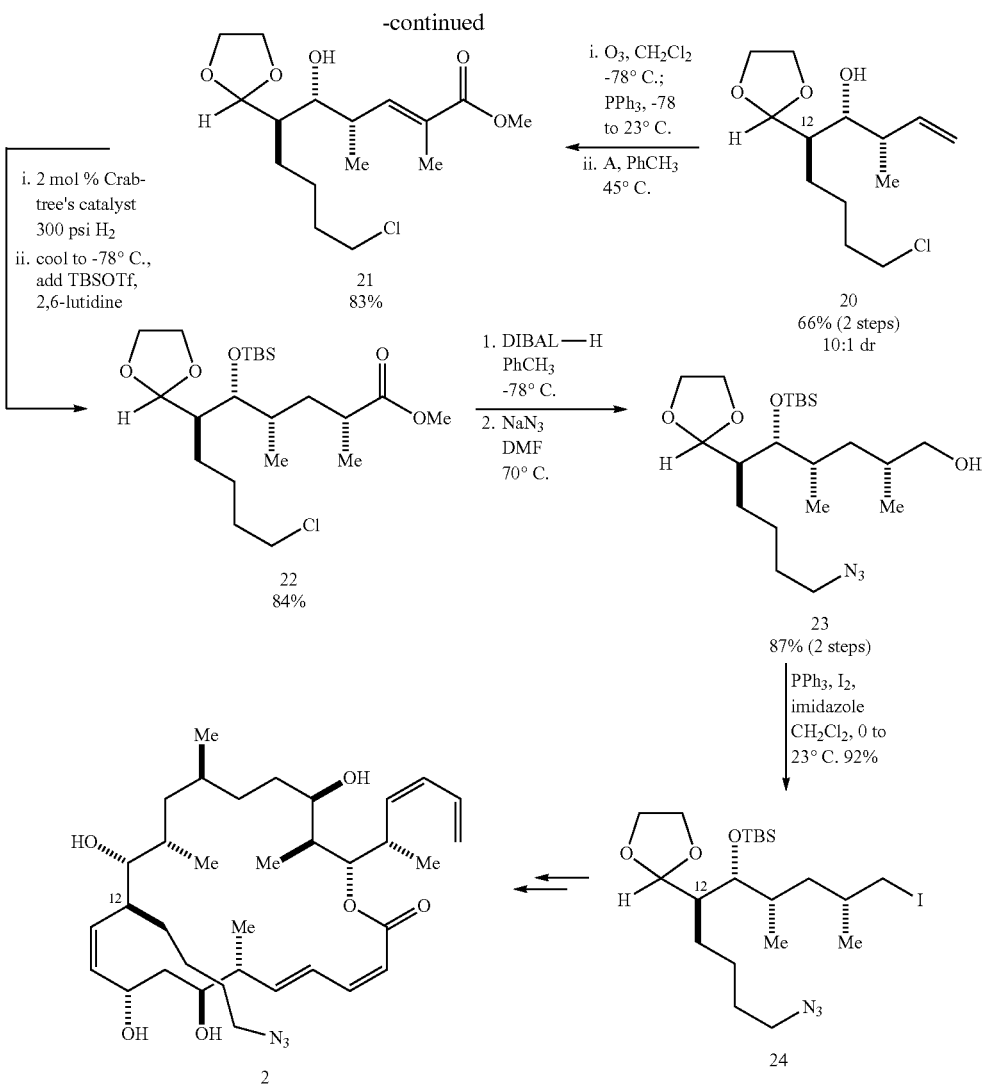

Experimentals

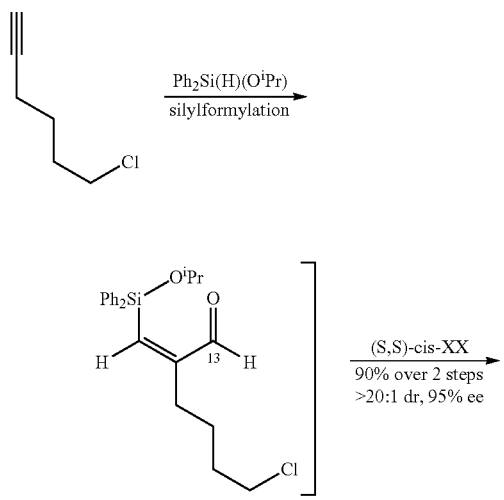

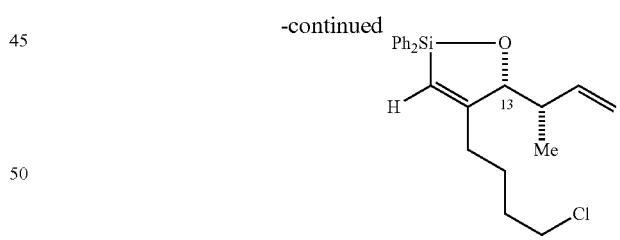

Silylformylation: To the glass liner of a Parr bomb was added 6-chloro-1-hexyne (5.0 g, 43 mmol, 1 equiv), diphenyl-isopropoxy-silane (10 g, 4.3 mmol, 1 equiv), and benzene (43 mL, 1M). The glass liner was cooled to −78° C., and Rh(acac)(CO)$_2$ (111 mg, 0.043 mmol, 1 mol %) was added on top of the frozen benzene solution. While frozen, the glass liner was quickly placed into the Parr bomb, which was then charged to 250 psi with CO (vented and re-charged 3×). After 6 h, aliquot $^1$H-NMR indicated full conversion of 6-chloro-1-hexyne to aldehyde 18. The reaction mixture was concentrated and aldehyde 18 was used immediately without purification.

Crotylation: To a solution of crude aldehyde 18 in CH$_2$Cl$_2$ (214 mL, 0.2M) was added (S,S)-cis-crotylsilane (27 g, 47 mmol, 1.1 equiv), followed by Sc(OTf)$_3$ (633 mg, 1.3 mmol, 3 mol %). After vigorously stirring for 3 h, the reaction mixture was quenched at 0° C. with TBAF (47 mL, 1M THF) and allowed to warm to room temperature. After 1 h, the reaction mixture was concentrated and filtered over a plug of silica gel, eluting with 50% EtOAc/Hex (2 L). The filtrate was then concentrated and purified by silica gel flash column chromatography (1-5% EtOAc/Hex) affording vinylsilane 19 (15 g, 90% yield over 2 steps). The enantiomeric excess of 19 was determined to be 95% ee by $^1$H NMR of the derived (R)-MTPA Mosher ester of the acetal.

Aldehyde 18: $^1$H NMR (400 MHz, CDCl$_3$) δ 10.02 (s, 1H, CHO), 7.65-7.60 (m, 4H), 7.49-7.36 (m, 6H), 7.08 (t, J=1.3 Hz, 1H, C$_{11}$H), 4.13 (hept, J=6.1 Hz, 1H, -OiPr), 3.55 (t, J=6.6 Hz, 2H, α-Cl), 2.41 (td, J=7.7, 1.3 Hz, 2H), 1.86-1.77 (m, 2H), 1.71-1.60 (m, 2H), 1.16 (d, J=6.1 Hz, 6H).

Vinylsilane 19: TLC R$_f$=0.6 (10% EtOAc/Hex); [α]$^{19}_D$ -20.7 (c=2.0, CH$_2$C$_{12}$); IR (thin film) 3068, 2934, 1580, 1428, 1113, 996, 822, 739, 699 cm$^{-1}$; $^1$H NMR (500 MHz, CDCl$_3$) δ 7.66-7.63 (m, 2H), 7.53-7.50 (m, 2H), 7.47-7.32 (m, 6H), 6.09 (ddd, J=16.5, 9.8, 6.7 Hz, 1H, C$_{15}$H), 6.05 (d, J=1.7 Hz, 1H, C$_{11}$H), 5.14-5.05 (m, 2H, C$_{16}$H$_2$), 4.87 (t, J=2.1 Hz, 1H, C$_{13}$H), 3.59 (t, J=6.4 Hz, 2H, α-Cl), 2.59-2.52 (m, 1H, C$_{14}$H), 2.31-2.16 (m, 2H), 1.91-1.84 (m, 2H), 1.84-1.76 (m, 2H), 0.76 (d, J=6.9 Hz, 3H, C$_{14}$CH$_3$); $^{13}$C NMR (125 MHz, CDCl$_3$) δ 167.0, 142.6, 135.8, 135.1, 135.0, 134.7, 130.2, 127.9, 127.9, 119.2, 114.0, 88.3, 45.0, 40.9, 32.4, 31.5, 25.0, 12.3; HRMS: Exact mass calcd for C$_{23}$H$_{26}$OClSi [M–H]$^-$: 381.1441; found 381.1448 (FAB+).

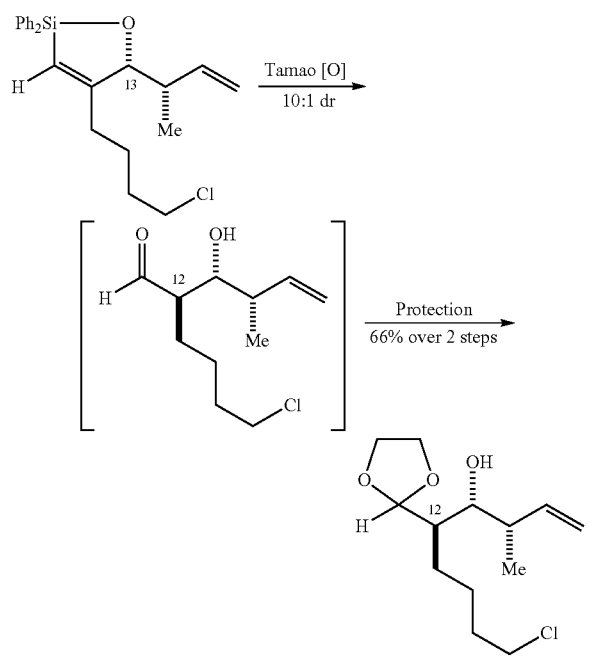

Tamao oxidation: To a cooled (0° C.) solution of vinylsilane 19 (2.5 g, 6.5 mmol, 1 equiv) in 1:1 THF/iPrOH (65 mL, 0.1M) was added KHCO$_3$ (686 mg, 6.9 mmol, 1.05 equiv), followed by H$_2$O$_2$ (8.5 mL, 85 mmol, 13 equiv, 30% wt in H$_2$O). After 3 h at 0° C., the reaction mixture was quenched with H$_2$O (20 mL). The aqueous layer was separated and extracted with CH$_2$Cl$_2$ (3×20 mL). The combined organic layers were dried over MgSO$_4$, filtered, and concentrated to afford the corresponding aldehyde, which was used immediately without purification. Protection: To a solution of crude aldehyde in Toluene (65 mL, 0.1M) was added ethylene glycol (3.7 mL, 65 mmol, 10 equiv) and PPTS (1.6 g, 6.5 mmol, 1 equiv). The reaction mixture was heated to 100° C. After 1 h, the reaction mixture was cooled to room temperature and concentrated to ca. 10 mL. Purification was accomplished by silica gel flash column chromatography affording dioxolane 20 as a mixture of C12 diastereomers (1.14 g, 10:1 dr, 66% combined yield). This material was used without further purification, and the separation of diastereomers was performed at a later stage.

Aldehyde: $^1$H NMR (400 MHz, CDCl$_3$) δ 9.77 (d, J=2.5 Hz, 1H, CHO), 5.78-5.66 (m, 1H, C$_{15}$H), 5.13-5.06 (m, 2H, C$_{16}$H$_2$), 3.64 (t, J=5.9 Hz, 1H, C$_{13}$H), 3.53 (t, J=6.5 Hz, 2H, α-Cl), 2.60-2.53 (m, 1H, C$_{12}$H), 2.47-2.40 (m, 1H, C$_{14}$H), 1.84-1.72 (m, 2H), 1.65-1.44 (m, 4H), 1.09 (d, J=6.8 Hz, 3H, C$_{14}$CH$_3$).

Acetal 20: TLC R$_f$=0.38 (25% EtOAc/Hex); IR (thin film) 3523 (bs), 2877, 1639, 1458, 1406, 1100, 999, 915 cm$^{-1}$; $^1$H NMR (500 MHz, CDCl$_3$) δ 5.74 (ddd, J=17.3, 10.4, 8.1 Hz, 1H, C$_{15}$H), 5.12-4.93 (m, 3H, C$_{16}$H$_2$, C$_{11}$H), 4.06-3.94 (m, 2H), 3.93-3.80 (m, 2H), 3.54 (td, J=6.7, 1.5 Hz, 2H, α-Cl), 3.49 (dd, J=7.5, 4.8 Hz, 1H, C$_{13}$H), 2.82 (bs, 1H, OH), 2.40 (app. hept, J=7.0 Hz, 1H, C$_{14}$H), 2.00-1.94 (m, 1H, C$_{12}$H), 1.83-1.72 (m, 2H), 1.64-1.40 (m, 4H), 1.10 (d, J=6.7, 3H, C$_{14}$CH$_3$); $^{13}$C NMR (125 MHz, CDCl$_3$) δ 141.7, 114.9, 104.9, 75.0, 65.2, 64.8, 45.1, 42.5, 42.2, 33.1, 24.9, 24.8, 16.2; HEMS: Exact mass calcd for C$_{13}$H$_{22}$O$_3$Cl [M–H]$^-$: 261.1257; found 261.1269 (FAB+).

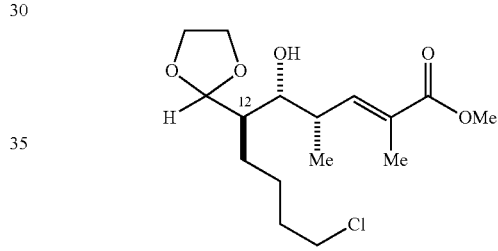

To a cooled (−78° C.) solution of 20 (1.0 g, 10:1 dr, 3.8 mmol, 1 equiv) in CH$_2$Cl$_2$ (38 mL, 0.1M) was bubbled in ozone. Immediately after the solution began turning blue, the reaction mixture was purged with oxygen until colorless. PPh$_3$ (1.1 g, 4.2 mmol, 1.1 equiv) was added, and the reaction mixture was allowed to warm to room temperature. After 12 h, the reaction mixture was diluted with Toluene (38 mL).

Freshly prepared phosphonium A (1.6 g, 4.6 mmol, 1.2 equiv) was added, and the reaction mixture was heated to 45° C. After 5 h, additional phosphonium (1.6 g, 1.2 equiv) was added. After a total reaction time of 24 h, the reaction mixture was cooled to room temperature and concentrated to ca. 10 mL. Purification was accomplished by silica gel flash column chromatography (10-40% EtOAc/Hex) affording methyl ester 21 (1.05 g, 10:1 dr, 83% combined yield). This material was used without further purification, and the separation of diastereomers was performed at a later stage. TLC R$_f$=0.37 (30% EtOAc/Hex); IR (thin film) 3515 (bs), 2951, 2873, 1710, 1436, 1273, 1225, 1123, 1101, 988, 752 cm$^{-1}$; $^1$H NMR (500 MHz, CDCl$_3$) δ 6.59 (dd, J=10.2, 1.5 Hz, 1H, C$_{15}$H), 4.89 (d, J=3.3 Hz, 1H, C$_{11}$H, 4.04-3.92 (m, 2H), 3.92-3.80 (m, 2H), 3.72 (s, 3H, CO$_2$Me), 3.58-3.48 (m, 3H, C$_{13}$H, α-Cl), 2.93 (d, J=7.4 Hz, 1H, OH), 2.80-2.66 (m, 1H, C$_{14}$H), 1.85 (d, J=1.5 Hz, 3H, C$_{16}$CH$_3$), 1.83-1.68 (m, 3H, C$_{12}$H), 1.59-1.42 (m, 4H), 1.09 (d, J=6.6 Hz, 3H, Cl$_2$CH$_3$); $^{13}$C NMR (125 MHz, CDCl$_3$) δ 168.6, 144.3, 127.0, 104.9, 75.0, 65.1, 64.7, 51.8, 44.9, 43.3, 37.9, 32.9, 25.3, 24.6, 16.1, 12.7; HRMS: Exact mass calcd for $C_{16}H_{26}ClO_5$ [M–H]⁻: 333.1469; found 333.1481 (FAB+).

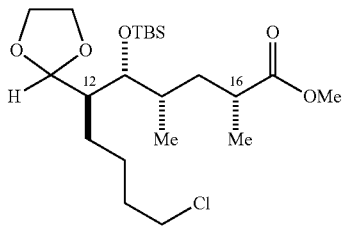 [SMILES: COC(=O)[C@H](C)C[C@H](C)[C@@H](O[Si](C)(C)C(C)(C)C)[C@@H](CCCCCl)C1OCCO1]

To the glass liner of a Parr bomb was added 21 (1.1 g, 3.3 mmol, 1 equiv) and $CH_2Cl_2$ (8.2 mL, 0.4M). The Parr bomb was charged with $H_2$ (300 psi) and stirred overnight in order to saturate the solution. Then, Crabtree's catalyst (53 mg, 0.066 mmol, 2 mol %) was added, and the bomb was charged to 300 psi with H2. After 20 h, additional Crabtree's catalyst (12 mg) was added. After a total reaction time of 36 h, aliquot ¹H-NMR indicated full conversion of the major C12 diastereomer; the minor C12 diastereomer was not appreciably reduced. The glass liner was removed from the bomb and cooled to –78° C. 2,6-lutidine (1.5 mL, 13 mmol, 4 equiv) and TBS-OTf (1.5 mL, 6.6 mmol, 2 equiv) were added, and the reaction mixture was allowed to warm to 0° C. as the dry ice bath expired. After 4 h, the reaction mixture was quenched with saturated aqueous $NH_4Cl$ (50 mL). The aqueous layer was separated and extracted with $CH_2Cl_2$ (3×50 mL). The combined organic layers were dried over $MgSO_4$, filtered, and concentrated. Purification was accomplished by silica gel flash column chromatography (2-5% EtOAc/Hex) affording a mixture of product 22 and the minor C12 diastereomer starting material (1.25 g, 84% combined yield). This material was used without further purification, and the separation was performed at a later stage. TLC $R_f$=0.33 (10% EtOAc/Hex); IR (thin film) 2953, 2931, 1736, 1461, 1253, 1059, 835, 773 cm⁻¹; ¹H NMR (500 MHz, $CDCl_3$) δ 4.84 (d, J=4.0 Hz, 1H, $C_{11}$H), 3.98-3.89 (m, 2H), 3.84-3.76 (m, 2H), 3.69 (dd, J=5.9, 2.4 Hz, 1H, $C_{13}$H), 3.65 (s, 3H), 3.52 (t, J=6.7 Hz, 2H, α-Cl), 2.60-2.45 (m, 1H, $C_{16}$H), 1.85-1.78 (m, 1H, $C_{12}$H), 1.78-1.64 (m, 4H), 1.61-1.39 (m, 5H, $C_{15}H_a$), 1.24 (m, 1H, Cl$_5$H$_b$), 1.15 (d, J=6.9 Hz, 3H, $C_{16}CH_3$), 0.89 (s, 9H, TBS), 0.88 (d, J=6.9 Hz, 3H, $C_{14}CH_3$), 0.06 (s, 3H, TBS), 0.05 (s, 3H, TBS); ¹³C NMR (125 MHz, $CDCl_3$) δ 177.4, 105.2, 75.7, 64.9, 64.5, 51.6, 46.9, 45.1, 40.3, 37.5, 34.0, 33.4, 26.6, 26.3, 25.1, 18.6, 18.1, 14.5, –4.0, –4.0; HRMS: Exact mass calcd for $C_{22}H_{42}ClO_5Si$ [M–H]⁻: 449.2490; found 449.2479 (FAB+).

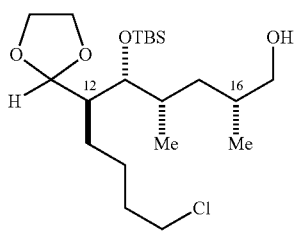

To a cooled (–78° C.) solution of ester 22 (1.25 g, 2.8 mmol, 1 equiv) in Toluene (28 mL, 0.1M) was added DIBAL (1M Hex, 7.6 mL, 7.6 mmol, 2.7 equiv) dropwise. After 4 h, the reaction mixture was quenched with MeOH (10 mL), followed by a saturated aqueous solution of Rochelle's salt (50 mL). After vigorously stirring for 1 h, the aqueous layer was separated and extracted with 50% EtOAc/Hex (3×50 mL). The combined organic layers were dried over $MgSO_4$, filtered, and concentrated. Purification was accomplished by silica gel flash column chromatography (10-20% EtOAc/Hex) affording pure reduced alcohol (1.04 g, 89% yield). TLC $R_f$=0.47 (39% EtOAc/Hex); $[α]^{21}_D$ –10.2 (c=0.8, $CH_2Cl_2$); IR (thin film) 3393 (bs), 2928, 2857, 1462, 1251, 1059, 834, 772 cm⁻¹; ¹H NMR (500 MHz, $CDCl_3$) δ 4.85 (d, J=4.4 Hz, 1H, $C_{11}$H), 3.97-3.90 (m, 2H), 3.84-3.77 (m, 2H), 3.65 (dd, J=5.0, 3.4 Hz, 1H, $C_{13}$H), 3.53 (t, J=6.7 Hz, 2H, α-Cl), 3.50 (dd, J=10.8, 4.4 Hz, 1H, $C_{17}H_a$), 3.45 (dd, J=10.8, 6.0 Hz, 1H, $C_{17}H_b$), 1.89-1.66 (m, 5H, $C_{12}$H, $C_{14}$H, β-Cl, $C_{16}$H), 1.57-1.37 (m, 5H, $C_{15}H_a$), 0.98-0.93 (m, 1H, $C_{15}H_b$), 0.94 (d, J=6.7 Hz, 2H, $C_{16}CH_3$), 0.90 (s, 9H, TBS), 0.89 (d, J=6.8 Hz, 3H, $C_{14}CH_3$), 0.06 (s, 3H, TBS), 0.05 (s, 3H, TBS); ¹³C NMR (125 MHz, $CDCl_3$) δ 105.3, 75.8, 67.6, 64.8, 64.5, 46.8, 45.1, 39.0, 33.3, 33.3, 33.1, 26.6, 26.3, 25.5, 18.6, 18.0, 15.8, –3.8, –3.9; HRMS: Exact mass calcd for $C_{21}H_{43}ClNaO_4Si$ [M+Na]⁺: 445.2517; found 445.2517 (FAB+).

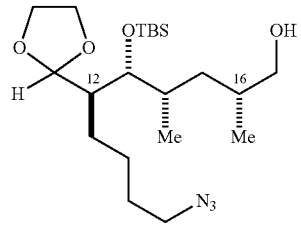

To a solution of the alcojol (120 mg, 0.28 mmol, 1 equiv) in DMF (1.9 mL, 0.15M) was added $NaN_3$ (20 mg, 0.31 mmol, 1.1 equiv). The reaction mixture was heated to 70° C. After 6 h, aliquot ¹H NMR indicated full conversion of starting material. The reaction mixture was allowed to cool to room temperature and directly purified by silica gel flash column chromatography (5-20% EtOAc/Hex) affording azide 23 (120 mg, 98% yield). TLC $R_f$=0.47 (39% EtOAc/Hex; product co-spots with starting material); $[α]^{18}_D$ –5.9 (c=2.0, $CH_2Cl_2$); IR (thin film) 3359 (bs), 2929, 2858, 2094, 1462, 1252, 1063, 835, 773 cm⁻¹; ¹H NMR (500 MHz, $CDCl_3$) δ 4.85 (d, J=4.4 Hz, 1H, $C_{11}$H), 3.98-3.89 (m, 2H), 3.84-3.77 (m, 2H), 3.66 (dd, J=5.1, 3.3 Hz, 1H, Cl$_3$H), 3.50 (dd, J=10.8, 4.5 Hz, 1H, $C_{17}H_a$), 3.46 (dd, J=10.8, 6.0 HZ, 1H, $C_{17}H_b$), 3.26 (t, J=6.9 Hz, 2H, α-$N_3$), 1.88-1.77 (m, 2H, $C_{12}$H, $C_{14}$H), 1.74-1.66 (m, 1H, $C_{16}$H), 1.63-1.57 (m, 2H, β-$N_3$), 1.53-1.38 (m, 5H, $C_{15}H_a$), 0.98-0.93 (m, 1H, $C_{15}H_b$), 0.94 (d, J=6.7 Hz, 3H, C$_{16}$CH$_3$), 0.90 (s, 9H, TBS), 0.89 (d, J=6.9 Hz, 3H, Cl$_4$CH$_3$), 0.06 (s, 3H, TBS), 0.05 (s, 3H, TBS); $^{13}$C NMR (125 MHz, CDCl$_3$) δ 105.3, 75.8, 67.6, 64.8, 64.5, 51.5, 46.9, 39.0, 33.3, 33.1, 29.5, 26.5, 26.3, 25.8, 18.6, 18.0, 15.9, −3.8, −3.9; HRMS: Exact mass calcd for C$_{21}$H$_{44}$N$_3$O$_4$Si [M+H]+: 430.3101; found 430.3109 (FAB+).

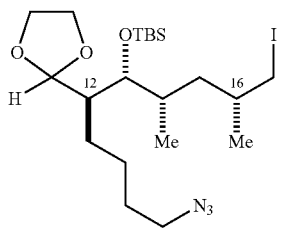

To a cooled (0° C.) solution of PPh$_3$ (714 mg, 2.7 mmol, 1.8 equiv) and imidazole (515 mg, 7.6 mmol, 5 equiv) in CH$_2$Cl$_2$ (5.6 mL) was added iodine (729 mg, 2.9 mmol, 1.9 equiv). After 10 min, a solution of alcohol 23 (640 mg, 1.5 mmol, 1 equiv) in CH$_2$Cl$_2$ (2 mL; final volume 7.6 mL, 0.2M) was added, and the reaction mixture was allowed to warm to room temperature. After 12 h, the reaction mixture was diluted with CH$_2$Cl$_2$ (20 mL) and quenched with saturated aqueous sodium thiosulfate (20 mL). The aqueous layer was separated and extracted with CH$_2$Cl$_2$ (3×20 mL). The combined organic layers were dried over MgSO$_4$, filtered, and concentrated. Purification was accomplished by pH 7.0 buffered silica gel flash column chromatography (1-5% EtOAc/Hex) affording iodide 24 (740 mg, 92% yield). TLC R$_f$=0.56 (10% EtOAc/Hex); [α]$^{17}$$_D$ −14.8 (c=2.0, CH$_2$C$_{12}$); IR (thin film) 2928, 2861, 2093, 1461, 1251, 1067, 1032, 835, 773 cm$^{-1}$; $^1$H NMR (500 MHz, CDCl$_3$) δ 4.85 (d, J=4.2 Hz, 1H, C$_{11}$H), 3.99-3.90 (m, 2H), 3.84-3.78 (m, 2H), 3.68 (dd, J=5.8, 2.6 Hz, 1H, C$_{13}$H), 3.29-3.23 (m, 3H, C$_{17}$H$_a$, α-N$_3$, 3.15 (dd, J=9.7, 5.9 Hz, 1H, C$_{17}$H$_b$), 1.85-1.80 (m, 1H, C$_{12}$H), 1.79-1.70 (m, 1H, C$_{14}$H), 1.63-1.56 (m, 2H, β-N$_3$), 1.53-1.37 (m, 5H, C$_{16}$H), 1.31 (ddd, J=13.3, 7.8, 5.3 Hz, 1H, Cl$_5$H$_a$), 1.11 (ddd, J=13.5, 8.8, 6.0 Hz, 1H, C$_{15}$H$_b$), 0.97 (d, J=6.5 Hz, 3H, C$_{16}$CH$_3$), 0.90 (s, 9H, TBS), 0.87 (d, J=6.7 Hz, 3H, C$_{14}$CH$_3$), 0.07 (s, 3H, TBS), 0.06 (s, 3H, TBS); $^{13}$C NMR (125 MHz, CDCl$_3$) δ 105.1, 75.6, 64.8, 64.4, 51.3, 46.9, 42.4, 33.0, 31.5, 29.4, 26.4, 26.1, 25.4, 21.6, 18.4, 18.1, 14.5, −4.1 (2C); HRMS: Exact mass calcd for C$_{21}$H$_{41}$IN$_3$O$_3$Si [M−H]$^-$: 538.1962; found 538.1923 (FAB+).

Conjugation Reactions with C(6)-(4-azidobutyl) Dictyostatin Analog 1.

Both because of the greater ease of its synthesis and because it was found to be more potent than the C(12)-(4-azidobutyl) analog 2 (see below), the C(6)-(4-azidobutyl) analog 1 was employed in model conjugation reactions. Thus, treatment of 1 with 25, van Delft's variant of Bertozzi's cyclooctyne-based approach to metal-free click reactions (Agard, N. J. et al. 2004; Lutz, J.-F. 2008), afforded triazole 26 in 83% yield and as the expected 1:1 mixture of diastereomers (only one is shown, Scheme 4a). A traceless Staudinger (Nilsson, B. L. et al. 2000; Saxon, E. et al. 2000) ligation was also carried out to give acetamide 27 in 35% yield.

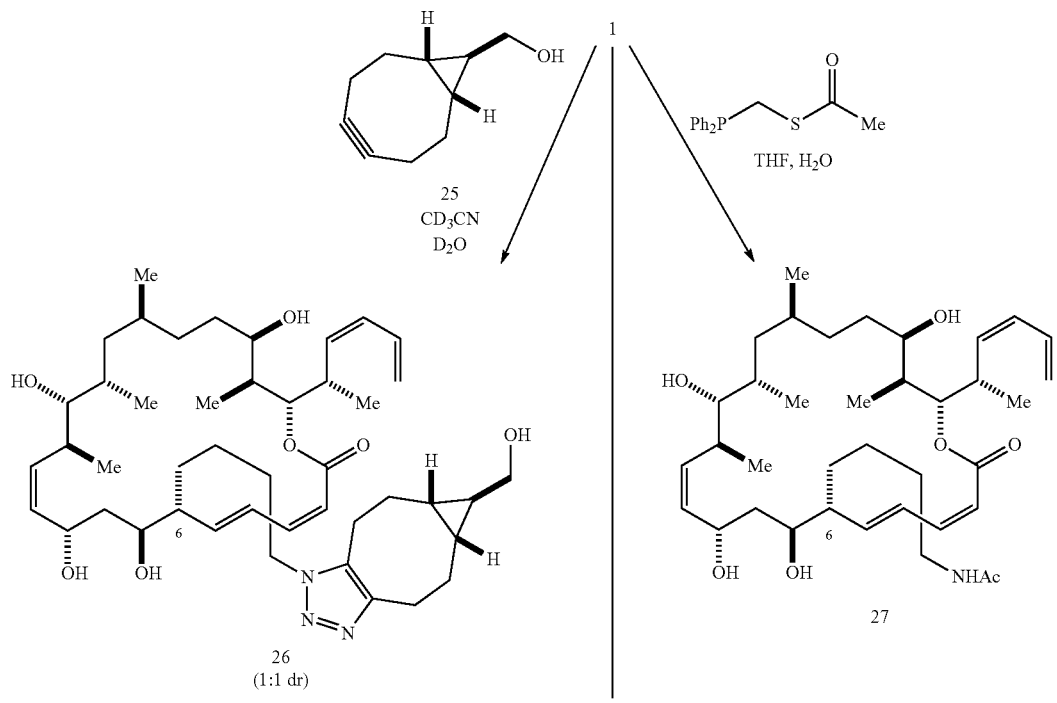

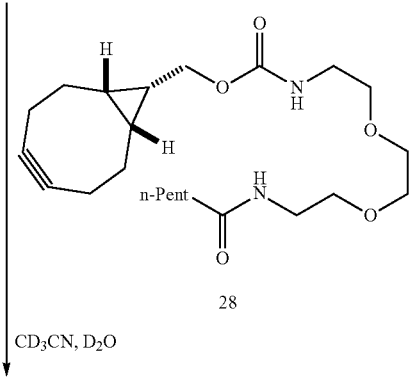

28

↓ CD₃CN, D₂O

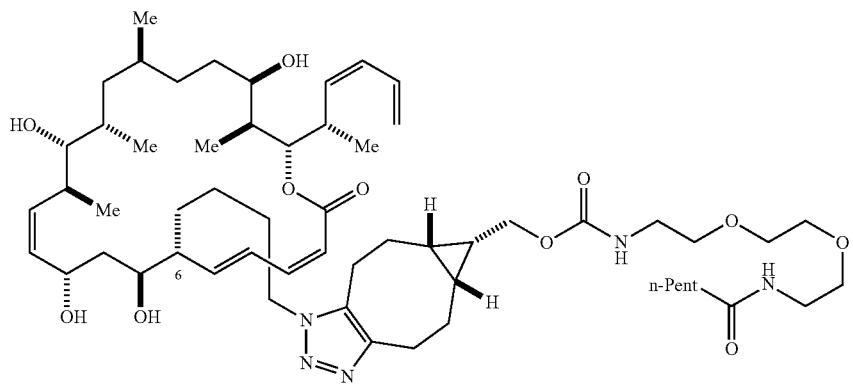

29
(1:1 dr)

Experimentals

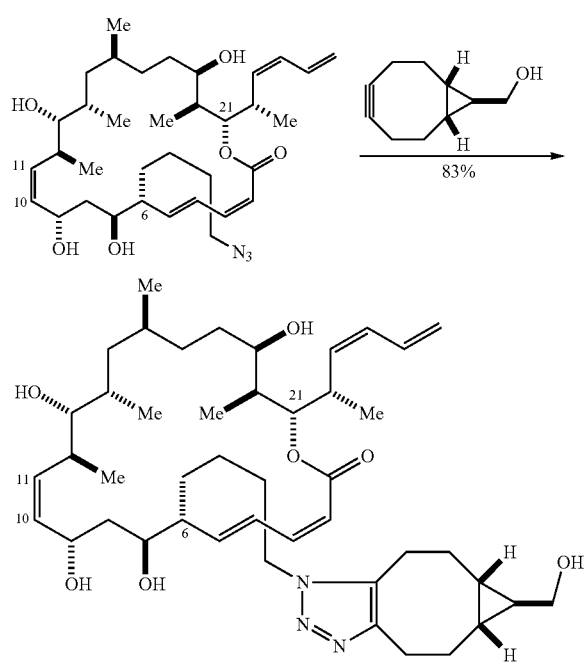

To a solution of 1 (1.0 mg, 1.6 μmol, 1 equiv) in 1:2 CD₃CN/D₂O (0.5 mL) was added cyclooctyne (2.0 mg, 13 μmol, 8 equiv). After 72 h, the reaction was directly purified by silica gel flash column chromatography (100% EtOAc to elute cyclooctyne, then 10-15% MeOH/CH$_2$Cl$_2$ to elute product) affording triazole 26 (1.0 mg, 83% yield). TLC $R_f$=0.42 (10% MeOH/CH$_2$Cl$_2$); IR (thin film) 3385 (bs), 2925, 1699, 1638, 1458, 1383, 1066, 732 cm$^{-1}$; $^1$H NMR $^1$H NMR (500 MHz, CDCl$_3$) δ 7.31 (dd, J=16.0, 11.4 Hz, 1H, C$_4$H), 6.59 (dt, J=16.9, 10.7 Hz, 1H, C$_{25}$H), 6.50-6.44 (m, 1H, C$_3$H), 6.02-5.94 (m, 2H, C$_5$H, C$_{24}$H), 5.56 (t, J=10.3 Hz, 1H, C$_{10}$H), 5.49 (d, J=11.3 Hz, 1H, C$_2$H), 5.32 (t, J=10.5 Hz, 1H, C11H), 5.26 (t, J=10.5 Hz, 1H, C$_{23}$H), 5.17 (dd, J=16.8, 2.0 Hz, 1H, C$_{26}$H$_a$), 5.09 (d, J=10.2 Hz, 1H, C$_{26}$H$_b$), 4.93 (dd, J=8.4, 2.5 Hz, 1H, C$_{21}$H), 4.79 (dt, J=10.0, 5.4 Hz, 1H, C$_9$H), 4.26-4.17 (m, 2H, α-triazole), 3.99-3.90 (m, 1H, C$_7$H), 3.60-3.53 (m, 1H), 3.51-3.42 (m, 2H, C$_{19}$H), 3.27 (d, J=7.9 Hz, 1H, C13H), 3.09 (m, 1H), 3.04-2.94 (m, 1H, C$_{22}$H), 2.90-2.80 (m, 2H), 2.79-2.71 (m, 1H, C$_{12}$H), 2.69-2.61 (m, 1H), 2.48-2.36 (m, 2H), 2.25-2.18 (m, 1H, C$_6$H), 1.90-1.85 (m, 1H, C$_{20}$H); HRMS: Exact mass calcd for C$_{45}$H$_{72}$N$_3$O$_7$[M+H]$^+$: 766.5370; found 766.5392 (FAB+).

Compound 29 was prepared similarly to the above where alkyne 25 was replaced with alkyne 28.

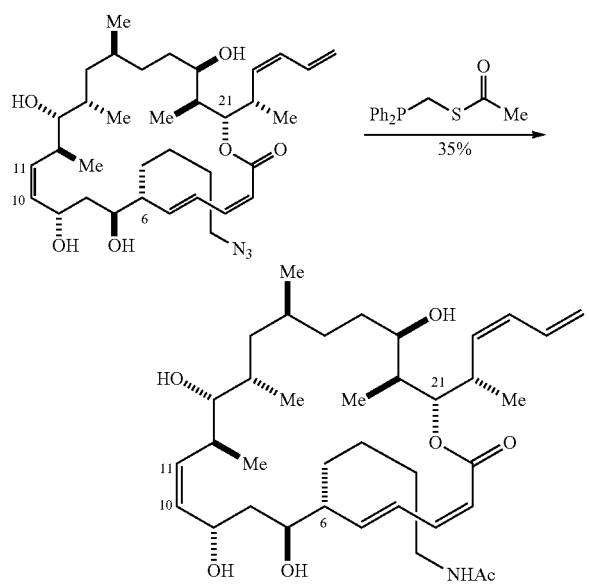

To a solution of 1 (3.4 mg, 5.5 μmol, 1 equiv) in 1:1 THF/H$_2$O (0.5 mL, degassed) was added the phosphine (15 mg, 55 μmol, 10 equiv) under Argon. After 48 h, the reaction was directly purified by silica gel flash column chromatography (100% EtOAc, then 10-20% MeOH/CH$_2$Cl$_2$) affording amide 27 (1.2 mg, 35% yield). TLC R$_f$=0.5 (10% MeOH/CH$_2$Cl$_2$); [α]$^{19}_D$ 26.2 (c=0.1, CH$_2$Cl$_2$); IR (thin film) 3358, 2923, 2854, 1696, 1638, 1460, 1440, 1274, 1174, 1120, 1064 cm$^{-1}$; $^1$H NMR $^1$H NMR (500 MHz, CDCl$_3$) δ 6.64-6.55 (m, 1H, C$_{25}$H), 6.49 (t, J=11.2 Hz, 1H, C$_3$H), 6.06-5.95 (m, 2H, C$_5$H, C$_{24}$H), 5.57 (t, J=10.2 Hz, 1H, C$_{10}$H), 5.49 (d, J=11.3 Hz, 1H, C$_2$H), 5.34 (t, J=10.5 Hz, 1H, C$_{11}$H), 5.26 (t, J=10.5 Hz, 1H, C$_{23}$H), 5.18 (d, J=17.1 Hz, 1H, C$_{26}$H$_a$), 5.10 (d, J=10.9 Hz, 1H, C$_{26}$H$_b$), 4.94 (dd, J=8.4, 2.7 Hz, 1H, C$_{21}$H), 4.84-4.76 (m, 1H, C$_9$H), 4.03-3.96 (m, 1H, C$_7$H), 3.51-3.44 (m, 1H, C$_{19}$H), 3.33-3.18 (m, 3H, C$_{13}$H, α-amide), 3.04-2.95 (m, 1H, C$_{22}$H), 2.80-2.71 (m, 1H, C$_{12}$H), 1.97 (s, 3H, NHMe); LRMS: Exact mass calcd for C$_{37}$H$_{62}$NO$_7$ [M+H]$^+$: 632.45; found 632.40 (FAB+).

Additional C(6)-Analogs

The compounds of the present invention are C(6)-analogs of dictyostatin, which have improved potency relative to dictyostatin, or similar or slightly diminished potency with an improved pharmacokinetic profile. Additional C(6)-analogs of dictyostatin are prepared using the methods described herein.

Biological Data

The C(6)- and C(12)-(4-azidobutyl) analogs 1 and 2 as well as triazole 26 and amide 27 were assayed for cell growth inhibition against four cell lines (PC3 (prostate), 1A9 (ovarian), A549 (lung), and DLD1 (colon)) alongside reference samples of synthetic dictyostatin and paclitaxel (Table 1a). Gratifyingly, the GI$_{50}$ values for the C(6) analog 1 were found to be only slightly attenuated relative to dictyostatin, while the C(12) analog 2 retains low nM potency as well, albeit with a somewhat more substantial drop in potency.

Importantly, the activity of triazole 26 against the PC3 and 1A9 cell lines is only slightly diminished from that of azide 1, while more substantial (though not catastrophic) reductions in potency are observed in the A549 and DLD1 cell lines. The potency of amide 27 is reduced by 1-2 orders of magnitude relative to azide 1 against all four cell lines. Thus, although the specific structure of the linker group—in this case a seemingly innocuous amide—can lead to moderate reductions in potency, this is likely due to a decrease in cell permeability or other factors unrelated to binding affinity for the taxane binding site.

TABLE 1a

The GI$_{50}$ values for dictyostatin analogs in cell growth inhibition assays against the PC3 (prostate), 1A9 (ovarian), A549 (lung), and DLD1 (colon) cell lines.

| | GI$_{50}$ (nM) | | | |
|---|---|---|---|---|
| compound | PC3 | 1A9 | A549 | DLD1 |
| paclitaxel | 1.9 | 0.4 | 1.2 | 15 |
| dictyostatin | 1.3 | 0.8 | 0.3 | 0.4 |
| C(6) analog 1 | 1.9 | 2.2 | 1.1 | 1.1 |
| C(12) analog 2 | 13 | 16 | 7.3 | 10 |
| triazole 26 | 4.8 | 8.4 | 25 | 13 |
| amide 27 | 50 | 30 | 22 | 32 |

DISCUSSION

Epothilone B Analogs

A linker at the C6 position has been installed in the C$_1$-C$_9$ fragment of epothilone B through a methyl modification strategy. The high resolution crystal structure of αβ-tubulin in complex with epothilone A that was reported in 2013 and indicates that the C6 methyl is solvent exposed (Prota, A. E. et al. 2013). The choice of a solvent-exposed position is vital to be able to extend the methyl group to a longer chain without altering the binding affinity. Based on this analysis, C(6)-(4-azidobutyl) analog 19 was targeted.

The results contained herein establish a validated linker strategy for Epo B in the form of C(6)-(4-azidobutyl) analog 19 which may be reacted to form a triazole or amide analog which maintains or increases anti-cancer potency.

An additional aspect of the invention provides synthetic methods and chemical intermediates that may be used to access, modify, or encompass chemical space at the C(6) position of the Epo B core. Additional compounds may be synthesized according to the protocols described in Schemes 1-6, and possess analogous biological activity and function to the compounds disclosed in Table 1.

Dictyostatin Analogs

The principal challenge in the identification of modifiable sites on polyketide/polypropionate structures such as dictyostatin is that the hydroxyl groups may be the only readily modifiable groups (FIG. 2A). The choice to pursue an alcohol modification strategy would thus typically be made for reasons of synthetic convenience and would require the identification of an "innocent" hydroxyl group that neither interacts with the receptor nor engages in any intramolecular interactions that are critical for activity as well as a synthetic strategy to allow for selective modification of only that hydroxyl group.

Cognizant that both of Paterson and Wright's demonstration that the C(9)-OMe analog retains the low nM potency of the natural product (Paterson, I. et al. 2011), and that the penultimate intermediate in our synthesis is one in which the C(9)-OH group is, uniquely, unprotected (FIG. 2B), a C(9)-OH modification approach was rejected because 1) that complex ether formation with our late stage intermediate might be difficult and 2) that acylation, the synthetically straightforward alternative, might be expected to subtly but significantly perturb the local electronic and steric structure and global conformation of the natural product as well as raise concerns about acyl group migration or cleavage in vivo (FIG. 2C). Indeed, these concerns were not strictly hypothetical, as Paterson has demonstrated that analogs of a dictyostatin/discodermolide hybrid structure in which the C(7)- and C(9)-OH groups were acylated with taxoid sidechains were surprisingly susceptible both to acyl migration (between the C(7) and C(9) alcohols) and to cleavage by methanolysis (Paterson, I. et al. 2011). Further, although interpretation of the data is complicated by the acyl migration issue, the C(7)- and C(9)-OH acylated analogs were significantly less potent than the parent unacylated hybrid compound.

Having rejected an alcohol acylation strategy, it was envisioned that the "ideal" approach for polyketides/polypropionates with few or no obvious handles for linker attachment would entail modifying one of the ubiquitous methyl groups to a linker functionality-equipped linear alkyl group (FIG. 2C). This approach was expected to result in as minimal a perturbation of the structure and conformation of the natural product as possible, while also obviating any concerns about unwanted O-acyl migration or cleavage. It is noted that in the course of a project designed to identify a modifiable site on the related MSA natural product discodermolide, Schreiber expressed similar reservations regarding an alcohol acylation strategy and pursued, as one among several different alternative approaches, the synthesis of a methyl extended analog of the type under discussion here, a report that constitutes the sole direct precedent we have been able to identify (Hung, D. T. et al. 1996).

For guidance as to the selection of appropriately disposed methyl groups the extensive structure-activity relationship (SAR) data for dictyostatin reported by Curran (Fukui, Y. 2006; Shin, Y. et al. 2007; Jung, W.-H. et al. 2007; Zhu, W. et al. 2010; Jiménez, M. et al. 2011) and Paterson (Paterson, I. et al. 2008; Paterson, I. et al. 2009; Paterson, I. et al. 2009) was looked at, particularly as they related to the starkly contrasting models for the binding of dictyostatin in the taxane binding site advanced by Curran and Snyder (Jogalekar, A. et al. 2011) and by Díaz and Jiménez-Barbero (Canales, A. et al. 2008).

Figure 3A:
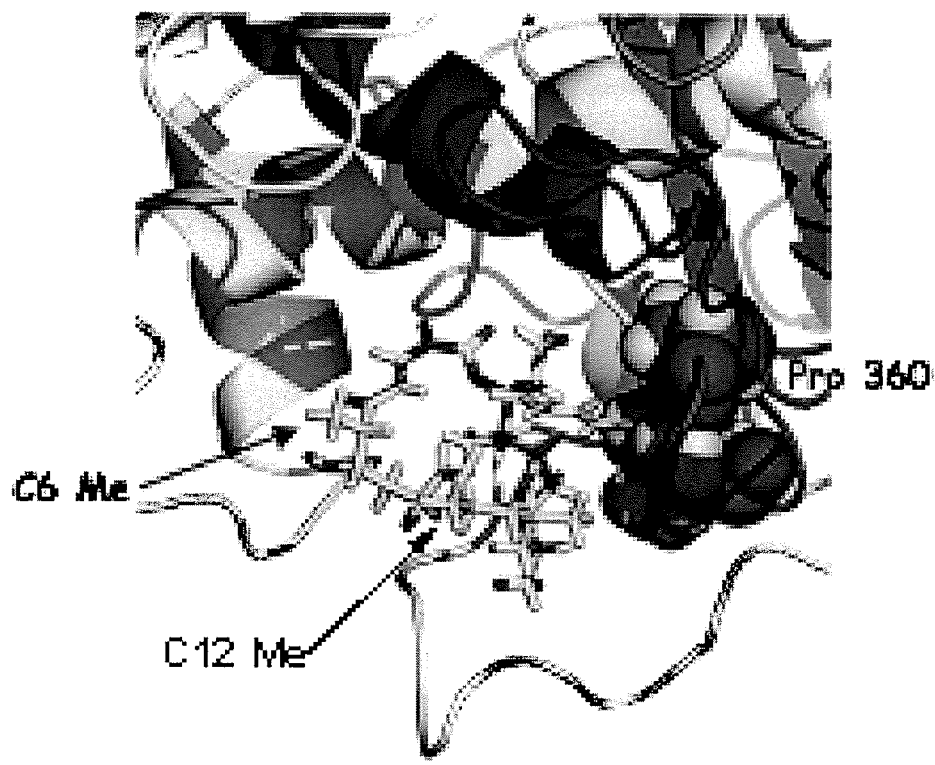
FIG. 3A: The Curran/Snyder model for the binding of dictyostatin in the taxane binding site of β-tubulin suggests that the C(6) and C(12) methyl groups are solvent exposed and not in van der Waals contact with the receptor.
Figure 3B:
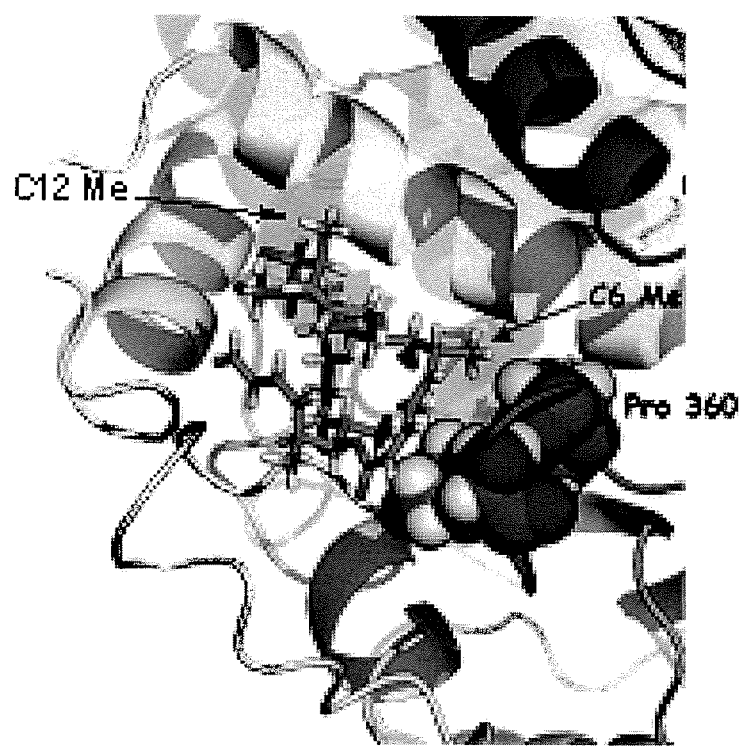
FIG. 3B: The Curran/Snyder rendering of the Díaz/Jiménez-Barbero model for the binding of dictyostatin in the taxane binding site of β-tubulin locates the C(6) and C(12) methyl groups deeper into the binding pocket and near to/in van der Waals contact with active site residues.
Figure 3C:
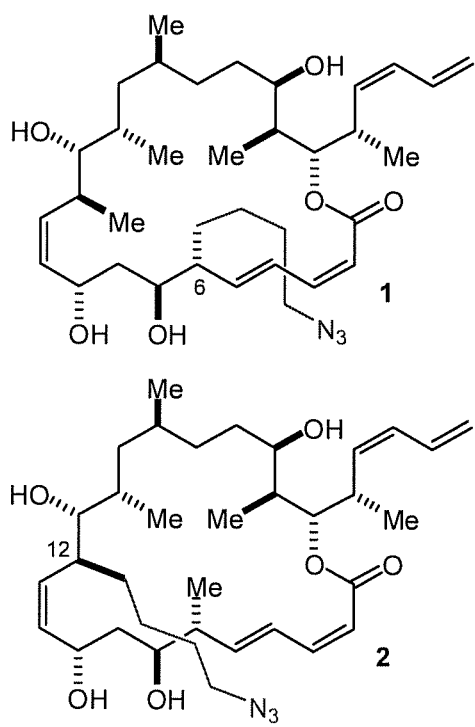
FIG. 3C: Based on the Curran/Snyder model, the C(6)- and C(12)-(4-azidobutyl) methyl extended dictyostatin analogs 3 and 4 are predicted to retain the potency of the parent natural product dictyostatin.

Curran demonstrated that the C(6)-epi dictyostatin is as potent as the natural product and Paterson's demonstrated that C(6)-normethyl dictyostatin is only slightly less potent (≤1 order of magnitude) than the natural product. According to Curran and Snyder, only their model (FIG. 3A) is fully consistent with this SAR data, as it places the C(6)-methyl group in a solvent exposed position without contacts to the receptor. Conversely, Curran and Snyder's rendering of the Díaz/Jiménez-Barbero model (FIG. 3B) places the C(6)-methyl group further into the binding pocket and in van der Waals contact with Pro360, which Curran and Snyder contend is inconsistent with the SAR data because deletion or epimerization of the C(6)-methyl group would remove this contact with Pro360 and be expected to lead to a significant decrease in potency. The models also lead to similar conclusions regarding the C(12)-methyl group, though here more caution is warranted in that the Curran/Snyder model, which otherwise appears to place the C(12)-methyl group in a relatively open space, locates it in proximity to the M-loop (the loop at the very bottom of FIG. 3A), which undergoes significant conformational changes upon the binding of an MSA in the taxane binding pocket (Prota, A. et al. 2013). The two models locate the C(6)- and C(12)-methyl groups either in a solvent exposed orientation (Curran and Snyder) or deeper into the binding pocket (Díaz and Jiménez-Barbero), with the C(6)-methyl (and other) SAR data appearing to be better rationalized by the Curran and Snyder model. Based on this analysis, C(6)- and C(12)-(4-azidobutyl) analogs 1 and 2 (FIG. 3C) were targeted, which would in the process provide additional support for the Curran and Snyder binding model.

Together, these results 1) establish a validated linker strategy for dictyostatin in the form of C(6)-(4-azidobutyl) analog 1 which may be reacted to form a triazole conjugate with only trivial or small reductions in potency, and 2) constitute compelling evidence in support of the Curran/Snyder model in which the C(6)- and C(12)-methyl groups are in solvent exposed orientations, and in opposition to the Díaz/Jiménez-Barbero model in which the C(6)- and C(12)-methyl groups are located deeper into the binding pocket and near to/in van der Waals contact with active site residues. More broadly, this work demonstrates that even in cases where a synthetically convenient alcohol acylation strategy presents itself, the "methyl extension" strategy outlined here merits strong consideration, as it is less likely to result in significant attenuations in potency and obviates any and all concerns about unwanted reactivity. Of course, it remains the case that the methyl extension approach is more synthetic chemistry intensive, but in that regard it is noted 1) that major improvements in step-economy and scalability such as in our dictyostatin synthesis can render this approach feasible in a far less time- and resource-intensive way, and 2) that two ways have been demonstrated in which our efficient and scalable polyketide/polypropionate synthesis methodologies may easily be adapted for the installation of 4-azidobutyl groups in place of methyl groups. As described above, the realization of this strategy has put us in position to pursue the synthesis and evaluation of dictyostatin conjugates.

An additional aspect of the invention provides synthetic methods and chemical intermediates that may be used to access, modify, or encompass chemical space at the C(6) position of the dictyostatin core. Additional compounds may be synthesized according to the protocols described in Schemes 1a-4a, and possess analogous biological activity and function to the compounds disclosed in Table 1a.

REFERENCES

Antibody Drug Conjugates
Chari, R. V. J. et al. Antibody-drug conjugates: an emerging concept in cancer therapy. Angew Chem Int Ed Engl. 2014, 53, 3796-827.
Carter, P. J. et al. Antibody-drug conjugates for cancer therapy. Cancer J. 2008, 14, 154-69.
Ducry, L., Stump, B. Antibody-drug conjugates: linking cytotoxic payloads to monoclonal antibodies. Bioconjugate Chem. 21, 5-13 (2010).
Perez, H. L. et al. Antibody-drug conjugates: current status and future directions. Drug Discov Today. 2014, 19, 869-81.
Epithilones
Aghajanian, C. et al. Phase I study of the novel epothilone analog ixabepilone (BMS-247550) in patients with advanced solid tumors and lymphomas. J Clin Oncol. 2007, 25, 1082-8.
Altmann, K.-H.; Pfeiffer, B.; Arseniyadis, S.; Pratt, B. A.; Nicolaou, K. C. The Chemistry and Biology of Epothilones—The Wheel Keeps Turning. *Chem Med Chem* 2007, 2, 396-423.
Altmann, K. H.; Wartmann, M.; O'Reilly, T. Epothilones and Related Structures—A New Class of Microtubule Inhibitors with Potent in Vivo Antitumor Activity. *Biochim. Biophys. Acta* 2000, 1470, M79-M91.

Bollag, D. et al. Epothilones, a New Class of Microtubule-Stabilizing Agents with a Taxol-like Mechanism of Action. *Cancer Res.* 1995, 55, 2325-2333.

Chou, T-C. et al. Desoxyepothilone B: an efficacious microtubule-targeted antitumor agent with a promising in vivo profile relative to epothilone B. Proc Natl Acad Sci USA. 1998, 95, 9642-7.

Chou, T-C. et al. Therapeutic effect against human xenograft tumors in nude mice by the third generation microtubule stabilizing epothilones. Proc Natl Acad Sci USA. 2008, 105, 13157-62.

Dommerholt, J. et al. Readily Accessible Bicyclononynes for Bioorthogonal Labeling and Dhree-Dimensional Imaging of Living Cells. *Angew. Chem. Int. Ed.* 2010, 49, 9422-9425.

Gerth, K. et al. Epothilons A and B: Antifungal and Cytotoxic Compounds from *Sorangium Cellulosum* (Myxobacteria). Production, Physico-Chemical and Biological Properties. *J. Antibiot.* 1996, 49, 560-563.

Giannakakou, P. et al. Paclitaxel-Resistant Human Ovarian Cancer Cells Have Mutant Beta-Tubulins That Exhibit Impaired Paclitaxel-Driven Polymerization. *J. Biol. Chem.* 1997, 272, 17118-17125.

Harris, C.; Danishefsky, S. Complex Target-Oriented Synthesis in the Drug Discovery Process: A Case History in the dEpoB Series. *J. Org. Chem.* 1999, 8434-8456.

Hein, J. E.; Fokin, V. V. Copper-Catalyzed Azide-Alkyne Cycloaddition (CuAAC) and Beyond: New Reactivity of Copper(I) Acetylides. *Chem. Soc. Rev.* 2010, 39, 1302-1315.

Hofle, G.; Bedorf, N.; Steinmetz, H.; Schomburg, D.; Gerth, K.; Reichenbach, H. Epothilone A and B—Novel 16-Membered Macrolides with Cytotoxic Activity: Isolation, Crystal Structure, and Conformation in Solution. *Angew. Chem. Int. Ed.* 1996, 35, 1567-1569.

US Patent Application Publication No. 2006/0046997 A1, published Mar. 2, 2006 (Klar et al.).

Klar, U. et al. Total synthesis and antitumor activity of ZK-EPO: the first fully synthetic epothilone in clinical development. Angew Chem Int Ed Engl. 2006, 45, 7942-8.

Klar, U. et al. Asymmetric Total Synthesis of the Epothilone Sagopilone—From Research to Development. Synlett 2012, 23, 12-91-99.

Nicolaou, K. C.; Roschangar, F.; Vourloumis, D. Chemical Biology of Epothilones. *Angew. Chem. Int. Ed.* 1998, 37, 2014-2045.

Nicolaou, K. C.; Ritzen, A.; Namoto, K. Recent Developments in the Chemistry, Biology and Medicine of the Epothilones. *Chem. Commun.* 2001, 1523-1535.

Pfeiffer, B. et al. Epothilones as Lead Structures for New Anticancer Drugs. RSC Discovery Series No. 25—Drug Discover from Natural Products, Chapter 16. Royal Society of Chemistry 2012.

Prota, A. E.; Bargsten, K.; Zurwerra, D.; Field, J. J.; Díaz, J. F.; Altmann, K.-H.; Steinmetz, M. O. Molecular Mechanism of Action of Microtubule-Stabilizing Anticancer Agents. Science 2013, 339, 587-590.

Rivkin, A. et al. On the Introduction of a Trifluoromethyl Substituent in the Epothilone Setting: Chemical Issues Related to Ring Forming Olefin Metathesis and Earliest Biological Findings. *Org. Lett.* 2002, 4, 4081-4084.

Rivkin, A. et al. Complex Target-Oriented Total Synthesis in the Drug Discovery Process: The Discovery of a Highly Promising Family of Second Generation Epothilones. *J. Am. Chem. Soc.* 2003, 125, 2899-2901.

Rivkin, A. et al. Discovery of (E)-9,10-Dehydroepothilones through Chemical Synthesis: On the Emergence of 26-Trifluoro-(E)-9,10-Dehydro-12,13-Desoxyepothilone B as a Promising Anticancer Drug Candidate. *J. Am. Chem. Soc.* 2004, 126, 10913-10922.

Rowinsky, E. K. The Development and Clinical Utility of the Taxane Class of Antimicrotubule Chemotherapy Agents. *Annu. Rev. Med.* 1997, 48, 353-374.

Soellner, M. B.; Nilsson, B. L.; Raines, R. T. Reaction Mechanism and Kinetics of the Traceless Staudinger Ligation. *J. Am. Chem. Soc.* 2006, 128, 8820-8828.

Stachel, S. J.; Danishefsky, S. J. Chemo- and Stereoselective Epoxidation of 12,13-Desoxyepothilone B Using 2,2'-Dimethyldioxirane. Tetrahedron Lett. 2001, 42, 6785-6787.

Dictyostatins

Agard, N. J., Prescher, J. A., Bertozzi, C. R. A strain promoted [3+2] azide-alkyne cycloaddition for covalent modification of biomolecules in living systems. J. Am. Chem. Soc. 126, 15046-15047 (2004).

Brunden, K. R. et al. MT-Stabilizer, Dictyostatin, Exhibits Prolonged Brain Retention and Activity: Potential Therapeutic Implications. ACS Med. Chem. Lett. 4 (9), pp 886-889 (2013).

Canales, A. et al. The bound conformation of microtubule-stabilizing agents: NMR insights into the bioactive 3D Structure of discodermolide and dictyostatin. Chem. Eur. J. 14, 7557-7569 (2008).

Corey, E. J., Helal, C. J. Reduction of carbonyl compounds with chiral oxazaborolodine catalysts: a new paradigm for enantioselective catalysis and a powerful new synthetic method. Angew. Chem. Int. Ed. 37, 1986-2012 (1998).

Dommerholt, J. et al. Readily accessible bicyclononynes for bioorthogonal labeling and three-dimensional imaging of living cells. Angew. Chem. Int. Ed. 49, 9422-9425 (2010).

Eiseman, J. L. et al. Improved Synthesis of 6-epi-Dictyostatin and Antitumor Efficacy in Mice Bearing MDA-MB231 Human Breast Cancer Xenografts. J. Med. Chem. 51, 6650-6653 (2008).

Foley, C. N., Leighton, J. L. Beyond the Roche ester: a new approach to polypropionate stereotriad synthesis. Org. Lett. 16, 1180-1183 (2014).

Fukui, Y., Brtckner, A. M., Shin, Y., Balachandran, R., Day, B. W., Curran, D. P. Fluorous mixture synthesis of (−)-dictyostatin and three stereoisomers. Org. Lett. 8, 301-304 (2006).

Garber, S. B., Kingsbury, J. S., Gray, B. L., Hoveyda, A. H. Efficient and recyclable monomeric and dendritic Ru-based metathesis catalysts. J. Am. Chem. Soc. 122, 8168-8179 (2000).

Ho, S., Bucher, C., Leighton, J. L. A highly step-economical synthesis of dictyostatin. Angew. Chem. Int. Ed. 52, 6757-6761 (2013).

Hung, D. T., Nerenberg, J. B., Schreiber, S. L. Syntheses of discodermolides useful for investigating microtubule binding and stabilization. J. Am. Chem. Soc. 118, 11054-11080 (1996).

Isbrucker, R. A. et al. Tubulin polymerizing activity of dictyostatin-1, a polyketide of marine sponge origin. Biochem. Pharmacol. 66, 75-82 (2003).

Jiménez, M. et al. Efficient syntheses of 25,26-dihydrodictyostatin and 25,26-dihydro-6-epi-dictyostatin, two potent new microtubule-stabilizing agents. Beilstein J. Org. Chem. 7, 1372-1378 (2011).

Jogalekar, A. et al. Dictyostatin flexibility bridges conformations in solution and in the β-tubulin taxane binding site. J. Am. Chem. Soc. 133, 2427-2436 (2011).

Jung, W.-H., Harrison, C., Shin, Y., Fournier, J.-H., Balachandran, R., Raccor, B. S., Sikorski, R. P., Vogt, A., Curran, D. P., Day, B. W. Total synthesis and biological evaluation of C16 analogs of (−)-dictyostatin. J. Med. Chem. 50, 2951-2966 (2007).

Kim, H., Ho, S., Leighton, J. L. A more comprehensive and highly practical solution to enantioselective aldehyde crotylation. J. Am. Chem. Soc. 133, 6517-6520 (2011).

Lutz, J.-F. Copper-free azide-alkyne cycloadditions: new insights and perspectives. Angew. Chem. Int. Ed. 47, 2182-2184 (2008).

Nilsson, B. L., Kiessling, L. L., Raines, R. T. Staudinger ligation: a peptide from a thioester and azide. Org. Lett. 2, 1939-1941 (2000).

Paterson, I.; Britton, R.; Delgado, O.; Wright, A. E. Stereochemical determination of dictyostatin, a novel microtubule-stabilising macrolide from the marine sponge Corallistidae sp. *Chem. Commun.* 632-633 (2004).

Paterson, I., Gardner, N. M., Poullennec, K. G., Wright, A. E. Synthesis and biological evaluation of novel analogues of dictyostatin. Bioorg. Med. Chem. Lett. 17, 2443-2447 (2007).

Paterson, I., Gardner, N. M., Poullennec, K. G., Wright, A. E. Synthesis and biological evaluation of 10,11-dihydrodictyostatin, a potent analogue of the marine anticancer agent dictyostatin. J. Nat. Prod. 71, 364-369 (2008).

Paterson, I., Gardner, N. M., Naylor, G. J. Total synthesis of novel dictyostatin analogs and hybrids as microtubule-stabilizing anticancer agents. Pure Appl. Chem. 81, 169-180 (2009).

Paterson, I., Gardner, N. M., Guzmán, E., Wright, A. E. Total synthesis and biological evaluation of novel $C_2$-$C_6$ region analogues of dictyostatin. Bioorg. Med. Chem. 17, 2282-2289 (2009).

Paterson, I., Naylor, G. J., Gardner, N. M., Guzmán, E., Wright, A. E. Total synthesis and biological evaluation of a series of macrocyclic hybrids and analogues of the antimitotic natural products dictyostatin, discodermolide, and taxol. Chem. Asian J. 6, 459-473 (2011).

Pettit, G. R., Cichacz, Z. A., Gao, F., Boyd, M. R., Schmidt, J. M. Isolation and structure of the cancer cell growth inhibitor dictyostatin 1. J. Chem. Soc., Chem. Commun. 1111-1112 (1994).

Prota, A. E. et al. Molecular mechanism of action of microtubule-stabilizing anticancer agents. Science, 339, 587-590 (2013).

Saxon, E., Armstrong, J. I., Bertozzi, C. R. A 'traceless' Staudinger ligation for the chemoselective synthesis of amide bonds. Org. Lett. 2, 2141-2143 (2000).

Shiina, I. et al. An effective use of benzoic anhydride and its derivatives for the synthesis of carboxylic esters and lactones: a powerful and convenient mixed anhydride method promoted by basic catalysts. J. Org. Chem. 69, 1822-1830 (2004).

Shin, Y. et al. Synthesis and biological evaluation of (−)-dictyostatin and stereoisomers. Tetrahedron 63, 8537-8562 (2007).

Sochaj, A. M, et al. Current methods for the synthesis of homogeneous antibody-drug conjugates. *Biotechnol Adv.* in press (2015).

Vlahov, I. R. and Leamon, C. P. Engineering Folate-Drug Conjugates to Target Cancer: From Chemistry to Clinic. *Bioconjugate Chem.* 2012, 23 (7), pp 1357-1369 (2012).

Zhu, W. et al. Streamlined syntheses of (−)-dictyostatin, 16-desmethyl-25,26-dihydrodictyostatin, and 6-epi-16-desmethyl-25,26-dihydrodictyostatin. J. Am. Chem. Soc. 132, 9175-9187 (2010).

What is claimed is:
1. A compound having the structure:

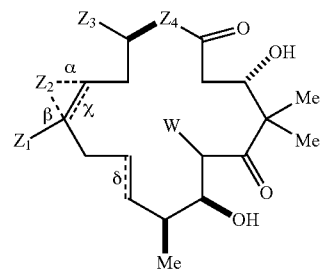

wherein
$Z_1$ is —$CH_3$ or —$CF_3$;
$Z_2$ is absent or present and when present is —O—;
$Z_3$ is

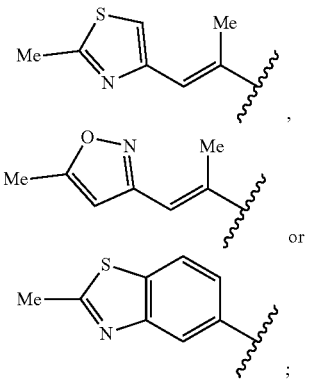

$Z_4$ is —O— of —NH—;
W is alkyl-$N_3$, alkyl-SH, $C_4$-$C_{20}$ alkyl-OH, $C_4$-$C_{20}$ alkyl-$NH_2$, alkyl-NH—$R_1$, alkyl-$NR_2R_3$, alkyl-$OR_1$, alkyl-OC(O)—$R_1$, alkyl-NHAc, alkyl-NHC(O)—$R_1$, -alkyl-NHC(O)—$R_4$, alkyl-OC(O)—$OR_1$, alkyl-NHC(O)—$NHR_1$, alkyl-NHC(S)—$NHR_1$ or alkyl-maleimide,
wherein
 $R_1$ is alkyl-$N_3$, alkyl-SH, alkyl-OH, alkyl-$NH_2$, or alkyl-maleimide,
 $R_2$ is alkyl-$N_3$, alkyl-SH, alkyl-OH, alkyl-$NH_2$, or alkyl-maleimide,
 $R_3$ is alkyl-$N_3$, alkyl-SH, alkyl-OH, alkyl-$NH_2$, or alkyl-maleimide, and
 $R_4$ is alkyl-$N_3$, alkyl-SH, alkyl-OH, alkyl-$NH_2$ or alkyl-maleimide,
α is a bond and is absent or present,
β is a bond and is absent or present,
χ is a bond and is absent or present,
δ is a bond and is absent or present,
 wherein when α, β, and $Z_2$ are present, then χ is absent, and when χ is present, then α, β, and $Z_2$ are absent
or a stereoisomer or a pharmaceutically acceptable salt or ester thereof.

2. The compound of claim 1 having the structure:
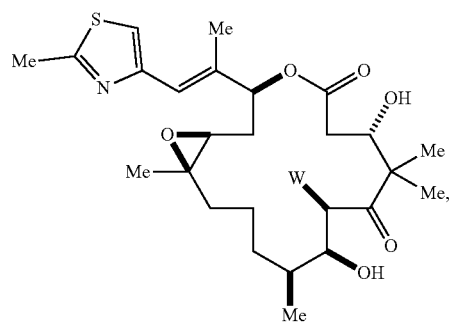
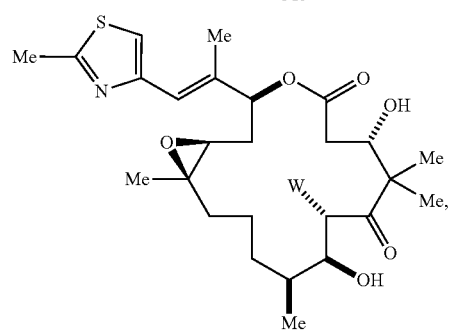
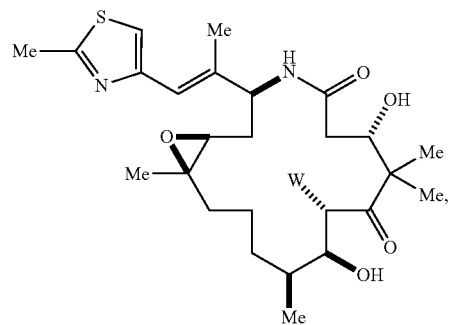
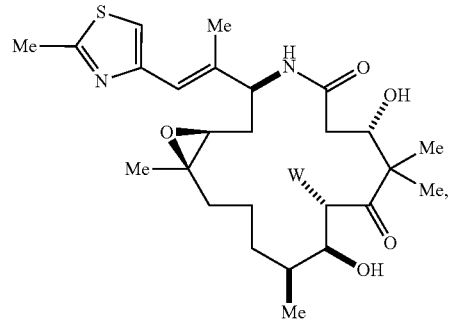
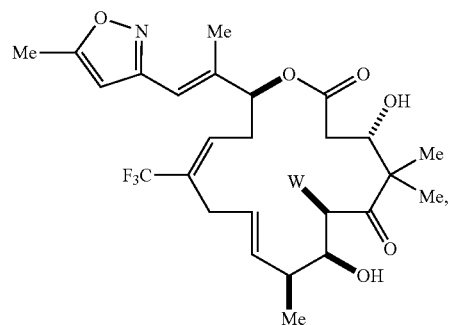
-continued
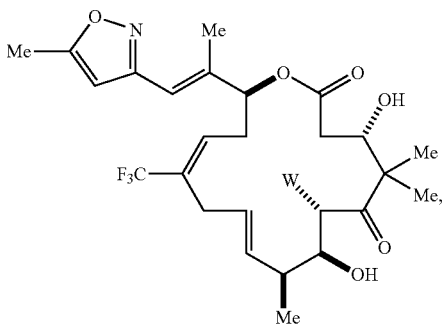
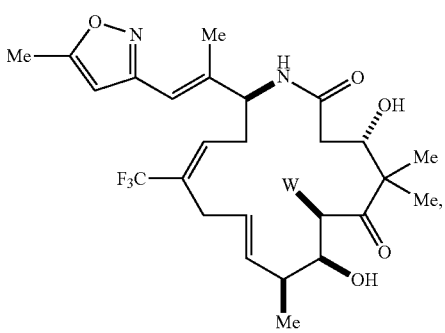
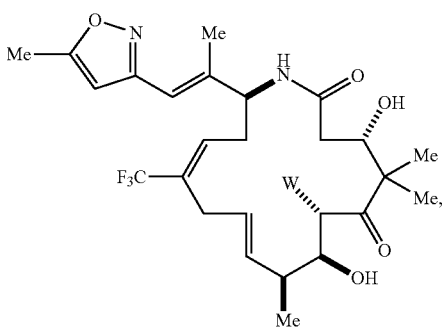
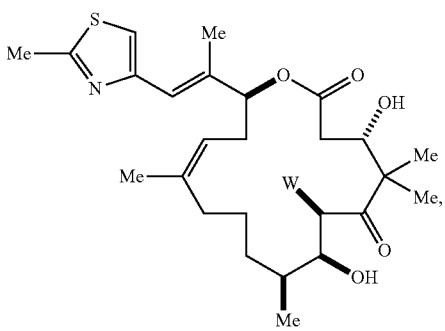
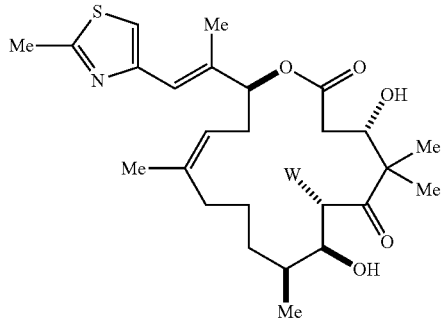

107

-continued

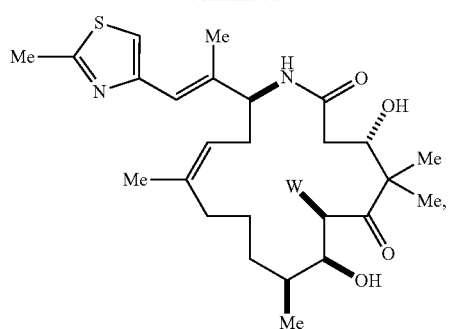

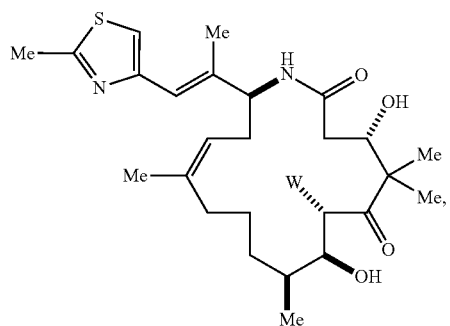

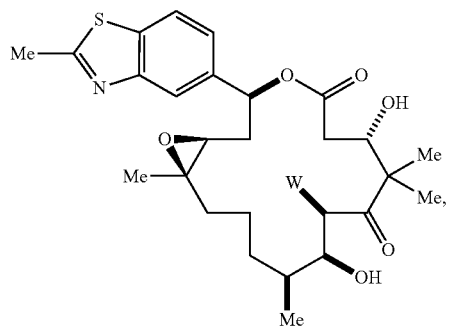

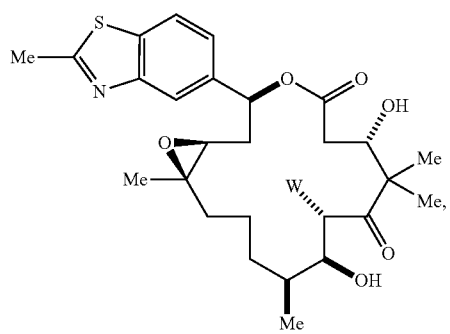

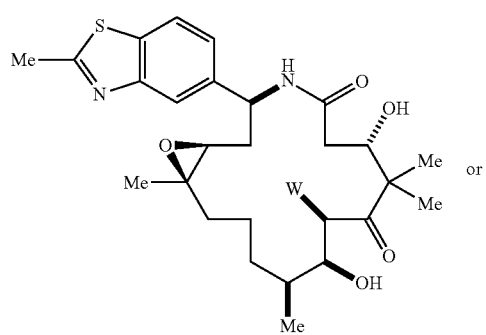

108

-continued

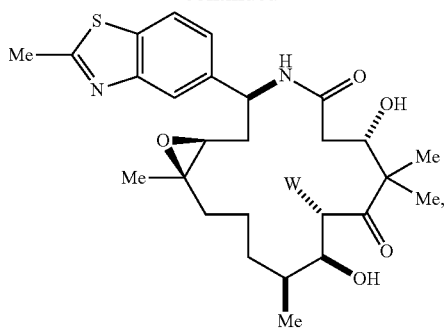

or a stereoisomer or a pharmaceutically acceptable salt or ester thereof.

3. The compound of claim 1 having the structure:

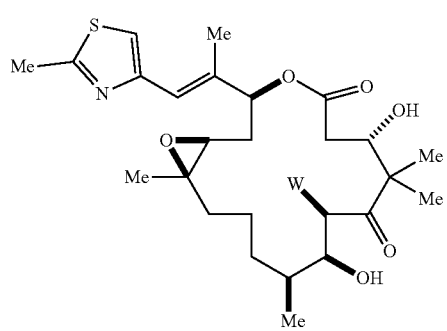

or a stereoisomer or a pharmaceutically acceptable salt or ester thereof.

4. The compound of claim 1, wherein W is —(CH$_2$)$_n$—N$_3$, wherein n is 1-20; or W is —(CH$_2$)$_n$—NHAc, wherein n is 1-20, or a stereoisomer or a pharmaceutically acceptable salt or ester thereof.

5. The compound of claim 1, wherein W is

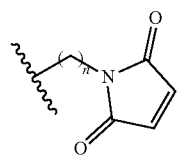 or 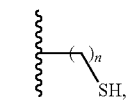

wherein n is 1-20, or

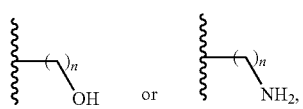
wherein n is 4-20.
6. The compound of claim 3 having the structure:
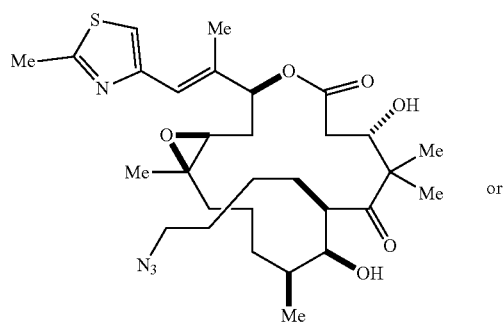 or 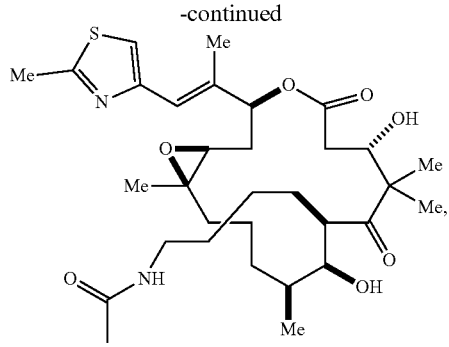
or a stereoisomer or a pharmaceutically acceptable salt or ester thereof.
7. A composition comprising the compound of claim 1 and a carrier.
8. A composition, free of soil extract, comprising the compound of claim 1.
9. A composition, free of soil extract, comprising at least 1 mg of the compound of claim 1.
* * * * *